(12) United States Patent
Carbonell

(10) Patent No.: US 10,023,638 B2
(45) Date of Patent: Jul. 17, 2018

(54) ANTI-INTEGRIN β1 ANTIBODY COMPOSITIONS AND METHODS OF USE THEREOF

(71) Applicant: ONCOSYNERGY, INC., San Francisco, CA (US)

(72) Inventor: W. Shawn Carbonell, Burlingame, CA (US)

(73) Assignee: Oncosynergy, Inc., San Francisco, CA (US)

( * ) Notice: Subject to any disclaimer, the term of this patent is extended or adjusted under 35 U.S.C. 154(b) by 59 days.

(21) Appl. No.: 14/140,340

(22) Filed: Dec. 24, 2013

(65) Prior Publication Data

US 2014/0328830 A1 Nov. 6, 2014

Related U.S. Application Data

(60) Provisional application No. 61/746,023, filed on Dec. 26, 2012.

(51) Int. Cl.
| | |
|---|---|
| *C07K 16/00* | (2006.01) |
| *C07K 16/46* | (2006.01) |
| *C07K 16/28* | (2006.01) |
| *A61K 49/00* | (2006.01) |
| *G01N 33/574* | (2006.01) |
| *A61K 47/68* | (2017.01) |
| *A61K 39/00* | (2006.01) |

(52) U.S. Cl.
CPC ...... *C07K 16/2842* (2013.01); *A61K 47/6803* (2017.08); *A61K 49/0004* (2013.01); *G01N 33/57484* (2013.01); *A61K 2039/505* (2013.01); *C07K 2317/24* (2013.01); *C07K 2317/55* (2013.01); *C07K 2317/622* (2013.01); *C07K 2317/70* (2013.01); *C07K 2317/76* (2013.01); *C07K 2317/92* (2013.01); *G01N 2333/7055* (2013.01)

(58) Field of Classification Search
None
See application file for complete search history.

(56) References Cited

U.S. PATENT DOCUMENTS

| | | | | |
|---|---|---|---|---|
| 5,530,101 | A * | 6/1996 | Queen | C07K 16/00 424/133.1 |
| 5,859,205 | A * | 1/1999 | Adair | C07K 16/18 530/387.1 |
| 5,998,586 | A | 12/1999 | Bodmer et al. | |
| 6,548,640 | B1 * | 4/2003 | Winter | C07K 16/464 424/130.1 |
| 7,465,572 | B2 * | 12/2008 | Carr | C07K 14/3153 424/94.1 |
| 2007/0003547 | A1 | 1/2007 | Foote | |
| 2008/0070835 | A1 | 3/2008 | Sugiyama | |
| 2011/0318347 | A1 | 12/2011 | Blanchetot et al. | |

FOREIGN PATENT DOCUMENTS

| | | | |
|---|---|---|---|
| CA | 2577370 A1 | | 3/2006 |
| WO | WO1993017105 | * | 9/1993 |
| WO | WO 1996/08564 A1 | | 3/1996 |
| WO | WO 1999/55369 A1 | | 11/1999 |
| WO | WO 2004/056308 A2 | | 7/2004 |
| WO | WO 2004/061073 A2 | | 7/2004 |
| WO | WO/2006/082406 | * | 8/2006 |
| WO | WO 2007/134876 A2 | | 11/2007 |
| WO | WO 2009/009114 A2 | | 1/2009 |
| WO | WO 2009/042746 A1 | | 4/2009 |
| WO | WO 2011/149461 A1 | | 12/2011 |
| WO | WO 2012/129448 A1 | | 9/2012 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol., Jul. 5, 2002, 320(2):415-28.*
Eduardo Padlan, Anatomy of the antibody molecule. Mol Immunol. Feb. 1994;31(3):169-217.*
Paul, Fundamental Immunology, 3rd Edition, 1993, pp. 292-295.*
Klimka et al.,Human anti-CD30 recombinant antibodies by guided phage antibody selection using cell panning. British Journal of Cancer (2000) 83:252-260.*
Casset et al. A peptide mimetic of an anti-CD4 monoclonal antibody by rational design. Biochemical and Biophysical Research Commmunications, 307:198-205, 2003.*
Rudikoff et al Single amino acid substitution altering antigen-binding specificity. Proc Natl Acad Sci U S A. Mar. 1982;79(6):1979-83.*
Beiboer et al., Guided selection of a pan carcinoma specific antibody reveals similar binding characteristics yet structural divergence between the original murine antibody and its human equivalent. J. Mol. Biol. 296: 833-849 (2000).*
Poul et al. Inhibition Of T Cell Activation With a Humanized Anti-β1 Integrin Chain mAb. Molecular Immunology, vol. 32, No. 2, pp. 101-116, 1995.*
Juul, L. et al.: "A New Apparently Functional IGVK Gene (Vkla) Present in Some Individuals Only"; Immunogenetics. 1998, vol. 48; pp. 40-46.
Chan, S et al.: "Human Recombinant Antibodies Specific for Hepatitis C Virus Core and Envelope E2 Peptides From an Immune Phage Display" Library. Journal of General Virology; 1996, vol. 77; pp. 2531-2539.

(Continued)

*Primary Examiner* — Maher M Haddad
(74) *Attorney, Agent, or Firm* — DLA Piper LLP (US)

(57) ABSTRACT

The current invention provides human variable chain framework regions and humanized antibodies comprising the framework regions, the antibodies being specific for integrin β1. The invention also provides methods for utilizing the antibodies, for example to treat diseases such as cancer.

21 Claims, 36 Drawing Sheets

(56) References Cited

OTHER PUBLICATIONS

International Search Report regarding PCT/US2013/077707.
Supplementary Partial European Search Report dated May 30, 2016, regarding EP 13 86 7136.7.
Almagro, Juan C. et al.: "*Humanization of antibodies*"; Frontiers in Bioscience, Albertson, NY, US, vol. 13, Jan. 1, 2008, pp. 1619-1633.
Park, C. C. et al.:"$\beta_1$ *Integrin Inhibition Dramatically Enhances Radiotherapy Efficacy in Human Breast Cancer Xenografts*"; Cancer Research, vol. 68, No. 11, Jun. 1, 2008, pp. 4398-4405.
Park, Catherine C. et al.: "$\beta_1$ *Integrin Inhibitory Antibody Induces Apoptosis of Breast Cancer Cells, Inhibits Growth, and Distinguishes Malignant from Normal Phenotype in Three Dimensional Cultures and in vivo*"; Caner Research, vol. 66, No. 3, Jan. 1, 2006, pp. 1526-1535.
Supplementary European Search Report dated Sep. 12, 2016, regarding EP 13 86 7136.7.
Roitt et al.: "*Advances in Immunology*" The Immune System, New England J. M., Jul. 13, 2000, vol. 343:2, pp. 108-117. (English equivalent of Roitt, I.: "*Immunology*"; 2000, Moscow, Mir, 592 pages, p. 97.).
Russian Office Action dated May 4, 2017, regarding RU 2015130626.
Chan et al.: "*Human recombinant antibodies specific for hepatitis C virus core and envelope E2 peptides from an immune phage display library*"; Journal of General Virology, (1996), 77, pp. 2531-2539.
Japanese Office Action dated Oct. 26, 2017, regarding JP 2015-550754.
Juul, Lars et al.: "*A new apparently functional IGVK gene (VkLa) present in some individuals only*"; Immunogenetics, (1998), 48: 40-46.
Lenter M. et al. "*A monoclonal antibody against an activation epitope on mouse integrin chain beta 1 blocks adhesion of lymphocytes to the endothelial integrin alpha 6 beta 1*"; Proceedings of the National Academy of Sciences, 1993, 90(19): 9051-9055.
Russian Office Action dated Sep. 21, 2017, regarding RU 2015130626.

\* cited by examiner

Hybridoma OS2966 Heavy Chain Sequence

```
          10         20         30         40         50         60         70         80         90        100
GAAGTCCAGCTGCAGCTGCAGCAGTCTGGGCCTGAGCTGGTTGGGAGGCCTGGAGGCTTCAGTCAAGATTTCTTGCAAGGCTTCTGGCTACACCTTTACCGGGTACATTT
 E  V  Q  L  Q  Q  S  G  P  E  L  V  G  R  P  G  S  S  V  K  I  S  C  K  A  S  G  Y  T  F  T  G  Y  I
                         10                         20                         30
         110        120        130        140        150        160        170        180        190        200
TGAGCTGGGTGAAGCAGAGTCCTGGACAGGGGCTGGAATGGATTGGATAGGATATGGAATATCCTGAATATGGGTTGATCCTGAATATGGTACTACTGATTCTGCTGAGAAGTTCAAAAAGAG
 L  S  W  V  K  Q  S  P  G  Q  G  L  E  W  I  G  W  V  D  P  E  Y  G  S  T  D  S  A  E  K  F  K  K  R
                 40                          50  52                         60
                                                  A                                  A
                                                                                     B
                                                                                     C
         210        220        230        240        250        260        270        280        290        300
GGCCACACTGACTGCAGATATCCTCCAACACAGCCTACATCDAGCTTAGCAGCCTGACATCTGAGGACACAGCCACCTATTTTGTACTAGATATTAT
 A  T  L  T  A  D  I  S  S  N  T  A  Y  I  Q  L  S  S  L  T  S  E  D  T  A  T  Y  F  C  T  R  Y  Y
         70                          80                          A  B  C
                                         82
         310        320        330        340        350        360
GATGGTTATTATCGCCGGTGGTTTGCTTACTGGGGCCAAGGCACTCTGGTCACTGTCTCTTCA
 D  G  Y  Y  R  R  W  F  A  Y  W  G  Q  G  T  L  V  T  V  S  A
         100 A  B  C  D                       110
```

CDR definitions and protein sequence numbering according to Kabat numbering system. CDR nucleotide and protein sequences are highlighted in bold.

SEQ ID NO:1 (nucleotide sequence)
SEQ ID NO:2 (amino acid sequence)

FIG. 1

Hybridoma OS2966 Light Chain Sequence

```
         10         20         30         40         50         60         70         80         90        100
GACATCCAGATGACAGACACAGTCTCCAGCTTCCCTGTCTGCATCTCTGGGAGACATTGTCTCCATCGAATGTCTTGCAAGTGAGGGCATTCCAATAATTTAG
 D  I  Q  M  T  Q  S  P  A  S  L  S  A  S  L  G  D  I  V  S  I  E  C  L  A  S  E  G  I  S  N  N  L
                   10                           20                               30
        110        120        130        140        150        160        170        180        190        200
CGTGGCATCAGCAGCAGAAGCCAGGGAAATCTCCTCAGCTCCTGATCTATGGTGGACATAGCTTACATGACGGGGTCCCATCACGGTTCAGTGGCAGTGGATC
 A  W  H  Q  Q  K  P  G  K  S  P  Q  L  L  I  Y  G  A  H  S  L  H  D  G  V  P  S  R  F  S  G  S  G  S
              40                                      50
        210        220        230        240        250        260        270        280        290        300
TGGCACAGTATTCTCTCAAGATCAGCGGCATGCAACCTGAAGATGAAGGGGTTTATTACTGTCAACAGGGTTACAAATATCCGATTCAGTTTGGAGGT
 G  T  Q  Y  S  L  K  I  S  G  M  Q  P  E  D  E  G  V  Y  Y  C  Q  Q  G  Y  K  Y  P  I  T  F  G  G
       70                    80             82                          90                         100
        310        320
GGGACCAAGCTGGAACTGAAA
 G  T  K  L  E  L  K
                106 A
```

CDR definitions and protein sequence numbering according to Kabat numbering system. CDR nucleotide and protein sequences are highlighted in bold.

FIG. 2

SEQ ID NO:3 (nucleotide sequence)
SEQ ID NO:4 (amino acid sequence)

Table 1: Hybidoma OS2966 V-Region Sequence Analysis[a]

|  | H Chain | L Chain |
|---|---|---|
| CDR 1 Length | 5aa | 11aa |
| CDR 2 Length | 17aa | 7aa |
| CDR 3 Length | 12aa | 9aa |

FIG. 3

CDRs of VH Region

GYILS (SEQ ID NO: 23)
WVDPEYGSTDSAEKFKK (SEQ ID NO: 24)
YYDGYYRRWFAY (SEQ ID NO: 25)

CDRs VL Region

LASEGISNNLA (SEQ ID NO: 26)
GAHSLHD (SEQ ID NO: 27)
QQGYKYPIT (SEQ ID NO: 28)

FIG. 4

>OCS02-VH1
GAGGTGCAGCTGGTGCAGTCCGGCCCCGAGGTGAAGAAGCCCGGCTCCTCCGTGAA
GATCTCCTGCAAGGCCTCCGGCTACACCTTCACCGGCTACATCCTGTCCTGGGTGAA
GCAGGCCCCCGGCCAGGGCCTGGAGTGGATCGGCTGGGTGGACCCCGAGTACGGCT
CCACCGACTCCGCCGAGAAGTTCAAGAAGCGCGCCACCCTGACCGCCGACATCTCC
ACCAACACCGCCTACATCCAGCTGTCCTCCCTGCGCTCCGAGGACACCGCCACCTAC
TTCTGCACCCGCTACTACGACGGCTACTACCGCCGCTGGTTCGCCTACTGGGGCCAG
GGCACCCTGGTGACCGTGTCCTCC (SEQ ID NO: 5)

>OCS02-VH1
EVQLVQSGPEVKKPGSSVKISCKASGYTFTGYILSWVKQAPGQGLEWIGWVDPEYGSTD
SAEKFKKRATLTADISTNTAYIQLSSLRSEDTATYFCTRYYDGYYRRWFAYWGQGTLVT
VSS (SEQ ID NO: 6)

FIG. 5

>OCS02-VH2
GAGGTGCAGCTGGTGCAGTCCGGCGCCGAGGTGAAGAAGCCCGGCTCCTCCGTGAA
GATCTCCTGCAAGGCCTCCGGCTACACCTTCACCGGCTACATCCTGTCCTGGGTGCG
CCAGGCCCCCGGCCAGGGCCTGGAGTGGATCGGCTGGGTGGACCCCGAGTACGGCT
CCACCGACTCCGCCGAGAAGTTCAAGAAGCGCGCCACCCTGACCGCCGACATCTCC
ACCAACACCGCCTACATCGAGCTGTCCTCCCTGCGCTCCGAGGACACCGCCACCTAC
TTCTGCACCCGCTACTACGACGGCTACTACCGCCGCTGGTTCGCCTACTGGGGCCAG
GGCACCCTGGTGACCGTGTCCTCC (SEQ ID NO: 7)

>OCS02-VH2
EVQLVQSGAEVKKPGSSVKISCKASGYTFTGYILSWVRQAPGQGLEWIGWVDPEYGST
DSAEKFKKRATLTADISTNTAYIELSSLRSEDTATYFCTRYYDGYYRRWFAYWGQGTLV
TVSS (SEQ ID NO: 8)

FIG. 6

>OCS02-VH3
GAGGTGCAGCTGGTGCAGTCCGGCGCCGAGGTGAAGAAGCCCGGCTCCTCCGTGAA
GATCTCCTGCAAGGCCTCCGGCTACACCTTCACCGGCTACATCCTGTCCTGGGTGCG
CCAGGCCCCCGGCCAGGGCCTGGAGTGGATCGGCTGGGTGGACCCCGAGTACGGCT
CCACCGACTCCGCCGAGAAGTTCAAGAAGCGCGCCACCCTGACCGCCGACATCTCC
ACCTCCACCGCCTACATCGAGCTGTCCTCCCTGCGCTCCGAGGACACCGCCACCTAC
TTCTGCACCCGCTACTACGACGGCTACTACCGCCGCTGGTTCGCCTACTGGGGCCAG
GGCACCCTGGTGACCGTGTCCTCC (SEQ ID NO: 9)

>OCS02-VH3
EVQLVQSGAEVKKPGSSVKISCKASGYTFTGYILSWVRQAPGQGLEWIGWVDPEYGST
DSAEKFKKRATLTADISTSTAYIELSSLRSEDTATYFCTRYYDGYYRRWFAYWGQGTLV
TVSS (SEQ ID NO: 10)

FIG. 7

>OCS02-VH4
GAGGTGCAGCTGGTGCAGTCCGGCGCCGAGGTGAAGAAGCCCGGCTCCTCCGTGAA
GGTGTCCTGCAAGGCCTCCGGCTACACCTTCACCGGCTACATCCTGTCCTGGGTGCG
CCAGGCCCCCGGCCAGGGCCTGGAGTGGATCGGCTGGGTGGACCCCGAGTACGGCT
CCACCGACTCCGCCGAGAAGTTCAAGAAGCGCGCCACCATCACCGCCGACATCTCC
ACCTCCACCGCCTACATGGAGCTGTCCTCCCTGCGCTCCGAGGACACCGCCACCTAC
TTCTGCACCCGCTACTACGACGGCTACTACCGCCGCTGGTTCGCCTACTGGGGCCAG
GGCACCCTGGTGACCGTGTCCTCC (SEQ ID NO: 11)

>OCS02-VH4
EVQLVQSGAEVKKPGSSVKVSCKASGYTFT<u>GYILS</u>WVRQAPGQGLEWIG<u>WVDPEYGST
DSAEKFKK</u>RATITADISTSTAYMELSSLRSEDTATYFCTR<u>YYDGYYRRWFAY</u>WGQGTL
VTVSS (SEQ ID NO: 12)

FIG. 8

>OCS02-VH5
GAGGTGCAGCTGGTGCAGTCCGGCGCCGAGGTGAAGAAGCCCGGCTCCTCCGTGAA
GGTGTCCTGCAAGGCCTCCGGCTACACCTTCACCGGCTACATCCTGTCCTGGGTGCG
CCAGGCCCCCGGCCAGGGCCTGGAGTGGATCGGCTGGGTGGACCCCGAGTACGGCT
CCACCGACTCCGCCGAGAAGTTCAAGAAGCGCGTGACCATCACCGCCGACATCTCC
ACCTCCACCGCCTACATGGAGCTGTCCTCCCTGCGCTCCGAGGACACCGCCACCTAC
TTCTGCACCCGCTACTACGACGGCTACTACCGCCGCTGGTTCGCCTACTGGGGCCAG
GGCACCCTGGTGACCGTGTCCTCC (SEQ ID NO: 13)

>OCS02-VH5
EVQLVQSGAEVKKPGSSVKVSCKASGYTFT<u>GYILS</u>WVRQAPGQGLEWIG<u>WVDPEYGST
DSAEKFKK</u>RVTITADISTSTAYMELSSLRSEDTATYFCTR<u>YYDGYYRRWFAY</u>WGQGTL
VTVSS (SEQ ID NO: 14)

FIG. 9

>OCS02-VK1
GACATCCAGATGACCCAGTCCCCCTCCTCCCTGTCCGCCTCCGTGGGCGACCGCGTG
ACCATCACCTGCCTGGCCTCCGAGGGCATCTCCAACAACCTGGCCTGGCACCAGCAG
AAGCCCGGCAAGGCCCCCCAGCTGCTGATCTACGGCGCCCACTCCCTGCACGACGG
CGTGCCCGACCGCTTCTCCGGCTCCGGCTCCGGCACCGACTACACCCTGAAGATCTC
CGGCATGCAGCCCGAGGACGAGGGCGTGTACTACTGCCAGCAGGGCTACAAGTACC
CCATCACCTTCGGCGGCGGCACCAAGGTGGAGATCAAG (SEQ ID NO: 15)

>OCS02-Vk1
DIQMTQSPSSLSASVGDRVTITC<u>LASEGISNNLA</u>WHQQKPGKAPQLLIY<u>GAHSLHD</u>GVPD
RFSGSGSGTDYTLKISGMQPEDEGVYYC<u>QQGYKYPIT</u>FGGGTKVEIK (SEQ ID NO: 16)

FIG. 10

>OCS02-Vk2
GACATCCAGATGACCCAGTCCCCCTCCTCCCTGTCCGCCTCCGTGGGCGACCGCGTG
ACCATCACCTGCCTGGCCTCCGAGGGCATCTCCAACAACCTGGCCTGGCACCAGCAG
AAGCCCGGCAAGGCCCCCAAGCTGCTGATCTACGGCGCCCACTCCCTGCACGACGG
CGTGCCCGACCGCTTCTCCGGCTCCGGCTCCGGCACCGACTACACCCTGAAGATCTC
CCGCGTGGAGGCCGAGGACGTGGGCGTGTACTACTGCCAGCAGGGCTACAAGTACC
CCATCACCTTCGGCGGCGGCACCAAGGTGGAGATCAAG (SEQ ID NO: 17)

>OCS02-Vk2
DIQMTQSPSSLSASVGDRVTITCLASEGISNNLAWHQQKPGKAPKLLIYGAHSLHDGVPD
RFSGSGSGTDYTLKISRVEAEDVGVYYCQQGYKYPITFGGGTKVEIK (SEQ ID NO: 18)

FIG. 11

>OCS02-Vk3
GACATCCAGATGACCCAGTCCCCCTCCTCCCTGTCCGCCTCCGTGGGCGACCGCGTG
ACCATCACCTGCCTGGCCTCCGAGGGCATCTCCAACAACCTGGCCTGGTACCAGCAG
AAGCCCGGCAAGGCCCCCAAGCTGCTGATCTACGGCGCCCACTCCCTGCACGACGG
CGTGCCCGACCGCTTCTCCGGCTCCGGCTCCGGCACCGACTACACCCTGAAGATCTC
CCGCGTGGAGGCCGAGGACGTGGGCGTGTACTACTGCCAGCAGGGCTACAAGTACC
CCATCACCTTCGGCGGCGGCACCAAGGTGGAGATCAAG (SEQ ID NO: 19)

>OCS02-Vk3
DIQMTQSPSSLSASVGDRVTITCLASEGISNNLAWYQQKPGKAPKLLIYGAHSLHDGVPD
RFSGSGSGTDYTLKISRVEAEDVGVYYCQQGYKYPITFGGGTKVEIK (SEQ ID NO: 20)

FIG. 12

>OCS02-Vk4
GACATCCAGATGACCCAGTCCCCCTCCTCCCTGTCCGCCTCCGTGGGCGACCGCGTG
ACCATCACCTGCCTGGCCTCCGAGGGCATCTCCAACAACCTGGCCTGGTACCAGCAG
AAGCCCGGCAAGGCCCCCAAGCTGCTGATCTACGGCGCCCACTCCCTGCACGACGG
CGTGCCCGACCGCTTCTCCGGCTCCGGCTCCGGCACCGACTTCACCCTGAAGATCTC
CCGCGTGGAGGCCGAGGACGTGGGCGTGTACTACTGCCAGCAGGGCTACAAGTACC
CCATCACCTTCGGCGGCGGCACCAAGGTGGAGATCAAG (SEQ ID NO: 21)

>OCS02-Vk4
DIQMTQSPSSLSASVGDRVTITCLASEGISNNLAWYQQKPGKAPKLLIYGAHSLHDGVPD
RFSGSGSGTDFTLKISRVEAEDVGVYYCQQGYKYPITFGGGTKVEIK (SEQ ID NO: 22)

1-15 Composite Human Antibody VH Designs (Blank in sequence design = same residues as OS2966 sequence)

| aa pos. | Kabat | OS2966 Sequence - SEQ ID NO:2 | potentially critical residues | Variant 1 | Variant 2 | Variant 3 | Variant 4 | Variant 5 | Variant 6 | Variant 7 |
|---|---|---|---|---|---|---|---|---|---|---|
| 1 | 1 | E | c | E | E | E | E | E | E | E |
| 2 | 2 | V | | | | | | | | |
| 3 | 3 | Q | | | | | | | | |
| 4 | 4 | L | | | | | | | | |
| 5 | 5 | Q | | V | V | V | V | V | V | V |
| 6 | 6 | Q | | | | | | | | |
| 7 | 7 | S | | | | | | | | |
| 8 | 8 | G | | | | | | | | |
| 9 | 9 | P | | P | A | A | A | A | P | A |
| 10 | 10 | E | | | | | | | | |
| 11 | 11 | V | | | | | | | | |
| 12 | 12 | G | | K | K | K | K | K | K | K |
| 13 | 13 | R | | K | K | K | K | K | K | K |
| 14 | 14 | P | | | | | | | | |
| 15 | 15 | G | | | | | | | | |
| 16 | 16 | S | | | | | | | A | A |
| 17 | 17 | S | | | | | | | | |
| 18 | 18 | V | | | | | | | | |
| 19 | 19 | K | | | | | | | | |
| 20 | 20 | I | | I | I | I | V | V | I | I |
| 21 | 21 | S | | | | | | | | |
| 22 | 22 | C | | | | | | | | |
| 23 | 23 | K | | | | | | | | |
| 24 | 24 | A | | | | | | | | |
| 25 | 25 | S | | | | | | | | |
| 26 | 26 | G | | | | | | | | |
| 27 | 27 | Y | | | | | | | | |
| 28 | 28 | T | | | | | | | | |
| 29 | 29 | F | | | | | | | | |
| 30 | 30 | T | | | | | | | | |
| 31 | 31 | G | | | | | | | | |
| 32 | 32 | Y | | | | | | | | |
| 33 | 33 | I | | | | | | | | |
| 34 | 34 | L | | | | | | | | |
| 35 | 35 | S | | | | | | | | |
| 36 | 36 | W | | | | | | | | |
| 37 | 37 | V | | | | | | | | |
| 38 | 38 | K | | K | R | R | R | R | K | R |
| 39 | 39 | Q | | | | | | | | |
| 40 | 40 | S | | A | A | A | A | A | A | A |
| 41 | 41 | P | | | | | | | | |
| 42 | 42 | G | | | | | | | | |
| 43 | 43 | Q | | | | | | | | K | K |
| 44 | 44 | G | | | | | | | | |
| 45 | 45 | L | | | | | | | | |
| 46 | 46 | E | | | | | | | | |
| 47 | 47 | W | | | | | | | | |
| 48 | 48 | I | c | I | I | I | I | I | I | I |
| 49 | 49 | G | | | | | | | | |
| 50 | 50 | W | | | | | | | | |
| 51 | 51 | V | | | | | | | | |
| 52 | 52 | D | | | | | | | | |
| 53 | 53 | P | | | | | | | | |
| 54 | 56A | E | | | | | | | | |
| 55 | 54 | Y | | | | | | | | |
| 56 | 55 | G | | | | | | | | |
| 57 | 56 | S | | | | | | | | |

FIG. 15-1 (CONT.)

| aa pos. | Kabat | OS2966 Sequence - SEQ ID NO:2 | Variant 8 | Variant 9 | Variant 10 | Variant 11 | Variant 12 | Variant 13 | Variant 14 | Variant 15 |
|---|---|---|---|---|---|---|---|---|---|---|
| 1 | 1 | E | E | E | E | E | E | E | E | E |
| 2 | 2 | V | | | | | | | | |
| 3 | 3 | Q | | | | | | | | |
| 4 | 4 | L | | | | | | | | |
| 5 | 5 | Q | V | V | V | V | V | V | V | V |
| 6 | 6 | Q | | | | | | | | |
| 7 | 7 | S | | | | | | | | |
| 8 | 8 | G | | | | | | | | |
| 9 | 9 | P | A | A | A | P | A | A | A | A |
| 10 | 10 | E | | | | | | | | |
| 11 | 11 | V | | | | | | | | |
| 12 | 12 | G | K | K | K | K | K | K | K | K |
| 13 | 13 | R | K | K | K | K | K | K | K | K |
| 14 | 14 | P | | | | | | | | |
| 15 | 15 | G | | | | | | | | |
| 16 | 16 | S | A | A | A | A | A | A | A | A |
| 17 | 17 | S | | | | | | | | |
| 18 | 18 | V | | | | | | | | |
| 19 | 19 | K | | | | | | | | |
| 20 | 20 | I | I | V | V | I | I | V | V | V |
| 21 | 21 | S | | | | | | | | |
| 22 | 22 | C | | | | | | | | |
| 23 | 23 | K | | | | | | | | |
| 24 | 24 | A | | | | A | A | A | A | V |
| 25 | 25 | S | | | | | | | | |
| 26 | 26 | G | | | | | | | | |
| 27 | 27 | Y | | | | | | | | |
| 28 | 28 | T | | | | | | | | |
| 29 | 29 | F | | | | | | | | |
| 30 | 30 | T | | | | | | | | |
| 31 | 31 | G | | | | | | | | |
| 32 | 32 | Y | | | | | | | | |
| 33 | 33 | I | | | | | | | | |
| 34 | 34 | L | | | | | | | | |
| 35 | 35 | S | | | | | | | | |
| 36 | 36 | W | | | | | | | | |
| 37 | 37 | V | | | | | | | | |
| 38 | 38 | K | R | R | R | K | R | K | K | K |
| 39 | 39 | Q | | | | | | | | |
| 40 | 40 | S | A | A | A | A | A | A | A | A |
| 41 | 41 | P | | | | | | | | |
| 42 | 42 | G | | | | | | | | |
| 43 | 43 | Q | K | K | K | K | K | K | K | K |
| 44 | 44 | G | | | | | | | | |
| 45 | 45 | L | | | | | | | | |
| 46 | 46 | E | | | | | | | | |
| 47 | 47 | W | | | | | | | | |
| 48 | 48 | I | I | I | I | I | I | I | I | I |
| 49 | 49 | G | | | | | | | | |
| 50 | 50 | W | | | | | | | | |
| 51 | 51 | V | | | | | | | | |
| 52 | 52 | D | | | | | | | | |
| 53 | 53 | P | | | | | | | | |
| 54 | 56A | E | | | | | | | | |
| 55 | 54 | Y | | | | | | | | |
| 56 | 55 | G | | | | | | | | |
| 57 | 56 | S | | | | | | | | |

FIG. 15-1 (CONT.)

16-20 CDR-grafted humanized antibody designs - VH2, VH4 etc = acceptor human V region subgroup, J2, J4 etc = acceptor human J region

| aa pos. | Kabat | OS2966 Sequence - SEQ ID NO:2 | VH2 | Variant 16 | VH4 | Variant 17 | VH5 | Variant 15 | VH6 | Variant 19 | VH7 | Variant 20 | OS2956 Sequence |
|---|---|---|---|---|---|---|---|---|---|---|---|---|---|
| 1 | 1 | E | Q | E | Q | E | - | E | Q | E | Q | E | E |
| 2 | 2 | V | . | . | . | . | . | . | . | . | . | . | V |
| 3 | 3 | Q | . | . | . | . | . | . | . | . | . | . | Q |
| 4 | 4 | L | . | . | . | . | . | . | . | . | . | . | L |
| 5 | 5 | Q | . | . | . | . | V | V | . | . | V | V | Q |
| 6 | 6 | Q | E | Q | . | . | . | . | . | . | . | . | Q |
| 7 | 7 | S | . | . | W | W | . | . | . | . | . | . | S |
| 8 | 8 | G | . | . | . | . | . | . | . | . | . | . | G |
| 9 | 9 | P | . | . | A | A | A | A | . | . | S | S | P |
| 10 | 10 | E | G | G | G | G | . | . | G | G | . | . | E |
| 11 | 11 | V | L | L | L | L | . | . | L | L | L | L | V |
| 12 | 12 | G | V | . | L | L | K | K | V | . | K | K | G |
| 13 | 13 | R | K | . | K | K | K | K | K | . | K | K | R |
| 14 | 14 | P | . | . | . | . | . | . | . | . | . | . | P |
| 15 | 15 | G | . | . | . | . | G | . | . | . | . | . | G |
| 16 | 16 | S | S | . | S | . | E | E | S | . | A | . | S |
| 17 | 17 | S | E | . | E | . | . | . | Q | . | . | . | S |
| 18 | 18 | V | T | . | T | . | . | . | T | . | . | . | V |
| 19 | 19 | K | L | . | L | . | . | L | L | . | . | . | K |
| 20 | 20 | I | S | . | S | . | . | . | S | . | . | V | I |
| 21 | 21 | S | L | . | L | . | . | . | L | . | . | . | S |
| 22 | 22 | C | I | . | T | . | . | . | T | . | . | . | C |
| 23 | 23 | K | A | K | A | K | . | . | A | K | . | . | K |
| 24 | 24 | A | V | A | V | A | . | G | . | A | . | . | A |
| 25 | 25 | S | . | S | U | S | A | . | I | . | . | . | S |
| 26 | 26 | G | . | . | . | . | . | . | O | . | . | . | G |
| 27 | 27 | Y | D | . | G | . | . | . | D | . | . | . | Y |
| 28 | 28 | T | S | . | S | . | S | . | S | . | . | . | T |
| 29 | 29 | F | I | . | S | . | . | . | S | . | . | . | F |
| 30 | 30 | T | S | . | S | . | . | . | N | . | . | . | T |
| 31 | 31 | G | S | . | . | . | S | . | S | . | S | . | G |
| 32 | 32 | Y | G | . | . | . | Y | . | A | . | A | . | Y |
| 33 | 33 | I | N | . | Y | . | W | . | A | . | M | . | I |
| 34 | 34 | L | W | . | W | . | I | . | W | . | N | . | L |
| 35 | 35 | S | . | . | . | . | G | . | N | . | . | . | S |
| 36 | 36 | W | . | . | . | . | . | . | . | . | . | . | W |
| 37 | 37 | V | . | . | I | V | . | . | I | V | . | . | V |
| 38 | 38 | K | R | R | R | R | R | R | R | R | R | R | K |
| 39 | 39 | Q | . | . | . | . | . | . | . | . | . | . | Q |
| 40 | 40 | S | P | P | P | P | M | M | . | . | A | A | S |
| 41 | 41 | P | . | . | . | . | . | . | . | . | . | . | P |
| 42 | 42 | G | . | . | . | . | . | . | S | S | . | . | G |
| 43 | 43 | Q | K | K | K | K | K | K | R | R | . | . | Q |
| 44 | 44 | G | . | . | . | . | . | . | G | G | . | . | G |
| 45 | 45 | L | . | . | . | . | . | . | . | . | . | . | L |
| 46 | 46 | E | . | . | . | . | . | . | . | . | . | . | E |
| 47 | 47 | W | . | . | . | . | . | . | . | . | . | . | W |
| 48 | 48 | I | . | I | . | M | . | L | . | M | . | I | I |
| 49 | 49 | G | . | . | . | . | . | . | . | . | . | . | G |
| 50 | 50 | W | E | . | E | . | I | . | R | . | I | . | W |
| 51 | 51 | V | I | . | I | . | . | . | T | . | N | . | V |
| 52 | 52 | D | H | . | N | . | Y | . | Y | . | T | . | D |
| 53 | 53 | P | H | . | H | . | . | . | Y | . | N | . | P |
| 54 | 56A | E | . | . | . | . | G | . | S | . | T | . | E |
| 55 | 54 | Y | S | . | H | . | D | . | K | . | . | . | Y |
| 56 | 55 | G | G | . | S | . | S | . | W | . | N | . | G |
| 57 | 56 | S

FIG. 15-2

| # | # | AA | | | | | | | | | | |
|---|---|---|---|---|---|---|---|---|---|---|---|---|
| 58 | 57 | T | | | | | | | | | | |
| 59 | 58 | D | | | | | | | | | | |
| 60 | 59 | S | | | | | | | | | | |
| 61 | 60 | A | | | | | | | | | | |
| 62 | 61 | E | | | | | | | | | | |
| 63 | 62 | K | | | | | | | | | | |
| 64 | 63 | F | | | | | | | | | | |
| 65 | 64 | K | | | | | | | | | | |
| 66 | 65 | K | | | | | | | | | | |
| 67 | 66 | R | | | | | | | | | | |
| 68 | 67 | A | c | A | A | A | A | V | | A | A | A |
| 69 | 68 | T | c | L | L | L | I | I | | L | L | L |
| 70 | 69 | L | | | | | | | | A | A | A |
| 71 | 70 | T | | | | | | | | | | |
| 72 | 71 | A | | | | | | | | | | |
| 73 | 72 | D | c | I | I | I | I | I | | I | I | I |
| 74 | 73 | I | | | | | | | | | | |
| 75 | 74 | S | | T | T | T | T | T | | A | A | A |
| 76 | 75 | S | c | N | N | S | S | S | | N | N | S |
| 77 | 76 | N | | | | | | | | | | |
| 78 | 77 | T | | | | | | | | | | |
| 79 | 78 | A | | | | | | | | | | |
| 80 | 79 | Y | | | | | | | | | | |
| 81 | 80 | I | c | I | I | I | M | M | | I | I | I |
| 82 | 81 | Q | | Q | E | E | E | E | | Q | E | E |
| 83 | 82 | L | | | | | | | | | | |
| 84 | 82A | S | | | | | | | | | | |
| 85 | 82B | S | | | | | | | | | | |
| 86 | 82C | L | | | | | | | | | | |
| 87 | 83 | T | | R | R | R | R | R | | | | |
| 88 | 84 | S | | | | | | | | | | |
| 89 | 85 | E | | | | | | | | | | |
| 90 | 86 | D | | | | | | | | | | |
| 91 | 87 | T | | | | | | | | | | |
| 92 | 88 | A | | | | | | | | | | |
| 93 | 89 | T | c | T | T | T | T | T | T | T | T | T |
| 94 | 90 | Y | | | | | | | | | | |
| 95 | 91 | F | c | F | F | F | F | F | F | F | F | F |
| 96 | 92 | C | | | | | | | | | | |
| 97 | 93 | T | c | T | T | T | T | T | T | T | T | T |
| 98 | 94 | R | | | | | | | | | | |
| 99 | 95 | Y | | | | | | | | | | |
| 100 | 96 | Y | | | | | | | | | | |
| 101 | 97 | D | | | | | | | | | | |
| 102 | 98 | G | | | | | | | | | | |
| 103 | 99 | Y | | | | | | | | | | |
| 104 | 100 | Y | | | | | | | | | | |
| 105 | 100A | R | | | | | | | | | | |
| 106 | 100B | R | | | | | | | | | | |
| 107 | 100C | W | | | | | | | | | | |
| 108 | 100D | F | | | | | | | | | | |
| 109 | 101 | A | | | | | | | | | | |
| 110 | 102 | Y | | | | | | | | | | |
| 111 | 103 | W | | | | | | | | | | |
| 112 | 104 | G | | . | . | . | . | . | | . | . | . |
| 113 | 105 | Q | | . | . | . | . | . | | . | . | . |
| 114 | 106 | G | | . | . | . | . | . | | . | . | . |
| 115 | 107 | T | | . | . | . | . | . | | . | . | . |
| 116 | 108 | L | | . | . | . | . | . | | . | . | . |
| 117 | 109 | V | | . | . | . | . | . | | . | . | . |
| 118 | 110 | T | | . | . | . | . | . | | . | . | . |
| 119 | 111 | V | | | | | | | | | | |
| 120 | 112 | S | | | | | | | | | | |
| 121 | 113 | S | | | | | | | | | | |

Full length V region percentage homology to mAb

| | total=10 differences | 95.40% 6 | 92.56% 9

FIG. 15-2 (CONT.)

| Pos1 | Pos2 | Seq | | | | | | | |
|---|---|---|---|---|---|---|---|---|---|
| 58 | 57 | T | | | | | | | |
| 59 | 58 | D | | | | | | | |
| 60 | 59 | S | | | | | | | |
| 61 | 60 | A | | | | | | | |
| 62 | 61 | E | | | | | | | |
| 63 | 62 | K | | | | | | | |
| 64 | 63 | F | | | | | | | |
| 65 | 64 | K | | | | | | | |
| 66 | 65 | K | | | | | | | |
| 67 | 66 | R | A | V | A | A | A | A | F |
| 68 | 67 | A | | | L | L | L | | |
| 69 | 68 | T | I | I | L | L | L | I | I |
| 70 | 69 | L | | | | | | | |
| 71 | 70 | T | A | A | A | A | A | A | A |
| 72 | 71 | A | I | I | I | I | I | I | I |
| 73 | 72 | D | | | | | | | |
| 74 | 73 | I | | | | | | | |
| 75 | 74 | S | A | A | K | K | K | K | K |
| 76 | 75 | S | S | S | | | | | |
| 77 | 76 | N | | | | | | | |
| 78 | 77 | T | | | A | A | A | A | A |
| 79 | 78 | A | | | | | | | |
| 80 | 79 | Y | M | M | I | I | I | L | L |
| 81 | 80 | I | E | E | | | | | |
| 82 | 81 | Q | | | L | L | L | L | M |
| 83 | 82 | L | N | N | N | N | N | | N |
| 84 | 82A | S | | | | | | | |
| 85 | 82B | S | | | | | | | |
| 86 | 82C | L | | | | | | | |
| 87 | 83 | T | | | A | A | A | A | A |
| 88 | 84 | S | | | | | | | |
| 89 | 85 | E | | | | | | | |
| 90 | 86 | D | | | | | | | |
| 91 | 87 | T | | | | | | | |
| 92 | 88 | A | T | T | T | T | T | T | T |
| 93 | 89 | T | | | | | | | |
| 94 | 90 | Y | F | F | F | F | F | F | F |
| 95 | 91 | F | | | | | | | |
| 96 | 92 | C | T | T | T | T | T | T | T |
| 97 | 93 | R | | | | | | | |
| 98 | 94 | R | | | | | | | |
| 99 | 95 | Y | | | | | | | |
| 100 | 96 | Y | | | | | | | |
| 101 | 97 | D | | | | | | | |
| 102 | 98 | G | | | | | | | |
| 103 | 99 | Y | | | | | | | |
| 104 | 100 | R | | | | | | | |
| 105 | 100A | R | | | | | | | |
| 106 | 100B | W | | | | | | | |
| 107 | 100C | F | | | | | | | |
| 108 | 100D | A | | | | | | | |
| 109 | 101 | Y | | | | | | | |
| 110 | 102 | W | | | | | | | |
| 111 | 103 | G | | | | | | | |
| 112 | 104 | Q | | | | | | | |
| 113 | 105 | G | | | | | | | |
| 114 | 106 | T | | | | | | | |
| 115 | 107 | L | | | | | | | |
| 116 | 108 | V | | | | | | | |
| 117 | 109 | T | | | | | | | |
| 118 | 110 | V | | | | | | | |
| 119 | 111 | S | | | | | | | |
| 120 | 112 | S | | | | | | | |
| 121 | 113 | | | | | | | | |

Full length V region percentage homology to mAb

| 88.43% | 87.60% | 92.56% | 90.91% | 90.08% | 88.43% | 85.95% |
|---|---|---|---|---|---|---|
| 14 | 15 | 9 | 11 | 12 | 14 | 17 |

J Regions - VH

| J1 | J2 | J3 | J4 | J5 | J6 |
|----|----|----|----|----|----|
| A  | Y  |    |    |    | Y  |
| E  | W  |    |    | N  | Y  |
| Y  | Y  | A  | Y  | W  | G  |
| F  | F  | F  | F  | F  | M  |
| Q  | D  | D  | D  | D  | D  |
| H  | L  | V  | Y  | S  | V  |
| W  | W  | W  | W  | W  | W  |
| G  | G  | G  | G  | G  | G  |
| Q  | R  | Q  | Q  | Q  | Q  |
| G  | G  | G  | G  | G  | G  |
| T  | T  | T  | T  | T  | T  |
| L  | L  | M  | L  | L  | T  |
| V  | V  | V  | V  | V  | V  |
| T  | T  | T  | T  | T  | T  |
| V  | V  | V  | V  | V  | V  |
| S  | S  | S  | S  | S  | S  |
| S  | S  | S  | S  | S  | S  |

1-13 Composite Human Antibody Vk Designs (Blank in sequence design - same residues as OS2966 sequence)

| aa pos. | Kabat | OS2966 Sequence - SEQ ID NO:4 | potentially critical residues | Variant 1 | Variant 2 | Variant 3 | Variant 4 | Variant 5 | Variant 6 | Variant 7 |
|---|---|---|---|---|---|---|---|---|---|---|
| 1 | 1 | D | | | | | | | | |
| 2 | 2 | I | | | | | | | | |
| 3 | 3 | Q | | | | | | Q | Q | V |
| 4 | 4 | M | | | | | | | | |
| 5 | 5 | T | | | | | | | | |
| 6 | 6 | Q | | | | | | | | |
| 7 | 7 | S | | | | | | | | |
| 8 | 8 | P | | | | | | | | |
| 9 | 9 | A | | S | S | S | S | D | D | D |
| 10 | 10 | S | | | | | | | | |
| 11 | 11 | L | | | | | | | | |
| 12 | 12 | S | | | | | | | | |
| 13 | 13 | A | | | | | | | | |
| 14 | 14 | S | | | | | | | | |
| 15 | 15 | L | | V | V | V | V | | | |
| 16 | 16 | G | | | | | | | | |
| 17 | 17 | D | | | | | | | | |
| 18 | 18 | I | | R | R | R | R | R | R | R |
| 19 | 19 | V | | | | | | A | A | A |
| 20 | 20 | S | | T | T | T | T | T | T | T |
| 21 | 21 | I | | | | | | | | |
| 22 | 22 | E | | T | T | T | T | N | N | N |
| 23 | 23 | C | | | | | | | | |
| 24 | 24 | L | | | | | | | | |
| 25 | 25 | A | | | | | | | | |
| 26 | 26 | S | | | | | | | | |
| 27 | 27 | E | | | | | | | | |
| 28 | 28 | G | | | | | | | | |
| 29 | 29 | I | | | | | | | | |
| 30 | 30 | S | | | | | | | | |
| 31 | 31 | N | | | | | | | | |
| 32 | 32 | N | | | | | | | | |
| 33 | 33 | L | | | | | | | | |
| 34 | 34 | A | | | | | | | | |
| 35 | 35 | W | | | | | | | | |
| 36 | 36 | H | c | H | H | Y | Y | H | H | H |
| 37 | 37 | Q | | | | | | | | |
| 38 | 38 | Q | | | | | | | | |
| 39 | 39 | K | | | | | | | | |
| 40 | 40 | P | | | | | | | | |
| 41 | 41 | G | | | | | | | | |
| 42 | 42 | K | | | | | | | | |
| 43 | 43 | S | | A | A | A | A | Q | Q | Q |
| 44 | 44 | P | | | | | | | | |
| 45 | 45 | Q | | Q | K | K | K | Q | R | R |
| 46 | 46 | L | | | | | | | | |
| 47 | 47 | L | | | | | | | | |
| 48 | 48 | I | | | | | | | | |
| 49 | 49 | Y | | | | | | | | |
| 50 | 50 | G | | | | | | | | |
| 51 | 51 | A | | | | | | | | |
| 52 | 52 | H | | | | | | | | |
| 53 | 53 | S | | | | | | | | |
| 54 | 54 | L | | | | | | | | |
| 55 | 55 | H | | | | | | | | |
| 56 | 56 | D | | | | | | | | |

FIG. 17-1 (CONT.)

| aa pos. | Kabat | OS2966 Sequence - SEQ ID NO:4 | Variant 8 | Variant 9 | Variant 10 | Variant 11 | Variant 12 | Variant 13 |
|---|---|---|---|---|---|---|---|---|
| 1 | 1 | D | | D | D | D | E | E |
| 2 | 2 | I | | | | | | |
| 3 | 3 | Q | V | Q | Q | Q | Q | V |
| 4 | 4 | M | | | | | | |
| 5 | 5 | T | | | | | | |
| 6 | 6 | Q | | | | | | |
| 7 | 7 | S | | | | | | |
| 8 | 8 | P | | | | | | |
| 9 | 9 | A | D | | | | | |
| 10 | 10 | S | | S | S | T | T | T |
| 11 | 11 | L | | | | | | |
| 12 | 12 | S | | | | | | |
| 13 | 13 | A | | | | | | |
| 14 | 14 | S | | | | | | |
| 15 | 15 | L | | | | | | |
| 16 | 16 | G | | | | | | |
| 17 | 17 | D | | | | | | |
| 18 | 18 | I | R | | | | | |
| 19 | 19 | V | A | | | | | |
| 20 | 20 | S | T | | | | | |
| 21 | 21 | I | | | | | | |
| 22 | 22 | E | N | | | | | |
| 23 | 23 | C | | | | | | |
| 24 | 24 | L | | | | | | |
| 25 | 25 | A | | | | | | |
| 26 | 26 | S | | | | | | |
| 27 | 27 | E | | | | | | |
| 28 | 28 | G | | | | | | |
| 29 | 29 | I | | | | | | |
| 30 | 30 | S | | | | | | |
| 31 | 31 | N | | | | | | |
| 32 | 32 | N | | | | | | |
| 33 | 33 | L | | | | | | |
| 34 | 34 | A | | | | | | |
| 35 | 35 | W | | | | | | |
| 36 | 36 | H | Y | H | H | H | H | Y |
| 37 | 37 | Q | | | | | | |
| 38 | 38 | Q | | | | | | |
| 39 | 39 | K | | | | | | |
| 40 | 40 | P | | | | | | |
| 41 | 41 | G | | | | | | |
| 42 | 42 | K | Q | Q | Q | Q | Q | Q |
| 43 | 43 | S | | | | | | |
| 44 | 44 | P | | | | | | |
| 45 | 45 | Q | R | Q | R | R | R | R |
| 46 | 46 | L | | | | | | |
| 47 | 47 | L | | | | | | |
| 48 | 48 | I | | | | | | |
| 49 | 49 | Y | | | | | | |
| 50 | 50 | G | | | | | | |
| 51 | 51 | A | | | | | | |
| 52 | 52 | H | | | | | | |
| 53 | 53 | S | | | | | | |
| 54 | 54 | L | | | | | | |
| 55 | 55 | H | | | | | | |
| 56 | 56 | D | | | | | | |

FIG. 17-1 (CONT.)

14-18 CDR- grafted humanized antibody designs - VH2, VH4 etc = acceptor human V region subgroup, J1, J2 etc = acceptor human J region

| aa pos. | Kabat | OS2966 Sequence - SEQ ID NO:4 | VkI | Variant 14 | VkII | Variant 15 | VkIII | Variant 16 | VkIV | Variant 17 | VkVI | Variant 18 | OS2966 Sequence |
|---|---|---|---|---|---|---|---|---|---|---|---|---|---|
| 1 | 1 | D | V | V | - | - | E | E | - | - | - | - | D |
| 2 | 2 | I | - | - | V | V | - | - | - | - | V | V | I |
| 3 | 3 | Q | W | W | V | V | V | V | V | V | V | V | Q |
| 4 | 4 | M | - | - | - | - | L | M | - | - | - | - | M |
| 5 | 5 | T | - | - | - | - | - | - | - | - | - | - | T |
| 6 | 6 | Q | - | - | - | - | - | - | - | - | - | - | Q |
| 7 | 7 | S | - | - | - | - | - | - | - | - | - | - | S |
| 8 | 8 | P | - | - | - | - | - | - | - | - | - | - | P |
| 9 | 9 | A | S | S | L | L | G | G | D | D | - | - | A |
| 10 | 10 | S | L | L | - | - | T | T | - | - | F | F | S |
| 11 | 11 | L | - | - | - | - | - | - | - | - | - | - | L |
| 12 | 12 | S | - | - | P | P | - | - | A | A | - | - | S |
| 13 | 13 | A | - | - | V | V | L | L | V | V | V | V | A |
| 14 | 14 | S | - | - | T | T | - | - | - | - | T | T | S |
| 15 | 15 | L | T | T | - | - | P | P | - | - | P | P | L |
| 16 | 16 | G | - | - | - | - | - | - | - | - | - | - | G |
| 17 | 17 | D | - | - | Q | Q | E | E | E | E | E | E | D |
| 18 | 18 | I | R | R | P | P | R | R | R | R | K | K | I |
| 19 | 19 | V | - | - | A | - | A | A | A | A | A | A | V |
| 20 | 20 | S | T | T | - | - | T | T | T | T | - | - | S |
| 21 | 21 | I | - | - | - | - | L | - | - | - | - | - | I |
| 22 | 22 | E | S | S | S | S | S | S | N | N | T | T | E |
| 23 | 23 | C | - | - | - | - | - | - | - | - | - | - | C |
| 24 | 24 | L | R | - | R | - | R | - | K | - | - | Q | L |
| 25 | 25 | A | M | - | S | - | - | - | S | - | - | - | A |
| 26 | 26 | S | - | - | - | - | - | - | - | - | - | - | S |
| 27 | 27 | E | Q | - | Q | - | Q | - | Q | - | - | - | E |
| 28 | 28 | G | - | - | D | - | V | - | N | - | - | - | G |
| 29 | 29 | I | - | - | G | - | S | - | N | - | - | - | I |
| 30 | 30 | S | - | - | N | - | - | - | K | - | G | - | S |
| 31 | 31 | N | S | - | T | - | S | - | - | - | - | - | N |
| 32 | 32 | N | Y | - | Y | - | Y | - | Y | - | Y | - | N |
| 33 | 33 | L | - | - | L | - | - | - | - | - | L | - | L |
| 34 | 34 | A | - | - | N | - | - | - | - | - | - | - | A |
| 35 | 35 | W | - | - | - | - | - | - | - | - | - | - | W |
| 36 | 36 | H | Y | H | F | H | Y | H | Y | H | Y | H | H |
| 37 | 37 | Q | - | - | - | - | - | - | - | - | - | - | Q |
| 38 | 38 | Q | - | - | - | - | - | - | - | - | - | - | Q |
| 39 | 39 | K | - | - | R | R | - | - | - | - | - | - | K |
| 40 | 40 | P | - | - | - | - | - | - | - | - | - | - | P |
| 41 | 41 | G | - | - | - | - | - | - | - | - | D | D | G |
| 42 | 42 | K | - | - | Q | Q | Q | Q | Q | Q | Q | Q | K |
| 43 | 43 | S | A | A | - | - | A | A | - | - | A | A | S |
| 44 | 44 | P | - | - | P | P | P | P | - | - | - | - | P |
| 45 | 45 | Q | E | E | R | Q | Q | Q | K | Q | K | Q | Q |
| 46 | 46 | L | - | - | R | R | - | - | - | - | - | - | L |
| 47 | 47 | L | - | - | - | - | - | - | - | - | - | - | L |
| 48 | 48 | I | - | - | - | - | - | - | - | - | - | - | I |
| 49 | 49 | Y | - | - | - | - | - | - | - | - | Y | Y | Y |
| 50 | 50 | G | A | A | K | - | - | - | W | - | K | - | G |
| 51 | 51 | A | - | - | V | - | - | - | - | - | Y | - | A |
| 52 | 52 | H | S | S | S | - | S | S | S | S | S | S | H |
| 53 | 53 | S | - | - | N | - | R | - | T | - | Q | - | S |
| 54 | 54 | L | T | T | W | - | A | A | R | R | S | S | L |
| 55 | 55 | H | - | - | D | - | - | - | E | E | I | I | H |
| 56 | 56 | D | Q | Q | S | - | T | T | S | S | S | S | D |

FIG. 17-2 (CONT.)

| | | | | | | | | | | |
|---|---|---|---|---|---|---|---|---|---|---|
| 57 | 57 | G | | | | | | | | |
| 58 | 58 | V | | | | | | | | |
| 59 | 59 | P | | | | | | | | |
| 60 | 60 | S | D | D | D | D | | | | |
| 61 | 61 | R | | | | | | | | |
| 62 | 62 | F | | | | | | | | |
| 63 | 63 | S | | | | | | | | |
| 64 | 64 | G | | | | | | | | |
| 65 | 65 | S | | | | | | | | |
| 66 | 66 | G | | | | | | | | |
| 67 | 67 | S | | | | | | | | |
| 68 | 68 | G | | | | | | | | |
| 69 | 69 | T | | | | | | | | |
| 70 | 70 | Q | | D | D | D | D | F | F | F | F |
| 71 | 71 | Y | C | Y | Y | Y | F | Y | Y | Y | Y |
| 72 | 72 | S | | T | T | T | T | T | T | T | T |
| 73 | 73 | L | | | | | | | | |
| 74 | 74 | K | | | | | | | | |
| 75 | 75 | I | | | | | | | | |
| 76 | 76 | S | | | | | | | | |
| 77 | 77 | G | G | R | R | R | G | S | S | S |
| 78 | 78 | M | M | V | V | V | | | | |
| 79 | 79 | Q | Q | E | E | E | | | | |
| 80 | 80 | P | P | A | A | A | | | | |
| 81 | 81 | E | | | | | | | | |
| 82 | 82 | D | | | | | | | | |
| 83 | 83 | E | E | V | V | V | E | F | F | F |
| 84 | 84 | G | | | | | A | A | A | A |
| 85 | 85 | V | | | | | V | V | V | V |
| 86 | 86 | Y | | | | | | | | |
| 87 | 87 | Y | | | | | | | | |
| 88 | 88 | C | | | | | | | | |
| 89 | 89 | Q | | | | | | | | |
| 90 | 90 | Q | | | | | | | | |
| 91 | 91 | G | | | | | | | | |
| 92 | 92 | Y | | | | | | | | |
| 93 | 93 | K | | | | | | | | |
| 94 | 94 | Y | | | | | | | | |
| 95 | 95 | P | | | | | | | | |
| 96 | 96 | I | | | | | | | | |
| 97 | 97 | T | | | | | | | | |
| 98 | 98 | F | | | | | | | | |
| 99 | 99 | G | | | | | | | | |
| 100 | 100 | G | | | | | | | | |
| 101 | 101 | G | | | | | | | | |
| 102 | 102 | T | | | | | | | | |
| 103 | 103 | K | | | | | | | | |
| 104 | 104 | L | V | V | V | V | V | V | V | V |
| 105 | 105 | E | | | | | | | | |
| 106 | 106 | L | I | I | I | I | I | I | I | I |
| 107 | 106A | K | | | | | | | | |

Full length V region percentage homology to mAb: total=2 differences

| | 89.72% | 82.24% | 81.31% | 80.37% | 89.72% | 86.92% | 85.98% | 85.98% |
|---|---|---|---|---|---|---|---|---|
| | 11 | 19 | 20 | 21 | 11 | 14 | 15 | 15 |

FIG. 17-2 (CONT.)

| # | # | Seq | | | | | |
|---|---|---|---|---|---|---|---|
| 57 | 57 | G | | | | | |
| 58 | 58 | V | | | | | |
| 59 | 59 | P | | | | | |
| 60 | 60 | S | | | | | |
| 61 | 61 | R | | | | | |
| 62 | 62 | F | | | | | |
| 63 | 63 | S | | | | | |
| 64 | 64 | G | | | | | |
| 65 | 65 | S | | | | | |
| 66 | 66 | G | | | | | |
| 67 | 67 | S | | | | | |
| 68 | 68 | G | | | | | |
| 69 | 69 | T | | | | | |
| 70 | 70 | Q | D | D | D | D | D |
| 71 | 71 | Y | Y | Y | Y | Y | Y |
| 72 | 72 | S | T | T | T | T | T |
| 73 | 73 | L | | | | | |
| 74 | 74 | K | | | | | |
| 75 | 75 | I | | | | | |
| 76 | 76 | S | | | | | |
| 77 | 77 | G | G | R | R | R | R |
| 78 | 78 | M | M | V | V | V | V |
| 79 | 79 | Q | Q | E | E | E | E |
| 80 | 80 | P | P | P | A | A | A |
| 81 | 81 | E | | | | | |
| 82 | 82 | D | | | | | |
| 83 | 83 | E | E | V | V | V | V |
| 84 | 84 | G | | | | | |
| 85 | 85 | V | V | V | V | V | V |
| 86 | 86 | Y | | | | | |
| 87 | 87 | Y | | | | | |
| 88 | 88 | C | | | | | |
| 89 | 89 | Q | | | | | |
| 90 | 90 | Q | | | | | |
| 91 | 91 | G | | | | | |
| 92 | 92 | Y | | | | | |
| 93 | 93 | K | | | | | |
| 94 | 94 | Y | | | | | |
| 95 | 95 | P | | | | | |
| 96 | 96 | I | | | | | |
| 97 | 97 | T | | | | | |
| 98 | 98 | F | | | | | |
| 99 | 99 | G | | | | | |
| 100 | 100 | G | | | | | |
| 101 | 101 | G | | | | | |
| 102 | 102 | T | | | | | |
| 103 | 103 | K | | | | | |
| 104 | 104 | L | V | V | V | V | V |
| 105 | 105 | E | | | | | |
| 106 | 106 | L | I | I | I | I | I |
| 107 | 106A | K | | | | | |

| Full length V region percentage homology to mAb | 95.32% 5 | 90.65% 10 | 88.79% 12 | 87.

FIG. 17-2 (CONT.)

| # | # | mAb | | | | | | | | | | | mAb |
|---|---|---|---|---|---|---|---|---|---|---|---|---|---|
| 57 | 57 | G | - | - | - | - | - | - | - | - | - | - | G |
| 58 | 58 | V | - | - | - | - | I | - | - | - | - | - | V |
| 59 | 59 | P | - | - | - | - | - | - | - | - | - | - | P |
| 60 | 60 | S | - | - | D | D | D | D | D | D | - | - | S |
| 61 | 61 | R | - | - | - | - | - | - | - | - | - | - | R |
| 62 | 62 | F | - | - | - | - | - | - | - | - | - | - | F |
| 63 | 63 | S | - | - | - | - | - | - | - | - | - | - | S |
| 64 | 64 | G | - | - | - | - | - | - | - | - | - | - | G |
| 65 | 65 | S | - | - | - | - | - | - | - | - | - | - | S |
| 66 | 66 | G | - | - | - | - | - | - | - | - | - | - | G |
| 67 | 67 | S | - | - | - | - | - | - | - | - | - | - | S |
| 68 | 68 | G | - | - | - | - | - | - | - | - | - | - | G |
| 69 | 69 | T | - | - | - | - | - | - | - | - | - | - | T |
| 70 | 70 | Q | D | D | D | D | D | D | D | D | D | D | Q |
| 71 | 71 | Y | F | Y | F | Y | F | Y | F | Y | F | Y | Y |
| 72 | 72 | S | T | T | T | T | T | T | T | T | T | T | S |
| 73 | 73 | L | - | - | - | - | - | - | - | - | F | - | L |
| 74 | 74 | K | T | T | - | - | T | T | T | T | T | T | K |
| 75 | 75 | I | - | - | - | - | - | - | - | - | - | - | I |
| 76 | 76 | S | - | - | - | - | - | - | - | - | - | - | S |
| 77 | 77 | G | C | C | R | R | R | R | S | S | S | S | G |
| 78 | 78 | M | L | L | V | V | L | L | L | L | L | L | M |
| 79 | 79 | Q | - | - | E | E | E | E | - | - | E | E | Q |
| 80 | 80 | P | S | S | A | A | - | - | A | A | A | A | P |
| 81 | 81 | E | - | - | - | - | - | - | - | - | - | - | E |
| 82 | 82 | D | - | - | - | - | - | - | - | - | - | - | D |
| 83 | 83 | E | F | F | V | V | F | F | V | V | A | A | E |
| 84 | 84 | G | A | A | - | - | A | A | A | A | A | A | G |
| 85 | 85 | V | T | V | - | - | - | - | - | - | T | - | V |
| 86 | 86 | Y | - | - | - | - | - | - | - | - | - | - | Y |
| 87 | 87 | Y | - | - | - | - | - | - | - | - | - | - | Y |
| 88 | 88 | C | - | - | - | - | - | - | - | - | - | - | C |
| 89 | 89 | Q | - | - | M | - | - | - | - | - | - | - | Q |
| 90 | 90 | Q | - | - | - | - | - | - | - | - | - | - | Q |
| 91 | 91 | G | Y | - | - | - | Y | - | Y | - | - | - | G |
| 92 | 92 | Y | - | - | T | - | G | - | - | - | N | - | Y |
| 93 | 93 | K | S | - | H | - | S | - | S | - | - | - | K |
| 94 | 94 | Y | F | - | W | - | S | - | T | - | H | - | Y |
| 95 | 95 | P | - | - | - | - | - | - | - | - | - | - | P |
| 96 | 96 | I | - | - | - | - | - | - | - | - | - | - | I |
| 97 | 97 | T | - | - | - | - | - | - | - | - | - | - | T |
| 98 | 98 | F | - | - | - | - | - | - | - | - | - | - | F |
| 99 | 99 | G | - | - | - | - | - | - | - | - | - | - | G |
| 100 | 100 | G | Q | Q | Q | Q | P | P | - | - | - | - | G |
| 101 | 101 | G | - | - | - | - | - | - | - | - | - | - | G |
| 102 | 102 | T | - | - | - | - | - | - | - | - | - | - | T |
| 103 | 103 | K | - | - | - | - | - | - | - | - | - | - | K |
| 104 | 104 | L | V | V | - | - | V | V | V | V | V | V | L |
| 105 | 105 | E | - | - | - | - | D | D | - | - | - | - | E |
| 106 | 106 | L | I | I | I | I | I | I | I | I | I | I | L |
| 107 | 106A | K | - | - | - | - | - | - | - | - | - | - | K |
| | | | J1 | | J2 | | J3 | | J4 | | J4 | | |

Full length V region percentage homology to mAb

| 78.50% | 79.44% | 74.77% | 78.50% | 77.57% |
|---|---|---|---|---|
| 23 | 22 | 27 | 23 | 24 |

J Regions - Kappa Light Chains

| J1 | J2 | J3 | J4 | J5 |
|----|----|----|----|----|
| W | Y | F | L | I |
| T | T | T | T | T |
| F | F | F | F | F |
| G | G | G | G | G |
| Q | Q | P | G | Q |
| G | G | G | G | G |
| T | T | T | T | T |
| K | K | K | K | R |
| V | L | V | V | L |
| E | E | D | E | E |
| I | I | I | I | I |
| K | K | K | K | K |

FIG. 18

| | | | | | | | | | | |
|---|---|---|---|---|---|---|---|---|---|---|
| UUU | F | 0.44 | UCU | S | 0.20 | UAU | Y | 0.43 | UGU | C | 0.48 |
| UUC | F | 0.56 | UCC | S | 0.22 | UAC | Y | 0.57 | UGC | C | 0.52 |
| UUA | L | 0.07 | UCA | S | 0.14 | UAA | * | 0.28 | UGA | * | 0.49 |
| UUG | L | 0.13 | UCG | S | 0.05 | UAG | * | 0.23 | UGG | W | 1.00 |
| CUU | L | 0.13 | CCU | P | 0.31 | CAU | H | 0.41 | CGU | R | 0.08 |
| CUC | L | 0.20 | CCC | P | 0.30 | CAC | H | 0.59 | CGC | R | 0.17 |
| CUA | L | 0.08 | CCA | P | 0.29 | CAA | Q | 0.26 | CGA | R | 0.12 |
| CUG | L | 0.39 | CCG | P | 0.10 | CAG | Q | 0.74 | CGG | R | 0.19 |
| AUU | I | 0.34 | ACU | T | 0.25 | AAU | N | 0.43 | AGU | S | 0.15 |
| AUC | I | 0.50 | ACC | T | 0.35 | AAC | N | 0.57 | AGC | S | 0.24 |
| AUA | I | 0.16 | ACA | T | 0.29 | AAA | K | 0.39 | AGA | R | 0.22 |
| AUG | M | 1.00 | ACG | T | 0.10 | AAG | K | 0.61 | AGG | R | 0.22 |
| GUU | V | 0.17 | GCU | A | 0.29 | GAU | D | 0.45 | GGU | G | 0.18 |
| GUC | V | 0.25 | GCC | A | 0.38 | GAC | D | 0.55 | GGC | G | 0.33 |
| GUA | V | 0.12 | GCA | A | 0.23 | GAA | E | 0.41 | GGA | G | 0.26 |
| GUG | V | 0.46 | GCG | A | 0.09 | GAG | E | 0.59 | GGG | G | 0.23 |

FIG. 19

MDA-MB-231 (Human Triple Negative Breast Cancer)

AsPC-3 (Human Pancreatic Cancer)

PANC1-GEMR (Human Gemcitabine-Resistant Pancreatic Cancer)

PANC1-GEMR (Human Gemcitabine-Resistant Pancreatic Cancer)

|  | Chimeric | H3 | K20 | A33 | KLH |
|---|---|---|---|---|---|
| Donor 1 |  |  |  |  | P |
| Donor 2 |  |  | P |  |  |
| Donor 3 |  |  |  |  |  |
| Donor 4 |  |  | P |  |  |
| Donor 5 | P* |  | P |  | P |
| Donor 6 |  |  | P | P | P |
| Donor 7 | P |  | P | P | P |
| Donor 8 |  |  |  |  |  |
| Donor 9 |  |  |  |  |  |
| Donor 10 |  |  |  |  | P |
| Donor 11 |  |  | P | P | P |
| Donor 12 | P* |  | P | P | P |
| % | 25 | 0 | 58 | 33 | 58 |

SEQUENCE LISTING

<160> NUMBER OF SEQ ID NOS: 125

<210> SEQ ID NO 1
<211> LENGTH: 363
<212> TYPE: DNA
<213> ORGANISM: Artificial Sequence
<220> FEATURE:
<223> OTHER INFORMATION: Synthetic construct

<400> SEQUENCE: 1

```
gaagtccagc tgcagcagtc tgggcctgag gttgggaggc ctgggtcctc agtcaagatt      60
tcttgcaagg cttctggcta ccctttacc gggtacattt tgagctgggt gaagcagagt     120
cctggacagg gctggaatg dataggatgg ttgatcctg aatatggtag tactgattct      180
gctgagaagt tcaaaagag ggccacactg actgcagata tatcctccaa cacagcctac      240
atccagctta gcagcctgac atctgaggac acagccacct attttgtac tagatattat       300
gatggttatt atcgccggtg gtttgcttac tgggccaag gcactctggt cactgtctct      360
tca                                                                   363
```

<210> SEQ ID NO 2
<211> LENGTH: 121
<212> TYPE: PRT
<213> ORGANISM: Artificial Sequence
<220> FEATURE:
<223> OTHER INFORMATION: Synthetic construct

<400> SEQUENCE: 2

```
Glu Val Gln Leu Gln Gln Ser Gly Pro Glu Val Gly Arg Pro Gly Ser
1               5                   10                  15
Ser Val Lys Ile Ser Cys Lys Ala Ser Gly Tyr Thr Phe Thr Gly Tyr
            20                  25                  30
Ile Leu Ser Trp Val Lys Gln Ser Pro Gly Gln Gly Leu Glu Trp Ile
        35                  40                  45
Gly Trp Val Asp Pro Glu Tyr Gly Ser Thr Asp Ser Ala Glu Lys Phe
    50                  55                  60
Lys Lys Arg Ala Thr Leu Thr Ala Asp Ile Ser Ser Asn Thr Ala Tyr
65                  70                  75                  80
Ile Gln Leu Ser Ser Leu Thr Ser Glu Asp Thr Ala Thr Tyr Phe Cys
                85                  90                  95
Thr Arg Tyr Tyr Asp Gly Tyr Tyr Arg Arg Trp Phe Ala Tyr Trp Gly
            100                 105                 110
Gln Gly Thr Leu Val Thr Val Ser Ser
        115                 120
```

<210> SEQ ID NO 3
<211> LENGTH: 321
<212> TYPE: DNA
<213> ORGANISM: Artificial Sequence
<220> FEATURE:
<223> OTHER INFORMATION: Synthetic construct

<400> SEQUENCE: 3

```
gacatccaga tgacacagtc tccagcttcc ctgtctgcat ctctgggaga cattgtctcc      60
atcgaatgtc ttgcaagtga ggcatttcc aataatttag cgtggcatca gcagaagcca      120
gggaaatctc ctcagctcct gatctatggt gcacatagct acatgacgg ggtcccatca      180
cggttcagtg gcagtggatc tggcacacag tattctctca agatcagcgg catgcaacct      240
gaagatgaag gggtttatta ctgtcaacag ggttacaaat atccgatcac gtttggaggt      300
gggaccaagc tggaactgaa a                                               321
```

<210> SEQ ID NO 4
<211> LENGTH: 107
<212> TYPE: PRT

<213> ORGANISM: Artificial Sequence
<220> FEATURE:
<223> OTHER INFORMATION: Synthetic construct

<400> SEQUENCE: 4

Asp Ile Gln Met Thr Gln Ser Pro Ala Ser Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp His Gln Lys Pro Gly Lys Ser Pro Gln Leu Leu Ile
        35                  40                  45

Tyr Gly Ala His Ser Leu His Asp Gly Val Pro Ser Arg Phe Ser Gly
    50                  55                  60

Ser Gly Ser Gly Thr Gln Tyr Ser Leu Lys Ile Ser Gly Met Gln Pro
65                  70                  75                  80

Glu Asp Glu Gly Val Tyr Tyr Cys Gln Gln Gly Tyr Lys Tyr Pro Ile
                85                  90                  95

Thr Phe Gly Gly Gly Thr Lys Leu Glu Leu Lys
            100                 105

<210> SEQ ID NO 5
<211> LENGTH: 363
<212> TYPE: DNA
<213> ORGANISM: Artificial Sequence
<220> FEATURE:
<223> OTHER INFORMATION: Synthetic construct

<400> SEQUENCE: 5
gaggtgcagc tggtgcagtc cggccccgag gtgaagaagc ccggctcctc cgtgaagatc      60
tcctgcaagg cctccggcta caccttcacc ggctacatcc tgtcctgggt gaagcaggcc     120
cccggccagg gcctggagtg gatcggctgg gtggaccccg agtacggctc caccgactcc     180
gccgagaagt tcaagaagcg cgccacccta accgccgaca tctccaccaa caccgcctac     240
atccagctgt cctccctgcg ctccgaggac accgccacct acttctgcac cgctactac      300 gacggctact accgccgctg gttcgcctac tggggccagg gcaccctggt gaccgtgtcc     360
tcc                                                                  363

<210> SEQ ID NO 6
<211> LENGTH: 121
<212> TYPE: PRT
<213> ORGANISM: Artificial Sequence
<220> FEATURE:
<223> OTHER INFORMATION: Synthetic construct

<400> SEQUENCE: 6

Glu Val Gln Leu Val Gln Ser Gly Pro Glu Val Lys Lys Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Lys Gln Ala Pro Gly Gln Gly Leu Glu Trp Ile
        35                  40                  45

Gly Trp Val Asp Pro Glu Tyr Gly Ser Thr Asp Ser Ala Glu Lys Phe
    50                  55                  60

Lys Lys Arg Ala Thr Leu Thr Ala Asp Ile Ser Thr Asn Thr Ala Tyr
65                  70                  75                  80

Ile Gln Leu Ser Ser Leu Arg Ser Glu Asp Thr Ala Thr Tyr Phe Cys
                85                  90                  95

```
Thr Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120
```

<210> SEQ ID NO 7
<211> LENGTH: 363
<212> TYPE: DNA
<213> ORGANISM: Artificial Sequence
<220> FEATURE:
<223> OTHER INFORMATION: Synthetic construct

<400> SEQUENCE: 7

```
gaggtgcagc tggtgcagtc cggcgccgag gtgaagaagc ccggctcctc cgtgaagatc     60
tcctgcaagg cctccggcta caccttcacc ggctacatcc tgtcctgggt gcgccaggcc    120
cccggccagg gcctggagtg gatcggctgg gtggaccccg agtacggctc caccgactcc    180
gccgagaagt tcaagaagcg cgccaccctg accgccgaca tctccaccaa caccgcctac    240
atcgagctgt cctccctgcg ctccgaggac accgccacct acttctgcac ccgctactac    300
gacggctact accgccgctg gttcgcctac tggggccagg gcaccctggt gaccgtgtcc    360
tcc                                                                   363
```

<210> SEQ ID NO 8
<211> LENGTH: 121
<212> TYPE: PRT
<213> ORGANISM: Artificial Sequence
<220> FEATURE:
<223> OTHER INFORMATION: Synthetic construct

<400> SEQUENCE: 8

```
Glu Val Gln Leu Val Gln Ser Gly Ala Glu Val Lys Lys Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Ala Pro Gly Gln Gly Leu Glu Trp Ile
        35                  40                  45

Gly Trp Val Asp Pro Glu Tyr Gly Ser Thr Asp Ser Ala Glu Lys Phe
    50                  55                  60

Lys Lys Arg Ala Thr Leu Thr Ala Asp Ile Ser Thr Asn Thr Ala Tyr
65                  70                  75                  80

Ile Glu Leu Ser Ser Leu Arg Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120
```

<210> SEQ ID NO 9
<211> LENGTH: 363
<212> TYPE: DNA
<213> ORGANISM: Artificial Sequence
<220> FEATURE:
<223> OTHER INFORMATION: Synthetic construct

<400> SEQUENCE: 9

```
gaggtgcagc tggtgcagtc cggcgccgag gtgaagaagc ccggctcctc cgtgaagatc     60
tcctgcaagg cctccggcta caccttcacc ggctacatcc tgtcctgggt gcgccaggcc    120
cccggccagg gcctggagtg gatcggctgg gtggaccccg agtacggctc caccgactcc    180
```

```
gccgagaagt tcaagaagcg cgccaccctg accgccgaca tctccacctc caccgcctac      240
atcgagctgt cctccctgcg ctccgaggac accgccacct acttctgcac ccgctactac      300
gacggctact accgccgctg gttcgcctac tggggccagg gcaccctggt gaccgtgtcc      360
tcc                                                                    363
```

```
<210> SEQ ID NO 10
<211> LENGTH: 121
<212> TYPE: PRT
<213> ORGANISM: Artificial Sequence
<220> FEATURE:
<223> OTHER INFORMATION: Synthetic construct

<400> SEQUENCE: 10
```

Glu Val Gln Leu Val Gln Ser Gly Ala Glu Val Lys Lys Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Ala Pro Gly Gln Gly Leu Glu Trp Ile
        35                  40                  45

Gly Trp Val Asp Pro Glu Tyr Gly Ser Thr Ser Ala Glu Lys Phe
    50                  55                  60

Lys Lys Arg Ala Thr Leu Thr Ala Asp Ile Ser Thr Ser Thr Ala Tyr
65                  70                  75                  80

Ile Glu Leu Ser Ser Leu Arg Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120

```
<210> SEQ ID NO 11
<211> LENGTH: 363
<212> TYPE: DNA
<213> ORGANISM: Artificial Sequence
<220> FEATURE:
<223> OTHER INFORMATION: Synthetic construct

<400> SEQUENCE: 11
gaggtgcagc tggtgcagtc cggcgccgag gtgaagaagc ccggctcctc cgtgaaggtg       60
tcctgcaagg cctccggcta caccttcacc ggctacatcc tgtcctgggt gcgccaggcc      120
cccggccagg gcctggagtg gatcggctgg gtggaccccg agtacggctc caccgactcc      180
gccgagaagt tcaagaagcg cgccaccatc accgccgaca tctccacctc caccgcctac      240
atggagctgt cctccctgcg ctccgaggac accgccacct acttctgcac ccgctactac      300
gacggctact accgccgctg gttcgcctac tggggccagg gcaccctggt gaccgtgtcc      360
tcc                                                                    363
```

```
<210> SEQ ID NO 12
<211> LENGTH: 121
<212> TYPE: PRT
<213> ORGANISM: Artificial Sequence
<220> FEATURE:
<223> OTHER INFORMATION: Synthetic construct

<400> SEQUENCE: 12
```

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Ile Leu Ser Trp Val Arg Gln Ala Pro Gly Gln Gly Leu Glu Trp Ile
        35                  40                  45

Gly Trp Val Asp Pro Glu Tyr Gly Ser Thr Asp Ser Ala Glu Lys Phe
    50                  55                  60

Lys Lys Arg Ala Thr Ile Thr Ala Asp Ile Ser Thr Ser Thr Ala Tyr
65                  70                  75                  80

Met Glu Leu Ser Ser Leu Arg Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 13
<211> LENGTH: 363
<212> TYPE: DNA
<213> ORGANISM: Artificial Sequence
<220> FEATURE:
<223> OTHER INFORMATION: Synthetic construct

<400> SEQUENCE: 13
gaggtgcagc tggtgcagtc cggcgccgag gtgaagaagc cggctcctc cgtgaaggtg      60 tcctgcaagg cctccggcta caccttcacc ggctacatcc tgtcctgggt gcgccaggcc    120
cccggccagg gctggagtg gatcggctgg gtggaccccg agtacggctc caccgactcc    180
gccgagaagt tcaagaagcg cgtgaccatc accgccgaca tctccacctc caccgcctac    240
atggagctgt cctccctgcg ctccgaggac accgccacct acttctgcac ccgctactac    300
gacggctact accgcgctg gttcgcctac tggggccagg gcaccctggt gaccgtgtcc    360
tcc                                                                   363

<210> SEQ ID NO 14
<211> LENGTH: 121
<212> TYPE: PRT
<213> ORGANISM: Artificial Sequence
<220> FEATURE:
<223> OTHER INFORMATION: Synthetic construct

<400> SEQUENCE: 14

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Ile Leu Ser Trp Val Arg Gln Ala Pro Gly Gln Gly Leu Glu Trp Ile
        35                  40                  45

Gly Trp Val Asp Pro Glu Tyr Gly Ser Thr Asp Ser Ala Glu Lys Phe
    50                  55                  60

Lys Lys Arg Val Thr Ile Thr Ala Asp Ile Ser Thr Ser Thr Ala Tyr
65                  70                  75                  80

Met Glu Leu Ser Ser Leu Arg Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 15
<211> LENGTH: 321
<212> TYPE: DNA
<213> ORGANISM: Artificial Sequence
<220> FEATURE:
<223> OTHER INFORMATION: Synthetic construct

<400> SEQUENCE: 15

```
gacatccaga tgacccagtc ccctcctcc  ctgtccgcct  cgtgggcga  ccgcgtgacc      60
atcacctgcc tggcctccga gggcatctcc aacaacctgg cctggcacca gcagaagccc     120
ggcaaggccc cccagctgct gatctacggc gcccactccc tgcacgacgg cgtgcccgac     180
cgcttctccg gctccggctc cggcaccgac tacaccctga agatctccgg catgcagccc     240
gaggacgagg gcgtgtacta ctgccagcag ggctacaagt accccatcac cttcggcggc     300
ggcaccaagg tggagatcaa g                                               321
```

<210> SEQ ID NO 16
<211> LENGTH: 107
<212> TYPE: PRT
<213> ORGANISM: Artificial Sequence
<220> FEATURE:
<223> OTHER INFORMATION: Synthetic construct

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asn
            20                  25                  30

Leu Ala Trp His Gln Gln Lys Pro Gly Lys Ala Pro Gln Leu Leu Ile
        35                  40                  45

Tyr Gly Ala His Ser Leu His Asp Gly Val Pro Asp Arg Phe Ser Gly
    50                  55                  60

Ser Gly Ser Gly Thr Asp Tyr Thr Leu Lys Ile Ser Gly Met Gln Pro
65                  70                  75                  80

Glu Asp Glu Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105
```

<210> SEQ ID NO 17
<211> LENGTH: 321
<212> TYPE: DNA
<213> ORGANISM: Artificial Sequence
<220> FEATURE:
<223> OTHER INFORMATION: Synthetic construct

<400> SEQUENCE: 17

```
gacatccaga tgacccagtc ccctcctcc  ctgtccgcct  cgtgggcga  ccgcgtgacc      60
atcacctgcc tggcctccga gggcatctcc aacaacctgg cctggcacca gcagaagccc     120
ggcaaggccc ccaagctgct gatctacggc gcccactccc tgcacgacgg cgtgcccgac     180
cgcttctccg gctccggctc cggcaccgac tacaccctga agatctcccg cgtggaggcc     240
gaggacgtgg gcgtgtacta ctgccagcag ggctacaagt accccatcac cttcggcggc     300
ggcaccaagg tggagatcaa g                                               321
```

<210> SEQ ID NO 18
<211> LENGTH: 107

<212> TYPE: PRT
<213> ORGANISM: Artificial Sequence
<220> FEATURE:
<223> OTHER INFORMATION: Synthetic construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asn
            20                  25                  30

Leu Ala Trp His Gln Gln Lys Pro Gly Lys Ala Pro Lys Leu Leu Ile
        35                  40                  45

Tyr Gly Ala His Ser Leu His Asp Gly Val Pro Asp Arg Phe Ser Gly
50                  55                  60

Ser Gly Ser Gly Thr Asp Tyr Thr Leu Lys Ile Ser Arg Val Glu Ala
65                  70                  75                  80

Glu Asp Val Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 19
<211> LENGTH: 321
<212> TYPE: DNA
<213> ORGANISM: Artificial Sequence
<220> FEATURE:
<223> OTHER INFORMATION: Synthetic construct

<400> SEQUENCE: 19
gacatccaga tgacccagtc ccctcctcc ctgtccgcct ccgtgggcga ccgcgtgacc      60
atcacctgcc tggcctccga gggcatctcc aacaacctgg cctggtacca gcagaagccc    120
ggcaaggccc ccaagctgct gatctacggc gcccactccc tgcacgacgg cgtgcccgac   180
cgcttctccg gctccggctc cggcaccgac tacaccctga agatctcccg cgtggaggcc   240
gaggacgtgg gcgtgtacta ctgccagcag ggctacaagt accccatcac cttcggcggc   300
ggcaccaagg tggagatcaa g                                              321

<210> SEQ ID NO 20
<211> LENGTH: 107
<212> TYPE: PRT
<213> ORGANISM: Artificial Sequence
<220> FEATURE:
<223> OTHER INFORMATION: Synthetic construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Ile Ser Asn Asn
            20                  25                  30

Leu Ala Trp Tyr Gln Gln Lys Pro Gly Lys Ala Pro Lys Leu Leu Ile
        35                  40                  45

Tyr Gly Ala His Ser Leu His Asp Gly Val Pro Asp Arg Phe Ser Gly
50                  55                  60

Ser Gly Ser Gly Thr Asp Tyr Thr Leu Lys Ile Ser Arg Val Glu Ala
65                  70                  75                  80

Glu Asp Val Gly Val Tyr Tyr Cys Gln Gln Gly Tyr Lys Tyr Pro Ile
                85                  90                  95

Thr Phe Gly Gly Gly Thr Lys Val Glu Ile Lys

<210> SEQ ID NO 21
<211> LENGTH: 321
<212> TYPE: DNA
<213> ORGANISM: Artificial Sequence
<220> FEATURE:
<223> OTHER INFORMATION: Synthetic construct

<400> SEQUENCE: 21

```
gacatccaga tgacccagtc cccctcctcc ctgtccgcct ccgtgggcga ccgcgtgacc      60
atcacctgcc tggcctccga gggcatctcc aacaacctgg cctggtacca gcagaagccc     120
ggcaaggccc ccaagctgct gatctacggc gcccactccc tgcacgacgg cgtgcccgac     180
cgcttctccg gctccggctc cggcaccgac ttcaccctga agatctcccg cgtggaggcc     240
gaggacgtgg gcgtgtacta ctgccagcag ggctacaagt accccatcac cttcggcggc     300
ggcaccaagg tggagatcaa g                                                321
```

<210> SEQ ID NO 22
<211> LENGTH: 107
<212> TYPE: PRT
<213> ORGANISM: Artificial Sequence
<220> FEATURE:
<223> OTHER INFORMATION: Synthetic construct

<400> SEQUENCE: 22

```
Asp Ile Gln Met Thr Gln Ser Pro Ser Ser Leu Ser Ala Ser Val Gly
1               5                   10                  15
Asp Arg Val Thr Ile Thr Cys Leu Ala Ser Glu Gly Ile Ser Asn Asn
            20                  25                  30
Leu Ala Trp Tyr Gln Gln Lys Pro Gly Lys Ala Pro Lys Leu Leu Ile
        35                  40                  45
Tyr Gly Ala His Ser Leu His Asp Gly Val Pro Asp Arg Phe Ser Gly
    50                  55                  60
Ser Gly Ser Gly Thr Asp Phe Thr Leu Lys Ile Ser Arg Val Glu Ala
65                  70                  75                  80
Glu Asp Val Gly Val Tyr Tyr Cys Gln Gln Gly Tyr Lys Tyr Pro Ile
                85                  90                  95
Thr Phe Gly Gly Gly Thr Lys Val Glu Ile Lys
            100                 105
```

<210> SEQ ID NO 23
<211> LENGTH: 5
<212> TYPE: PRT
<213> ORGANISM: Artificial Sequence
<220> FEATURE:
<223> OTHER INFORMATION: Synthetic construct

<400> SEQUENCE: 23

```
Gly Tyr Ile Leu Ser
1               5
```

<210> SEQ ID NO 24
<211> LENGTH: 17
<212> TYPE: PRT
<213> ORGANISM: Artificial Sequence
<220> FEATURE:
<223> OTHER INFORMATION: Synthetic construct

<400> SEQUENCE: 24

```
Trp Val Asp Pro Glu Tyr Gly Ser Thr Asp Ser Ala Glu Lys Phe Lys
```

```
1               5                  10                  15
Lys

<210> SEQ ID NO 25
<211> LENGTH: 12
<212> TYPE: PRT
<213> ORGANISM: Artificial Sequence
<220> FEATURE:
<223> OTHER INFORMATION: Synthetic construct

<400> SEQUENCE: 25

Tyr Tyr Asp Gly Tyr Tyr Arg Arg Trp Phe Ala Tyr
1               5                  10

<210> SEQ ID NO 26
<211> LENGTH: 11
<212> TYPE: PRT
<213> ORGANISM: Artificial Sequence
<220> FEATURE:
<223> OTHER INFORMATION: Synthetic construct

<400> SEQUENCE: 26

Leu Ala Ser Glu Gly Ile Ser Asn Asn Leu Ala
1               5                  10

<210> SEQ ID NO 27
<211> LENGTH: 7
<212> TYPE: PRT
<213> ORGANISM: Artificial Sequence
<220> FEATURE:
<223> OTHER INFORMATION: Synthetic construct

<400> SEQUENCE: 27

Gly Ala His Ser Leu His Asp
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Gln Gln Gly Tyr Lys Tyr Pro Ile Thr
1               5

<210> SEQ ID NO 29
<211> LENGTH: 121
<212> TYPE: PRT
<213> ORGANISM: Artificial Sequence
<220> FEATURE:
<223> OTHER INFORMATION: Synthetic construct

<400> SEQUENCE: 29

Glu Val Gln Leu Val Gln Ser Gly Pro Glu Val Lys Lys Pro Gly Ala
1               5                  10                  15

Ser Val Lys Ile Ser Cys Lys Ala Ser Gly Tyr Thr Phe Thr Gly Tyr
                20                  25                  30

Ile Leu Ser Trp Val Lys Gln Ala Pro Gly Lys Gly Leu Glu Trp Ile
            35                  40                  45

Gly Trp Val Asp Pro Glu Tyr Gly Ser Thr Asp Ser Ala Glu Lys Phe
        50                  55                  60

Lys Lys Arg Ala Thr Leu Thr Ala Asp Ile Ser Ala Asn Thr Ala Tyr
```

Ile Gln Leu Ser Ser Leu Thr Ser Glu Asp Thr Ala Thr Tyr Phe Cys
            85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 30
<211> LENGTH: 121
<212> TYPE: PRT
<213> ORGANISM: Artificial Sequence
<220> FEATURE:
<223> OTHER INFORMATION: Synthetic construct

<400> SEQUENCE: 30

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Ser Ala Glu Lys Phe
    50                  55                  60

Lys Lys Arg Ala Thr Leu Thr Ala Asp Ile Ser Ala Asn Thr Ala Tyr
65                  70                  75                  80

Ile Glu Leu Ser Ser Leu Thr Ser Glu Asp Thr Ala Thr Tyr Phe Cys
            85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 31
<211> LENGTH: 121
<212> TYPE: PRT
<213> ORGANISM: Artificial Sequence
<220> FEATURE:
<223> OTHER INFORMATION: Synthetic construct

<400> SEQUENCE: 31

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Ser Ala Glu Lys Phe
    50                  55                  60

Lys Lys Arg Ala Thr Leu Thr Ala Asp Ile Ser Ala Ser Thr Ala Tyr
65                  70                  75                  80

Ile Glu Leu Ser Ser Leu Thr Ser Glu Asp Thr Ala Thr Tyr Phe Cys
            85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 32
<211> LENGTH: 121
<212> TYPE: PRT
<213> ORGANISM: Artificial Sequence
<220> FEATURE:
<223> OTHER INFORMATION: Synthetic construct

<400> SEQUENCE: 32

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Ser Ala Glu Lys Phe
    50                  55                  60

Lys Lys Arg Ala Thr Ile Thr Ala Asp Ile Ser Ala Ser Thr Ala Tyr
65                  70                  75                  80

Met Glu Leu Ser Ser Leu Thr Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
                100                 105                 110

Gln Gly Thr Leu Val Thr Val Ser Ser
        115                 120
```

<210> SEQ ID NO 33
<211> LENGTH: 121
<212> TYPE: PRT
<213> ORGANISM: Artificial Sequence
<220> FEATURE:
<223> OTHER INFORMATION: Synthetic construct

<400> SEQUENCE: 33

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Ser Ala Glu Lys Phe
    50                  55                  60

Lys Lys Arg Val Thr Ile Thr Ala Asp Ile Ser Ala Ser Thr Ala Tyr
65                  70                  75                  80

Met Glu Leu Ser Ser Leu Thr Ser Glu Asp Thr Ala Thr Tyr Phe Cys
                85                  90                  95

Thr Arg Tyr Tyr Asp Gly Tyr Tyr Arg Arg Trp Phe Ala Tyr Trp Gly
                100                 105                 110

Gln Gly Thr Leu Val Thr Val Ser Ser
        115                 120
```

<210> SEQ ID NO 34
<211> LENGTH: 121
<212> TYPE: PRT
<213> ORGANISM: Artificial Sequence
<220> FEATURE:
<223> OTHER INFORMATION: Synthetic construct

<400> SEQUENCE: 34

```
Glu Val Gln Leu Val Gln Ser Gly Pro Glu Val Lys Lys Pro Gly Ala
```

```
            1               5                  10                 15
        Ser Val Lys Ile Ser Cys Lys Ala Ser Gly Tyr Thr Phe Thr Gly Tyr
                        20                  25                  30

Ile Leu Ser Trp Val Lys Gln Ala Pro Gly Lys Gly Leu Glu Trp Ile
                        35                  40                  45

Gly Trp Val Asp Pro Glu Tyr Gly Ser Thr Asp Ser Ala Glu Lys Phe
                    50                  55                  60

Lys Lys Arg Ala Thr Leu Thr Ala Asp Ile Ser Lys Asn Thr Ala Tyr
        65                  70                  75                  80

Ile Gln Leu Asn Ser Leu Thr Ala Glu Asp Thr Ala Thr Tyr Phe Cys
                        85                  90                  95

Thr Arg Tyr Tyr Asp Gly Tyr Tyr Arg Arg Trp Phe Ala Tyr Trp Gly
                        100                 105                 110

Gln Gly Thr Leu Val Thr Val Ser Ser
                        115                 120

<210> SEQ ID NO 35
<211> LENGTH: 121
<212> TYPE: PRT
<213> ORGANISM: Artificial Sequence
<220> FEATURE:
<223> OTHER INFORMATION: Synthetic construct

<400> SEQUENCE: 35

Glu Val Gln Leu Val Gln Ser Gly Ala Glu Val Lys Lys Pro Gly Ala
        1               5                   10                  15

Ser Val Lys Ile Ser Cys Lys Ala Ser Gly Tyr Thr Phe Thr Gly Tyr
                        20                  25                  30

Ile Leu Ser Trp Val Arg Gln Ala Pro Gly Lys Gly Leu Glu Trp Ile
                        35                  40                  45

Gly Trp Val Asp Pro Glu Tyr Gly Ser Thr Asp Ser Ala Glu Lys Phe
                    50                  55                  60

Lys Lys Arg Ala Thr Leu Thr Ala Asp Ile Ser Lys Asn Thr Ala Tyr
        65                  70                  75                  80

Ile Gln Leu Asn Ser Leu Thr Ala Glu Asp Thr Ala Thr Tyr Phe Cys
                        85                  90                  95

Thr Arg Tyr Tyr Asp Gly Tyr Tyr Arg Arg Trp Phe Ala Tyr Trp Gly
                        100                 105                 110

Gln Gly Thr Leu Val Thr Val Ser Ser
                        115                 120

<210> SEQ ID NO 36
<211> LENGTH: 121
<212> TYPE: PRT
<213> ORGANISM: Artificial Sequence
<220> FEATURE:
<223> OTHER INFORMATION: Synthetic construct

<400> SEQUENCE: 36

Glu Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Gly Tyr
                        20                  25                  30

Ile Leu Ser Trp Val Arg Gln Ala Pro Gly Lys Gly Leu Glu Trp Ile
                        35                  40                  45

Gly Trp Val Asp Pro Glu Tyr Gly Ser Thr Asp Ser Ala Glu Lys Phe
                    50                  55                  60
```

Lys Lys Arg Ala Thr Leu Thr Ala Asp Ile Ser Lys Asn Thr Ala Tyr
65                  70                  75                  80

Ile Gln Leu Asn Ser Leu Thr Ala Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 37
<211> LENGTH: 121
<212> TYPE: PRT
<213> ORGANISM: Artificial Sequence
<220> FEATURE:
<223> OTHER INFORMATION: Synthetic construct

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Asp Ser Ala Glu Lys Phe
    50                  55                  60

Lys Lys Arg Ala Thr Ile Thr Ala Asp Ile Ser Lys Asn Thr Ala Tyr
65                  70                  75                  80

Leu Gln Leu Asn Ser Leu Thr Ala Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 38
<211> LENGTH: 121
<212> TYPE: PRT
<213> ORGANISM: Artificial Sequence
<220> FEATURE:
<223> OTHER INFORMATION: Synthetic construct

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Gly Tyr
                20                  25                  30

Ile Leu Ser Trp Val Arg Gln Ala Pro Gly Lys Gly Leu Glu Trp Ile
            35                  40                  45

Gly Trp Val Asp Pro Glu Tyr Gly Ser Thr Asp Ser Ala Glu Lys Phe
    50                  55                  60

Lys Lys Arg Phe Thr Ile Thr Ala Asp Ile Ser Lys Asn Thr Ala Tyr
65                  70                  75                  80

Leu Gln Met Asn Ser Leu Thr Ala Glu Asp Thr Ala Thr Tyr Phe Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
            115                 120

<210> SEQ ID NO 39
<211> LENGTH: 97
<212> TYPE: PRT
<213> ORGANISM: Artificial Sequence
<220> FEATURE:
<223> OTHER INFORMATION: Synthetic construct

<400> SEQUENCE: 39

Gln Val Gln Leu Gln Glu Ser Gly Pro Gly Leu Val Lys Pro Ser Glu
1               5                   10                  15

Thr Leu Ser Leu Ile Cys Ala Val Ser Gly Asp Ser Ile Ser Ser Gly
            20                  25                  30

Asn Trp Ile Trp Val Arg Gln Pro Pro Gly Lys Gly Leu Glu Trp Ile
        35                  40                  45

Gly Glu Ile His His Ser Gly Ser Thr Tyr Tyr Asn Pro Ser Leu Lys
    50                  55                  60

Ser Arg Ile Thr Met Ser Val Asp Thr Ser Lys Asn Gln Phe Tyr Leu
65                  70                  75                  80

Lys Leu Ser Ser Val Thr Ala Ala Asp Thr Ala Val Tyr Tyr Cys Ala
                85                  90                  95

Arg

<210> SEQ ID NO 40
<211> LENGTH: 97
<212> TYPE: PRT
<213> ORGANISM: Artificial Sequence
<220> FEATURE:
<223> OTHER INFORMATION: Synthetic construct

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 41
<211> LENGTH: 98
<212> TYPE: PRT
<213> ORGANISM: Artificial Sequence
<220> FEATURE:
<223> OTHER INFORMATION: Synthetic construct

<400> SEQUENCE: 41

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg

<210> SEQ ID NO 42
<211> LENGTH: 98
<212> TYPE: PRT
<213> ORGANISM: Artificial Sequence
<220> FEATURE:
<223> OTHER INFORMATION: Synthetic construct

<400> SEQUENCE: 42

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Ser Asn Ser Ala
                20                  25                  30

Ala Trp Asn Trp Ile Arg Gln Ser Pro Ser Arg Gly Leu Glu Trp Leu
            35                  40                  45

Gly Arg Thr Tyr Tyr Ser Lys Trp Tyr Asn Asp Tyr Ala Val Ser Val
     50                  55                  60

Lys Ser Arg Ile Thr Ile Asn Pro Asp Thr Ser Lys Asn Gln Phe Ser
 65                  70                  75                  80

Leu Gln Leu Asn Ser Val Thr Pro Glu Asp Thr Ala Val Tyr Tyr Cys
                85                  90                  95

Ala Arg

<210> SEQ ID NO 43
<211> LENGTH: 98
<212> TYPE: PRT
<213> ORGANISM: Artificial Sequence
<220> FEATURE:
<223> OTHER INFORMATION: Synthetic construct

<400> SEQUENCE: 43

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                85                  90                  95

Ala Arg

<210> SEQ ID NO 44
<211> LENGTH: 107
<212> TYPE: PRT
<213> ORGANISM: Artificial Sequence
<220> FEATURE:
<223> OTHER INFORMATION: Synthetic construct

<400> SEQUENCE: 44

Asp Ile Gln Met Thr Gln Ser Pro Asp Ser Leu Ser Ala Ser Leu Gly
1               5                   10                  15

Asp Arg Ala Thr Ile Asn Cys Leu Ala Ser Glu Gly Ile Ser Asn Asn
            20                  25                  30

Leu Ala Trp His Gln Gln Lys Pro Gly Gln Ser Pro Gln Leu Leu Ile
        35                  40                  45

Tyr Gly Ala His Ser Leu His Asp Gly Val Pro Ser Arg Phe Ser Gly
    50                  55                  60

Ser Gly Ser Gly Thr Glu Tyr Thr Leu Lys Ile Ser Gly Met Gln Pro
65                  70                  75                  80

Glu Asp Glu Ala Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: Synthetic construct

<400> SEQUENCE: 45

Asp Ile Gln Met Thr Gln Ser Pro Asp Ser Leu Ser Ala Ser Leu Gly
1               5                   10                  15

Asp Arg Ala Thr Ile Asn Cys Leu Ala Ser Glu Gly Ile Ser Asn Asn
            20                  25                  30

Leu Ala Trp His Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Glu Tyr Thr Leu Lys Ile Ser Ser Met Gln Pro
65                  70                  75                  80

Glu Asp Phe Ala Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: Synthetic construct

<400> SEQUENCE: 46

Asp Ile Val Met Thr Gln Ser Pro Asp Ser Leu Ser Ala Ser Leu Gly
1               5                   10                  15

Asp Arg Ala Thr Ile Asn Cys Leu Ala Ser Glu Gly Ile Ser Asn Asn
            20                  25                  30

Leu Ala Trp His Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Glu Tyr Thr Leu Lys Ile Ser Ser Met Gln Pro
65                  70                  75                  80

Glu Asp Phe Ala Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: Synthetic construct

<400> SEQUENCE: 47

Asp Ile Val Met Thr Gln Ser Pro Asp Ser Leu Ser Ala Ser Leu Gly
1               5                   10                  15

Asp Arg Ala Thr Ile Asn Cys Leu Ala Ser Glu Gly Ile Ser Asn Asn
            20                  25                  30

Leu Ala Trp Tyr Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Glu Tyr Thr Leu Lys Ile Ser Ser Met Gln Pro
65                  70                  75                  80

Glu Asp Phe Ala Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: Synthetic construct

<400> SEQUENCE: 48

Asp Ile Gln Met Thr Gln Ser Pro Ala Ser Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp His Gln Gln Lys Pro Gly Gln Ser Pro Gln Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Lys Ile Ser Gly Met Gln Pro
65                  70                  75                  80

Glu Asp Glu Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: Synthetic construct

<400> SEQUENCE: 49

```
Asp Ile Gln Met Thr Gln Ser Pro Ala Ser Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp His Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Lys Ile Ser Arg Val Glu Pro
65              70                  75                  80

Glu Asp Val Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105
```

<210> SEQ ID NO 50
<211> LENGTH: 107
<212> TYPE: PRT
<213> ORGANISM: Artificial Sequence
<220> FEATURE:
<223> OTHER INFORMATION: Synthetic construct

<400> SEQUENCE: 50

```
Asp Ile Gln Met Thr Gln Ser Pro Ala Thr Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp His Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Lys Ile Ser Arg Val Glu Ala
65              70                  75                  80

Glu Asp Val Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105
```

<210> SEQ ID NO 51
<211> LENGTH: 107
<212> TYPE: PRT
<213> ORGANISM: Artificial Sequence
<220> FEATURE:
<223> OTHER INFORMATION: Synthetic construct

<400> SEQUENCE: 51

```
Glu Ile Gln Met Thr Gln Ser Pro Ala Thr Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp His Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Lys Ile Ser Arg Val Glu Ala
65              70                  75                  80

Glu Asp Val Gly Val Tyr Tyr Cys Gln Gln Gly Tyr Lys Tyr Pro Ile
                85                  90                  95
```

Thr Phe Gly Gly Gly Thr Lys Val Glu Ile Lys
            100                 105

<210> SEQ ID NO 52
<211> LENGTH: 107
<212> TYPE: PRT
<213> ORGANISM: Artificial Sequence
<220> FEATURE:
<223> OTHER INFORMATION: Synthetic construct

<400> SEQUENCE: 52

Glu Ile Val Met Thr Gln Ser Pro Ala Thr Leu Ser Ala Ser Leu Gly
1               5                   10                  15

Asp Ile Val Ser Ile Glu Cys Leu Ala Ser Glu Gly Ile Ser Asn Asn
            20                  25                  30

Leu Ala Trp Tyr Gln Gln Lys Pro Gly Gln Ser Pro Arg Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Lys Ile Ser Arg Val Glu Ala
65                  70                  75                  80

Glu Asp Val Gly Val Tyr Tyr Cys Gln Gln Gly Tyr Lys Tyr Pro Ile
                85                  90                  95

Thr Phe Gly Gly Gly Thr Lys Val Glu Ile Lys
            100                 105

<210> SEQ ID NO 53
<211> LENGTH: 95
<212> TYPE: PRT
<213> ORGANISM: Artificial Sequence
<220> FEATURE:
<223> OTHER INFORMATION: Synthetic construct

<400> SEQUENCE: 53

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 54
<211> LENGTH: 95
<212> TYPE: PRT
<213> ORGANISM: Artificial Sequence
<220> FEATURE:
<223> OTHER INFORMATION: Synthetic construct

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asp Gly Asn Thr Tyr
            20                  25                  30

Leu Asn Trp Phe Gln Gln Arg Pro Gly Gln Ser Pro Arg Arg Leu Ile
            35                  40                  45

Tyr Lys Val Ser Asn Trp Asp Ser Gly Val Pro Asp Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Met Gln Gly Thr His Trp Pro
                 85                  90                  95

<210> SEQ ID NO 55
<211> LENGTH: 95
<212> TYPE: PRT
<213> ORGANISM: Artificial Sequence
<220> FEATURE:
<223> OTHER INFORMATION: Synthetic construct

<400> SEQUENCE: 55

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Val Ser Ser Ser Tyr
                 20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro
                 85                  90                  95

<210> SEQ ID NO 56
<211> LENGTH: 95
<212> TYPE: PRT
<213> ORGANISM: Artificial Sequence
<220> FEATURE:
<223> OTHER INFORMATION: Synthetic construct

<400> SEQUENCE: 56

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Asn Asn Lys Asn Tyr
                 20                  25                  30

Leu Ala Trp Tyr Gln Gln Lys Pro Gly Gln Pro Pro Lys Leu Leu Ile
            35                  40                  45

Tyr Trp Ala Ser Thr Arg Glu Ser Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Tyr Tyr Ser Thr Pro
                 85                  90                  95

<210> SEQ ID NO 57
<211> LENGTH: 95
<212> TYPE: PRT
<213> ORGANISM: Artificial Sequence
<220> FEATURE:
<223> OTHER INFORMATION: Synthetic construct

<400> SEQUENCE: 57

Asp Val Val Met Thr Gln Ser Pro Ala Phe Leu Ser Val Thr Pro Gly

```
                1               5                   10                  15
            Glu Lys Val Thr Ile Thr Cys Gln Ala Ser Glu Gly Ile Gly Asn Tyr
                        20                  25                  30
            Leu Tyr Trp Tyr Gln Gln Lys Pro Asp Gln Ala Pro Lys Leu Leu Ile
                    35                  40                  45
            Lys Tyr Ala Ser Gln Ser Ile Ser Gly Val Pro Ser Arg Phe Ser Gly
                50                  55                  60
            Ser Gly Ser Gly Thr Asp Phe Thr Phe Thr Ile Ser Ser Leu Glu Ala
            65                  70                  75                  80
            Glu Asp Ala Ala Thr Tyr Tyr Cys Gln Gln Gly Asn Lys His Pro
                                85                  90                  95
```

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
atgrasttsk ggytmarctk grttt                                              25

<210> SEQ ID NO 59
<211> LENGTH: 26
<212> TYPE: DNA
<213> ORGANISM: Artificial Sequence
<220> FEATURE:
<223> OTHER INFORMATION: Primer

<400> SEQUENCE: 59
atgraatgsa sctgggtywt yctctt                                             26

<210> SEQ ID NO 60
<211> LENGTH: 29
<212> TYPE: DNA
<213> ORGANISM: Artificial Sequence
<220> FEATURE:
<223> OTHER INFORMATION: Primer

<400> SEQUENCE: 60
atggactcca ggctcaattt agttttcct                                          29

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
atggctgtcy trgbgctgyt cytctg                                             26

<210> SEQ ID NO 62
<211> LENGTH: 29
<212> TYPE: DNA
<213> ORGANISM: Artificial Sequence
<220> FEATURE:
<223> OTHER INFORMATION: Primer

<400> SEQUENCE: 62
atggvttggs tgtggamctt gcyattcct                                          29

<210> SEQ ID NO 63

```
<211> LENGTH: 26
<212> TYPE: DNA
<213> ORGANISM: Artificial Sequence
<220> FEATURE:
<223> OTHER INFORMATION: Primer

<400> SEQUENCE: 63
atgaaatgca gctggrtyat sttctt                                          26

<210> SEQ ID NO 64
<211> LENGTH: 26
<212> TYPE: DNA
<213> ORGANISM: Artificial Sequence
<220> FEATURE:
<223> OTHER INFORMATION: Primer

<400> SEQUENCE: 64
atggrcagrc ttacwtyytc attcct                                          26

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65
atgatggtgt taagtcttct gtacct                                          26

<210> SEQ ID NO 66
<211> LENGTH: 26
<212> TYPE: DNA
<213> ORGANISM: Artificial Sequence
<220> FEATURE:
<223> OTHER INFORMATION: Primer

<400> SEQUENCE: 66
atgggatgga gctrtatcat sytctt                                          26

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
atgaagwtgt ggbtraactg grt                                             23

<210> SEQ ID NO 68
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is Inosine

<400> SEQUENCE: 68
atggratgga sckknrtctt tmtct                                           25

<210> SEQ ID NO 69
<211> LENGTH: 25
<212> TYPE: DNA
<213> ORGANISM: Artificial Sequence
```

```
<220> FEATURE:
<223> OTHER INFORMATION: Primer

<400> SEQUENCE: 69
atgaacttyg ggytsagmtt grttt                                              25

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
atgtacttgg gactgagctg tgtat                                              25

<210> SEQ ID NO 71
<211> LENGTH: 23
<212> TYPE: DNA
<213> ORGANISM: Artificial Sequence
<220> FEATURE:
<223> OTHER INFORMATION: Primer

<400> SEQUENCE: 71
atgagagtgc tgattctttt gtg                                                23

<210> SEQ ID NO 72
<211> LENGTH: 28
<212> TYPE: DNA
<213> ORGANISM: Artificial Sequence
<220> FEATURE:
<223> OTHER INFORMATION: Primer

<400> SEQUENCE: 72
atggattttg ggctgatttt ttttattg                                           28

<210> SEQ ID NO 73
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(21)
<223> OTHER INFORMATION: n is Inosine

<400> SEQUENCE: 73
ccagggrcca rkggatarac ngrtgg                                             26

<210> SEQ ID NO 74
<211> LENGTH: 24
<212> TYPE: DNA
<213> ORGANISM: Artificial Sequence
<220> FEATURE:
<223> OTHER INFORMATION: Primer

<400> SEQUENCE: 74
atgragwcac akwcycaggt cttt                                               24

<210> SEQ ID NO 75
<211> LENGTH: 25
<212> TYPE: DNA
<213> ORGANISM: Artificial Sequence
<220> FEATURE:
<223> OTHER INFORMATION: Primer
```

<400> SEQUENCE: 75
atggagacag acacactcct gctat                                       25

<210> SEQ ID NO 76
<211> LENGTH: 29
<212> TYPE: DNA
<213> ORGANISM: Artificial Sequence
<220> FEATURE:
<223> OTHER INFORMATION: Primer

<400> SEQUENCE: 76
atggagwcag acacactsct gytatgggt                                   29

<210> SEQ ID NO 77
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (27)..(27)
<223> OTHER INFORMATION: n is Inosine

<400> SEQUENCE: 77
atgaggrccc ctgctcagwt tyttggnwtc tt                               32

<210> SEQ ID NO 78
<211> LENGTH: 30
<212> TYPE: DNA
<213> ORGANISM: Artificial Sequence
<220> FEATURE:
<223> OTHER INFORMATION: Primer

<400> SEQUENCE: 78
tgggcwtcaa gatgragtca cakwyycwgg                                  30

<210> SEQ ID NO 79
<211> LENGTH: 29
<212> TYPE: DNA
<213> ORGANISM: Artificial Sequence
<220> FEATURE:
<223> OTHER INFORMATION: Primer

<400> SEQUENCE: 79
atgagtgtgc ycactcaggt cctggsgtt                                   29

<210> SEQ ID NO 80
<211> LENGTH: 31
<212> TYPE: DNA
<213> ORGANISM: Artificial Sequence
<220> FEATURE:
<223> OTHER INFORMATION: Primer

<400> SEQUENCE: 80
atgtggggay cgktttyamm cttttcaatt g                                31

<210> SEQ ID NO 81
<211> LENGTH: 28
<212> TYPE: DNA
<213> ORGANISM: Artificial Sequence
<220> FEATURE:
<223> OTHER INFORMATION: Primer

<400> SEQUENCE: 81
atggaagccc cagctcagct tctcttcc                                    28

```
<210> SEQ ID NO 82
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is Inosine
<220> FEATURE:
<221> NAME/KEY: misc_feature
<222> LOCATION: (12)..(12)
<223> OTHER INFORMATION: n is Inosine
<220> FEATURE:
<221> NAME/KEY: misc_feature
<222> LOCATION: (18)..(18)
<223> OTHER INFORMATION: n is Inosine

<400> SEQUENCE: 82
atgagnmmkt cnmttcantt cytggg                                          26

<210> SEQ ID NO 83
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: n is Inosine
<220> FEATURE:
<221> NAME/KEY: misc_feature
<222> LOCATION: (24)..(24)
<223> OTHER INFORMATION: n is Inosine

<400> SEQUENCE: 83
atgakgthcy cngctcagyt yctnrg                                          26

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
atggtrtccw casctcagtt ccttg                                           25

<210> SEQ ID NO 85
<211> LENGTH: 27
<212> TYPE: DNA
<213> ORGANISM: Artificial Sequence
<220> FEATURE:
<223> OTHER INFORMATION: Primer

<400> SEQUENCE: 85
atgtatatat gtttgttgtc tatttct                                         27

<210> SEQ ID NO 86
<211> LENGTH: 29
<212> TYPE: DNA
<213> ORGANISM: Artificial Sequence
<220> FEATURE:
<223> OTHER INFORMATION: Primer

<400> SEQUENCE: 86
```
atgaagttgc ctgttaggct gttggtgct                                    29

<210> SEQ ID NO 87
<211> LENGTH: 29
<212> TYPE: DNA
<213> ORGANISM: Artificial Sequence
<220> FEATURE:
<223> OTHER INFORMATION: Primer

<400> SEQUENCE: 87
atggatttwc argtgcagat twtcagctt                                    29

<210> SEQ ID NO 88
<211> LENGTH: 27
<212> TYPE: DNA
<213> ORGANISM: Artificial Sequence
<220> FEATURE:
<223> OTHER INFORMATION: Primer

<400> SEQUENCE: 88
atggtyctya tvtccttgct gttctgg                                      27

<210> SEQ ID NO 89
<211> LENGTH: 27
<212> TYPE: DNA
<213> ORGANISM: Artificial Sequence
<220> FEATURE:
<223> OTHER INFORMATION: Primer

<400> SEQUENCE: 89
atggtyctya tvttrctgct gctatgg                                      27

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
actggatggt gggaagatgg a                                            21

<210> SEQ ID NO 91
<211> LENGTH: 120
<212> TYPE: PRT
<213> ORGANISM: Artificial Sequence
<220> FEATURE:
<223> OTHER INFORMATION: Synthetic construct

<400> SEQUENCE: 91

Gln Val Gln Leu Gln Glu Ser Gly Pro Gly Leu Val Lys Pro Ser Glu
1               5                   10                  15

Thr Leu Ser Leu Ile Cys Ala Val Ser Gly Asp Ser Ile Ser Ser Gly
            20                  25                  30

Asn Trp Ile Trp Val Arg Gln Pro Pro Gly Lys Gly Leu Glu Trp Ile
        35                  40                  45

Gly Glu Ile His His Ser Gly Ser Thr Tyr Tyr Asn Pro Ser Leu Lys
    50                  55                  60

Ser Arg Ile Thr Met Ser Val Asp Thr Ser Lys Asn Gln Phe Tyr Leu
65                  70                  75                  80

Lys Leu Ser Ser Val Thr Ala Ala Asp Thr Ala Val Tyr Tyr Cys Ala
                85                  90                  95

Arg Tyr Tyr Asp Gly Tyr Tyr Arg Arg Trp Phe Ala Tyr Trp Gly Arg

-continued

```
                100                 105                 110

Gly Thr Leu Val Thr Val Ser Ser
            115                 120

<210> SEQ ID NO 92
<211> LENGTH: 121
<212> TYPE: PRT
<213> ORGANISM: Artificial Sequence
<220> FEATURE:
<223> OTHER INFORMATION: Synthetic construct

<400> SEQUENCE: 92

Glu Val Gln Leu Gln Gln Ser Gly Pro Gly Leu Gly Arg Pro Gly Ser
1               5                   10                  15

Ser Val Lys Ile Ser Cys Lys Ala Ser Gly Tyr Thr Phe Thr Gly Tyr
                20                  25                  30

Ile Leu Ser Trp Val Arg Gln Pro Pro Gly Lys Gly Leu Glu Trp Ile
            35                  40                  45

Gly Trp Val Asp Pro Glu Tyr Gly Ser Thr Asp Ser Ala Glu Lys Phe
        50                  55                  60

Lys Lys Arg Ala Thr Met Ser Ala Asp Ile Ser Lys Asn Gln Ala Tyr
65                  70                  75                  80

Leu Lys Leu Ser Ser Val Thr Ala Ala Asp Thr Ala Thr Tyr Tyr Cys
                85                  90                  95

Thr Arg Tyr Tyr Asp Gly Tyr Tyr Arg Arg Trp Phe Ala Tyr Trp Gly
                100                 105                 110

Arg Gly Thr Leu Val Thr Val Ser Ser
            115                 120

<210> SEQ ID NO 93
<211> LENGTH: 120
<212> TYPE: PRT
<213> ORGANISM: Artificial Sequence
<220> FEATURE:
<223> OTHER INFORMATION: Synthetic construct

<400> SEQUENCE: 93

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Asn Pro Ser Leu Lys
        50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Tyr Asp Gly Tyr Tyr Arg Arg Trp Phe Ala Tyr Trp Gly Gln
                100                 105                 110

Gly Thr Leu Val Thr Val Ser Ser
            115                 120

<210> SEQ ID NO 94
<211> LENGTH: 121
<212> TYPE: PRT
<213> ORGANISM: Artificial Sequence
<220> FEATURE:
```

<223> OTHER INFORMATION: Synthetic construct

<400> SEQUENCE: 94

Glu Val Gln Leu Gln Gln Trp Gly Ala Gly Leu Gly Arg Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Pro Pro Gly Lys Gly Leu Glu Trp Ile
        35                  40                  45

Gly Trp Val Asp Pro Glu Tyr Gly Ser Thr Asp Ser Ala Glu Lys Phe
    50                  55                  60

Lys Lys Arg Ala Thr Ile Ser Ala Asp Ile Ser Lys Asn Gln Ala Tyr
65                  70                  75                  80

Leu Lys Leu Ser Ser Val Thr Ala Ala Asp Thr Ala Thr Tyr Tyr Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120

<210> SEQ ID NO 95
<211> LENGTH: 121
<212> TYPE: PRT
<213> ORGANISM: Artificial Sequence
<220> FEATURE:
<223> OTHER INFORMATION: Synthetic construct

<400> SEQUENCE: 95

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120

<210> SEQ ID NO 96
<211> LENGTH: 121
<212> TYPE: PRT
<213> ORGANISM: Artificial Sequence
<220> FEATURE:
<223> OTHER INFORMATION: Synthetic construct

<400> SEQUENCE: 96

Glu Val Gln Leu Val Gln Ser Gly Ala Glu Val Gly Arg Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Met Pro Gly Lys Gly Leu Glu Trp Ile

```
                35                  40                  45
Gly Trp Val Asp Pro Glu Tyr Gly Ser Thr Asp Ser Ala Glu Lys Phe
        50                  55                  60

Lys Lys Arg Ala Thr Leu Ser Ala Asp Ile Ser Ile Asn Thr Ala Tyr
 65                  70                  75                  80

Leu Gln Leu Ser Ser Leu Lys Ala Ser Asp Thr Ala Thr Tyr Tyr Cys
                85                  90                  95

Thr Arg Tyr Tyr Asp Gly Tyr Tyr Arg Arg Trp Phe Ala Tyr Trp Gly
                100                 105                 110

Gln Gly Thr Leu Val Thr Val Ser Ser
                115                 120
```

<210> SEQ ID NO 97
<211> LENGTH: 121
<212> TYPE: PRT
<213> ORGANISM: Artificial Sequence
<220> FEATURE:
<223> OTHER INFORMATION: Synthetic construct

<400> SEQUENCE: 97

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Ser Asn Ser Ala
                20                  25                  30

Ala Trp Asn Trp Ile Arg Gln Ser Pro Ser Arg Gly Leu Glu Trp Leu
                35                  40                  45

Gly Arg Thr Tyr Tyr Ser Lys Trp Tyr Asn Asp Tyr Ala Val Ser Val
        50                  55                  60

Lys Ser Arg Ile Thr Ile Asn Pro Asp Thr Ser Lys Asn Gln Phe Ser
 65                  70                  75                  80

Leu Gln Leu Asn Ser Val Thr Pro Glu Asp Thr Ala Val Tyr Tyr Cys
                85                  90                  95

Ala Arg Tyr Tyr Asp Gly Tyr Tyr Arg Arg Trp Phe Ala Tyr Trp Gly
                100                 105                 110

Gln Gly Thr Leu Val Thr Val Ser Ser
                115                 120
```

<210> SEQ ID NO 98
<211> LENGTH: 121
<212> TYPE: PRT
<213> ORGANISM: Artificial Sequence
<220> FEATURE:
<223> OTHER INFORMATION: Synthetic construct

<400> SEQUENCE: 98

```
Glu Val Gln Leu Gln Gln Ser Gly Pro Gly Leu Gly Arg Pro Gly Ser
 1               5                  10                  15

Ser Val Lys Ile Ser Cys Lys Ala Ser Gly Tyr Thr Phe Thr Gly Tyr
                20                  25                  30

Ile Leu Ser Trp Val Arg Gln Ser Pro Ser Arg Gly Leu Glu Trp Ile
                35                  40                  45

Gly Trp Val Asp Pro Glu Tyr Gly Ser Thr Asp Ser Ala Glu Lys Phe
        50                  55                  60

Lys Lys Arg Ala Thr Leu Asn Ala Asp Ile Ser Lys Asn Gln Ala Tyr
 65                  70                  75                  80

Leu Gln Leu Asn Ser Val Thr Pro Glu Asp Thr Ala Thr Tyr Tyr Cys
                85                  90                  95
```

Thr Arg Tyr Tyr Asp Gly Tyr Tyr Arg Arg Trp Phe Ala Tyr Trp Gly
            100                 105                 110

Gln Gly Thr Thr Val Thr Val Ser Ser
        115                 120

<210> SEQ ID NO 99
<211> LENGTH: 121
<212> TYPE: PRT
<213> ORGANISM: Artificial Sequence
<220> FEATURE:
<223> OTHER INFORMATION: Synthetic construct

<400> SEQUENCE: 99

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120

<210> SEQ ID NO 100
<211> LENGTH: 121
<212> TYPE: PRT
<213> ORGANISM: Artificial Sequence
<220> FEATURE:
<223> OTHER INFORMATION: Synthetic construct

<400> SEQUENCE: 100

Glu Val Gln Leu Val Gln Ser Gly Ser Glu Leu Gly Arg Pro Gly Ser
1               5                   10                  15

Ser Val Lys Ile Ser Cys Lys Ala Ser Gly Tyr Thr Phe Thr Gly Tyr
            20                  25                  30

Ile Leu Ser Trp Val Arg Gln Ala Pro Gly Gln Gly Leu Glu Trp Ile
        35                  40                  45

Gly Trp Val Asp Pro Glu Tyr Gly Ser Thr Ser Ala Glu Lys Phe
    50                  55                  60

Lys Lys Arg Ala Thr Leu Ser Ala Asp Ile Ser Val Asn Thr Ala Tyr
65                  70                  75                  80

Leu Gln Leu Cys Ser Leu Lys Ala Glu Asp Thr Ala Thr Tyr Tyr Cys
                85                  90                  95

Thr Arg Tyr Tyr Asp Gly Tyr Tyr Arg Arg Trp Phe Ala Tyr Trp Gly
            100                 105                 110

Gln Gly Thr Leu Val Thr Val Ser Ser
        115                 120

<210> SEQ ID NO 101
<211> LENGTH: 17
<212> TYPE: PRT
<213> ORGANISM: Artificial Sequence

```
<220> FEATURE:
<223> OTHER INFORMATION: Synthetic construct

<400> SEQUENCE: 101

Ala Glu Tyr Phe Gln His Trp Gly Gln Gly Thr Leu Val Thr Val Ser
1               5                   10                  15

Ser

<210> SEQ ID NO 102
<211> LENGTH: 17
<212> TYPE: PRT
<213> ORGANISM: Artificial Sequence
<220> FEATURE:
<223> OTHER INFORMATION: Synthetic construct

<400> SEQUENCE: 102

Tyr Trp Tyr Phe Asp Leu Trp Gly Arg Gly Thr Leu Val Thr Val Ser
1               5                   10                  15

Ser

<210> SEQ ID NO 103
<211> LENGTH: 15
<212> TYPE: PRT
<213> ORGANISM: Artificial Sequence
<220> FEATURE:
<223> OTHER INFORMATION: Synthetic construct

<400> SEQUENCE: 103

Ala Phe Asp Val Trp Gly Gln Gly Thr Met Val Thr Val Ser Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic construct

<400> SEQUENCE: 104

Tyr Phe Asp Tyr Trp Gly Gln Gly Thr Leu Val Thr Val Ser Ser
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic construct

<400> SEQUENCE: 105

Asn Trp Phe Asp Ser Trp Gly Gln Gly Thr Leu Val Thr Val Ser Ser
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic construct

<400> SEQUENCE: 106

Tyr Tyr Gly Met Asp Val Trp Gly Gln Gly Thr Thr Val Thr Val Ser
1               5                   10                  15

Ser
```

<210> SEQ ID NO 107
<211> LENGTH: 107
<212> TYPE: PRT
<213> ORGANISM: Artificial Sequence
<220> FEATURE:
<223> OTHER INFORMATION: Synthetic construct

<400> SEQUENCE: 107

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro Ile
                85                  90                  95

Thr Phe Gly Gln Gly Thr Lys Val Glu Ile Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Synthetic construct

<400> SEQUENCE: 108

Val Ile Trp Met Thr Gln Ser Pro Ser Leu Leu Ser Ala Ser Thr Gly
1               5                   10                  15

Asp Arg Val Thr Ile Ser Cys Leu Ala Ser Glu Gly Ile Ser Asn Asn
            20                  25                  30

Leu Ala Trp His Gln Gln Lys Pro Gly Lys Ala Pro Glu Leu Leu Ile
        35                  40                  45

Tyr Gly Ala His Ser Leu His Asp Gly Val Pro Ser Arg Phe Ser Gly
    50                  55                  60

Ser Gly Ser Gly Thr Asp Tyr Thr Leu Thr Ile Ser Cys Leu Gln Ser
65                  70                  75                  80

Glu Asp Phe Ala Val Tyr Tyr Cys Gln Gln Gly Tyr Lys Tyr Pro Ile
                85                  90                  95

Thr Phe Gly Gln Gly Thr Lys Val Glu Ile Lys
            100                 105

<210> SEQ ID NO 109
<211> LENGTH: 107
<212> TYPE: PRT
<213> ORGANISM: Artificial Sequence
<220> FEATURE:
<223> OTHER INFORMATION: Synthetic construct

<400> SEQUENCE: 109

Asp Val Val Met Thr Gln Ser Pro Ala Ser Leu Pro Val Thr Leu Gly
1               5                   10                  15

Gln Pro Ala Ser Ile Ser Cys Arg Ser Ser Gln Asp Gly Asn Thr Tyr
            20                  25                  30

Leu Asn Trp Phe Gln Gln Arg Pro Gly Gln Ser Pro Arg Arg Leu Ile

```
                 35                  40                  45

Tyr Lys Val Ser Asn Trp Asp Ser Gly Val Pro Asp Arg Phe Ser Gly
         50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Met Gln Gly Thr His Trp Pro Ile
                 85                  90                  95

Thr Phe Gly Gln Gly Thr Lys Leu Glu Ile Lys
                100                 105

<210> SEQ ID NO 110
<211> LENGTH: 107
<212> TYPE: PRT
<213> ORGANISM: Artificial Sequence
<220> FEATURE:
<223> OTHER INFORMATION: Synthetic construct

<400> SEQUENCE: 110

Asp Ile Val Met Thr Gln Ser Pro Leu Ser Leu Pro Val Thr Leu Gly
 1               5                  10                  15

Pro Gln Val Ser Ile Ser Cys Leu Ala Ser Glu Gly Ile Ser Asn Asn
                 20                  25                  30

Leu Ala Trp His Gln Gln Arg Pro Gly Gln Ser Pro Gln Arg Leu Ile
             35                  40                  45

Tyr Gly Ala His Ser Leu His Asp Gly Val Pro Asp Arg Phe Ser Gly
         50                  55                  60

Ser Gly Ser Gly Thr Asp Tyr Thr Leu Lys Ile Ser Arg Val Glu Ala
 65                  70                  75                  80

Glu Asp Val Gly Val Tyr Tyr Cys Gln Gln Gly Tyr Lys Tyr Pro Ile
                 85                  90                  95

Thr Phe Gly Gln Gly Thr Lys Leu Glu Ile Lys
                100                 105

<210> SEQ ID NO 111
<211> LENGTH: 107
<212> TYPE: PRT
<213> ORGANISM: Artificial Sequence
<220> FEATURE:
<223> OTHER INFORMATION: Synthetic construct

<400> SEQUENCE: 111

Glu Ile Val Leu Thr Gln Ser Pro Gly Thr Leu Ser Leu Ser Pro Gly
 1               5                  10                  15

Glu Arg Val Thr Leu Ser Cys Arg Ala Ser Gln Val Ser Ser Ser Tyr
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Ile
                 85                  90                  95

Thr Phe Gly Pro Gly Thr Lys Val Asp Ile Lys
                100                 105

<210> SEQ ID NO 112
<211> LENGTH: 107
```

```
<212> TYPE: PRT
<213> ORGANISM: Artificial Sequence
<220> FEATURE:
<223> OTHER INFORMATION: Synthetic construct

<400> SEQUENCE: 112

Glu Ile Val Met Thr Gln Ser Pro Gly Thr Leu Ser Leu Ser Pro Gly
1               5                   10                  15

Glu Arg Ala Thr Ile Ser Cys Leu Ala Ser Glu Gly Ile Ser Asn Asn
            20                  25                  30

Leu Ala Trp His Gln Gln Lys Pro Gly Gln Ala Pro Gln Leu Leu Ile
        35                  40                  45

Tyr Gly Ala His Ser Leu His Asp Gly Ile Pro Asp Arg Phe Ser Gly
 50                  55                  60

Ser Gly Ser Gly Thr Asp Tyr Thr Leu Thr Ile Ser Arg Leu Glu Pro
65                  70                  75                  80

Glu Asp Phe Ala Val Tyr Tyr Cys Gln Gln Gly Tyr Lys Tyr Pro Ile
                85                  90                  95

Thr Phe Gly Pro Gly Thr Lys Val Asp Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic construct

<400> SEQUENCE: 113

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Asn Lys Asn Tyr
            20                  25                  30

Leu Ala Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Thr Pro Ile
                85                  90                  95

Thr Phe Gly Gly Gly Thr Lys Val Glu Ile Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: Synthetic construct

<400> SEQUENCE: 114

Asp Ile Val Met Thr Gln Ser Pro Asp Ser Leu Ala Val Ser Leu Gly
1               5                   10                  15

Glu Lys Ala Thr Ile Asn Cys Leu Ala Ser Glu Gly Ile Ser Asn Asn
            20                  25                  30

Leu Ala Trp His Gln Gln Lys Pro Gly Gln Pro Pro Gln Leu Leu Ile
        35                  40                  45

Tyr Gly Ala His Ser Leu His Asp Gly Val Pro Asp Arg Phe Ser Gly
```

```
                50                  55                  60
Ser Gly Ser Gly Thr Asp Tyr Thr Leu Thr Ile Ser Ser Leu Gln Ala
 65                  70                  75                  80

Glu Asp Val Ala Val Tyr Tyr Cys Gln Gln Gly Tyr Lys Tyr Pro Ile
                 85                  90                  95

Thr Phe Gly Gly Gly Thr Lys Val Glu Ile Lys
                100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic construct

<400> SEQUENCE: 115

Asp Val Val Met Thr Gln Ser Pro Ala Phe Leu Ser Val Thr Pro Gly
  1               5                  10                  15

Glu Lys Val Thr Ile Thr Cys Gln Ala Ser Glu Gly Ile Gly Asn Tyr
                 20                  25                  30

Leu Tyr Trp Tyr Gln Gln Lys Pro Asp Gln Ala Pro Lys Leu Leu Ile
             35                  40                  45

Lys Tyr Ala Ser Gln Ser Ile Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Gln Gly Asn Lys His Pro Ile
                 85                  90                  95

Thr Phe Gly Gly Gly Thr Lys Val Glu Ile Lys
                100                 105

<210> SEQ ID NO 116
<211> LENGTH: 107
<212> TYPE: PRT
<213> ORGANISM: Artificial Sequence
<220> FEATURE:
<223> OTHER INFORMATION: Synthetic construct

<400> SEQUENCE: 116

Asp Ile Val Met Thr Gln Ser Pro Ala Phe Leu Ser Val Thr Pro Gly
  1               5                  10                  15

Glu Lys Val Thr Ile Thr Cys Leu Ala Ser Glu Gly Ile Ser Asn Asn
                 20                  25                  30

Leu Ala Trp His Gln Gln Lys Pro Asp Gln Ala Pro Gln Leu Leu Ile
             35                  40                  45

Tyr Gly Ala His Ser Leu His Asp Gly Val Pro Ser Arg Phe Ser Gly
 50                  55                  60

Ser Gly Ser Gly Thr Asp Tyr Thr Leu Thr Ile Ser Ser Leu Glu Ala
 65                  70                  75                  80

Glu Asp Ala Ala Val Tyr Tyr Cys Gln Gln Gly Tyr Lys Tyr Pro Ile
                 85                  90                  95

Thr Phe Gly Gly Gly Thr Lys Val Glu Ile Lys
                100                 105

<210> SEQ ID NO 117
<211> LENGTH: 12
<212> TYPE: PRT
<213> ORGANISM: Artificial Sequence
<220> FEATURE:
```

```
<223> OTHER INFORMATION: Synthetic construct

<400> SEQUENCE: 117

Trp Thr Phe Gly Gln Gly Thr Lys Val Glu Ile Lys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Synthetic construct

<400> SEQUENCE: 118

Tyr Thr Phe Gly Gln Gly Thr Lys Leu Glu Ile Lys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic construct

<400> SEQUENCE: 119

Phe Thr Phe Gly Pro Gly Thr Lys Val Asp Ile Lys
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic construct

<400> SEQUENCE: 120

Leu Thr Phe Gly Gly Gly Thr Lys Val Glu Ile Lys
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic construct

<400> SEQUENCE: 121

Ile Thr Phe Gly Gln Gly Thr Arg Leu Glu Ile Lys
1               5                   10

<210> SEQ ID NO 122
<211> LENGTH: 5
<212> TYPE: PRT
<213> ORGANISM: Artificial Sequence
<220> FEATURE:
<223> OTHER INFORMATION: Synthetic construct

<400> SEQUENCE: 122

Gly Gly Gly Gly Ser
1               5

<210> SEQ ID NO 123
<211> LENGTH: 15
<212> TYPE: PRT
<213> ORGANISM: Artificial Sequence
<220> FEATURE:
<223> OTHER INFORMATION: Synthetic construct
```

```
<400> SEQUENCE: 123

Gly Gly Gly Gly Ser Gly Gly Gly Gly Ser Gly Gly Gly Gly Ser
1               5                   10                  15

<210> SEQ ID NO 124
<211> LENGTH: 6
<212> TYPE: PRT
<213> ORGANISM: Artificial Sequence
<220> FEATURE:
<223> OTHER INFORMATION: Synthetic construct

<400> SEQUENCE: 124

His His His His His His
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic construct

<400> SEQUENCE: 125

Asp Tyr Lys Asp Asp Asp Asp Lys
1               5
```

ANTI-INTEGRIN β1 ANTIBODY COMPOSITIONS AND METHODS OF USE THEREOF

CROSS REFERENCE TO RELATED APPLICATION(S)

This application claims the benefit under 35 USC § 119(e) to U.S. Application Ser. No. 61/746,023, filed Dec. 26, 2012. The disclosure of the prior application is considered part of and is incorporated by reference in its entirety in the disclosure of this application.

BACKGROUND OF THE INVENTION

Field of the Invention

The present invention relates generally to the field of immunology, and more specifically to anti-integrin antibodies and methods of use thereof.

Background Information

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them including breast, lung, colorectal, and prostate, account for over half of all new cases.

Breast cancer is the most common cancer in women, with an estimate 12% of women at risk of developing the disease during their lifetime. Although mortality rates have decreased due to earlier detection and improved treatments, breast cancer remains a leading cause of death in middle-aged women. Furthermore, metastatic breast cancer is still an incurable disease. On presentation, most patients with metastatic breast cancer have only one or two organ systems affected, but as the disease progresses, multiple sites usually become involved. The most common sites of metastatic involvement are locoregional recurrences in the skin and soft tissues of the chest wall, as well as in axilla and supraclavicular areas. The most common site for distant metastasis is the bone (30-40% of distant metastasis), followed by the lungs and liver. Although only approximately 1-5% of women with newly diagnosed breast cancer have distant metastasis at the time of diagnosis, approximately 50% of patients with local disease eventually relapse with metastasis within five years. At present the median survival from the manifestation of distant metastases is about three years.

Current methods of diagnosing and staging breast cancer include the tumor-node-metastasis (TNM) system that relies on tumor size, tumor presence in lymph nodes, and the presence of distant metastases as described in the American Joint Committee on Cancer: AJCC Cancer Staging Manual. Philadelphia, Pa.: Lippincott-Raven Publishers, 5th ed., 1997, pp 171-180, and in Harris, J R: "Staging of breast carcinoma" in Harris, J. R., Hellman, S., Henderson, I. C, Kinne D. W. (eds.): Breast Diseases. Philadelphia, Lippincott, 1991. These parameters are used to provide a prognosis and select an appropriate therapy. The morphologic appearance of the tumor may also be assessed but because tumors with similar histopathologic appearance can exhibit significant clinical variability, this approach has serious limitations. Finally, assays for cell surface markers can be used to divide certain tumors types into subclasses. For example, one factor considered in the prognosis and treatment of breast cancer is the presence of the estrogen receptor (ER) as ER-positive breast cancers typically respond more readily to hormonal therapies such as tamoxifen or aromatase inhibitors than ER-negative tumors. Yet these analyses, though useful, are only partially predictive of the clinical behavior of breast tumors, and there is much phenotypic diversity present in breast cancers that current diagnostic tools fail to detect and current therapies fail to treat.

Prostate cancer is the most common cancer in men in the developed world, representing an estimated 33% of all new cancer cases in the U.S., and is the second most frequent cause of death. Since the introduction of the prostate specific antigen (PSA) blood test, early detection of prostate cancer has dramatically improved survival rates, and the five year survival rate for patients with local and regional stage prostate cancers at the time of diagnosis is nearing 100%. Yet more than 50% of patients will eventually develop locally advanced or metastatic disease.

Currently radical prostatectomy and radiation therapy provide curative treatment for the majority of localized prostate tumors. However, therapeutic options are very limited for advanced cases. For metastatic disease, androgen ablation with luteinising hormone-releasing hormone (LHRH) agonist alone or in combination with anti-androgens is the standard treatment. Yet despite maximal androgen blockage, the disease nearly always progresses with the majority developing androgen-independent disease. At present there is no uniformly accepted treatment for hormone refractory prostate cancer, and chemotherapeutic regimes are commonly used.

Lung cancer is the most common cancer worldwide, the third most commonly diagnosed cancer in the United States, and by far the most frequent cause of cancer deaths. Cigarette smoking is believed responsible for an estimated 87% of all lung cancers making it the most deadly preventable disease. Lung cancer is divided into two major types that account for over 90% of all lung cancers: small cell lung cancer (SCLC) and non-small cell lung cancer (NSCLC). SCLC accounts for 15-20% of cases and is characterized by its origin in large central airways and histological composition of sheets of small cells with little cytoplasm. SCLC is more aggressive than NSCLC, growing rapidly and metastasizing early and often. NSCLC accounts for 80-85% of all cases and is further divided into three major subtypes based on histology: adenocarcinoma, squamous cell carcinoma (epidermoid carcinoma), and large cell undifferentiated carcinoma.

Lung cancer typically presents late in its course, and thus has a median survival of only 6-12 months after diagnosis and an overall 5 year survival rate of only 5-10%. Although surgery offers the best chance of a cure, only a small fraction of lung cancer patients are eligible with the majority relying on chemotherapy and radiotherapy. Despite attempts to manipulate the timing and dose intensity of these therapies, survival rates have increased little over the last 15 years.

Colorectal cancer is the third most common cancer and the fourth most frequent cause of cancer deaths worldwide. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Colorectal carcinoma has a tendency to invade locally by circumferential growth and elsewhere by lymphatic, hematogenous, transperitoneal, and perineural spread. The most common site of extralymphatic involvement is the liver, with the lungs the most frequently affected extraabdominal organ. Other sites of hematogenous spread include the bones, kidneys, adrenal glands, and brain.

The current staging system for colorectal cancer is based on the degree of tumor penetration through the bowel wall and the presence or absence of nodal involvement. This staging system is defined by three major Duke's classifications: Duke's A disease is confined to submucosa layers of colon or rectum; Duke's B disease has tumors that invade through muscularis propria and can penetrate the wall of the colon or rectum; and Duke's C disease includes any degree of bowel wall invasion with regional lymph node metastasis. While surgical resection is highly effective for early stage colorectal cancers, providing cure rates of 95% in Duke's A patients, the rate is reduced to 75% in Duke's B patients and the presence of positive lymph node in Duke's C disease predicts a 60% likelihood of recurrence within five years. Treatment of Duke's C patients with a post surgical course of chemotherapy reduces the recurrence rate to 40%-50%, and is now the standard of care for these patients.

Epithelial carcinomas of the head and neck arise from the mucosal surfaces in the head and neck area and are typically squamous cell in origin. This category includes tumors of the paranasal sinuses, the oral cavity, and the nasopharynx, oropharynx, hypopharynx, and larynx.

The annual number of new cases of head and neck cancers in the United States is approximately 40,000 per year, accounting for about 5 percent of adult malignancies. Head and neck cancers are more common in some other countries, and the worldwide incidence probably exceeds half a million cases annually. In North American and Europe, the tumors usually arise from the oral cavity, oropharynx, or larynx, whereas nasopharyneal cancer is more common in the Mediterranean countries and in the Far East.

Traditional modes of therapy (radiation therapy, chemotherapy, and hormonal therapy), while useful, have been limited by the emergence of treatment-resistant cancer cells. Clearly, new approaches are needed to identify targets for treating head and neck cancer and cancer generally.

Pancreatic cancer is a malignant neoplasm originating from transformed cells arising in tissues forming the pancreas. The most common type of pancreatic cancer, accounting for 95% of these tumors, is adenocarcinoma (tumors exhibiting glandular architecture on light microscopy) arising within the exocrine component of the pancreas. A minority arise from islet cells, and are classified as neuroendocrine tumors. Pancreatic cancer is the fourth most common cause of cancer-related deaths in the United States and the eighth worldwide.

Glioblastoma multiforme (GBM) is the most common malignant brain tumor in adults with a median survival of less than one year with maximal therapy. To date, only three drugs have been approved by the FDA for GBM treatment and overall survival has not improved in over 25 years.

Integrins are cell-adhesion molecules that are responsible for mechanosensing the microenvironment and eliciting extracellular-matrix (ECM)-induced signaling in both normal and pathological states such as inflammation and cancer. Importantly, integrins lie at the interface of the cell and microenvironment, playing a key role in tumor progression and regulating growth and survival pathways. Upregulation of many types of integrins has been associated with epithelial malignancies, particularly during the processes of invasion, metastasis, and angiogenesis. Importantly, β1 integrins which coordinate much broader functional activities such as inflammation, proliferation, adhesion, and invasion have recently been implicated in therapeutic resistance in multiple solid cancer models and hematopoietic malignancies. Importantly, this β1 integrin mediated resistance is thought to occur at the level of the tumor cells themselves. In addition to the above, β1 integrin has important functions during tumor vascularization such as VEGF-dependent and VEGF-independent angiogenesis by promoting migration of vascular endothelial cells Inhibition of β1 integrin overcomes resistance to antiangiogenesis therapy via multiple potential mechanisms: (1) preventing vessel cooption (and/or growth/invasion upon any classical ECM substrate; (2) reducing viability of tumor cells after insults such as ionizing radiation; (3) directly inhibiting tumor cell proliferation; (4) directly inhibiting the vascularization process; and (5) inhibiting the aggressive mesenchymal phenotype, including spheroidal growth, typically seen after the establishment of therapy resistance.

Anti-integrin β1 compositions, such as integrin β1 targeted antibodies may also be important in for immunological/inflammatory diseases and disorders given the role of integrin β1 in broader functional activities as discussed above. Further, diseases and disorders which may be targeted through the integrin β1 pathway include multiple sclerosis, Crohn's disease, rheumatoid arthritis, inflammatory bowel disease and the like. Similarly, it is to be expected that certain eye related diseases may be targeted including wet age-related macular degeneration (AMD).

SUMMARY OF THE INVENTION

The present invention is based on the generation of humanized antibodies having human framework sequences which specifically bind integrin β1. Integrin β1 is known to be a protein over-expressed in solid tumors, and thus as a cancer cell marker useful in the characterization, study, diagnosis, and treatment of cancer. In addition, integrin β1 has been demonstrated to drive cancer resistance to conventional (e.g., chemotherapy and ionizing radiation) and targeted (e.g., trastuzumab, bevicizumab, lapatinib) therapies by orchestrating growth and survival signals from the tumor microenvironment. Humanization efforts have been limited in the past by the number of human frameworks available. This invention meets the need for additional human framework sequences for an antibody the specifically binds Integrin β1.

In one embodiment, the present invention provides a humanized antibody which specifically binds integrin β1. The antibody includes a heavy chain variable (VH) region and a light chain variable (VL) region, wherein the VH region has less than about 97%, 96% or 95% identity to a VH region having an amino acid sequence as set forth in SEQ ID NO:2, and wherein the VL region has less than about 97%, 96% or 95% identity to a VL region having an amino acid sequence as set forth in SEQ ID NO:4.

In another embodiment, the VH region has more than 75%, 80%, 85%, 90%, 95% or 99% identity to a VH region having an amino acid sequence as set forth in SEQ ID NO:6, SEQ ID NO:8, SEQ ID NO:10, SEQ ID NO:12, SEQ ID NO:14, SEQ ID NOs:29-43 and SEQ ID NOs:91-100. In embodiments the VL region has more than 75%, 80%, 85%, 90%, 95% or 99% identity to a VL region having an amino acid sequence as set forth in SEQ ID NO:16, SEQ ID NO:18, SEQ ID NO:20, SEQ ID NO:22, SEQ ID NOs:44-57 and SEQ ID NOs:107-116.

In another embodiment, the antibody has CDRs of the VH and VL regions from a donor antibody, such as OS2966. In embodiments, the CDRs of the VH region have amino acid sequences as set forth in SEQ ID NO:23, SEQ ID NO:24 and SEQ ID NO:25, and the CDRs of the VL region have amino acid sequences as set forth in SEQ ID NO:26, SEQ ID NO:27 and SEQ ID NO:28.

In one aspect, the invention provides an antibody which includes VH and VL regions of the present invention.

In another aspect, the invention provides a nucleic acid molecule encoding the antibody of the present invention.

In another aspect, the invention provides a vector which includes a nucleic acid molecule of the present invention.

In another aspect, the invention provides an isolated host cell which includes the vector of the present invention.

In another aspect, the invention provides pharmaceutical compositions. In one embodiment the pharmaceutical composition includes the antibody of the present invention and a pharmaceutically acceptable carrier. In one embodiment the pharmaceutical composition includes the nucleic acid molecule of the present invention and a pharmaceutically acceptable carrier.

In another aspect, the invention provides an immunoconjugate including the antibody of the present invention linked to detection or therapeutic moiety.

In another aspect, the invention provides a chimeric protein including the antibody of the present invention operably linked to a separate peptide, such as a cytokine.

In another embodiment, the invention provides a method of treating a disease in a subject. In embodiments, the method includes administering to the subject the antibody of the present invention, the nucleic acid molecule of the present invention, the pharmaceutical composition of the present invention, the immunoconjugate of the present invention, or the chimeric protein of the present invention, thereby treating the disease. In one embodiment the disease is a cell proliferative disorder, such as cancer.

In another embodiment, the invention provides a method of detecting a disease in a subject. The method includes contacting the antibody or immunoconjugate of the present invention with a sample from the subject; detecting the level of integrin β1 via specific binding with integrin β1; and comparing the detected level of integrin β1 to that of integrin β1 in a normal sample, wherein an increased level of integrin β1 in the sample from the subject as compared to the normal sample is indicative of a disease.

In another embodiment, the invention provides a VH region having more than 75%, 80%, 85%, 90%, 95% or 99% identity to a VH region having an amino acid sequence as set forth in SEQ ID NO:6, SEQ ID NO:8, SEQ ID NO:10, SEQ ID NO:12, SEQ ID NO:14, SEQ ID NOs:29-43 and SEQ ID NOs:91-100.

In another embodiment, the invention provides a VL region having more than 75%, 80%, 85%, 90%, 95% or 99% identity to a VL region having an amino acid sequence as set forth in SEQ ID NO:16, SEQ ID NO:18, SEQ ID NO:20, SEQ ID NO:22, SEQ ID NOs:44-57 and SEQ ID NOs:107-116.

BRIEF DESCRIPTION OF THE DRAWINGS

FIG. 1 is a pictorial representation depicting nucleic acid and amino acid sequences of the VH region of antibody OS2966 produced by hybridoma OS2966.

FIG. 3 is a pictorial representation depicting analysis of CDRs of antibody OS2966 produced by hybridoma OS2966 which are utilized in the VH and VL regions of the antibody of the present invention.

FIG. 4 is a pictorial representation depicting the amino acid sequences of CDRs of antibody OS2966 produced by hybridoma which are utilized in the VH and VL regions of the antibody of the present invention.

FIG. 5 is a pictorial representation depicting nucleic acid and amino acid sequences of the VH region of the antibody of the present invention in one embodiment. Conserved CDRs are underlined.

FIG. 6 is a pictorial representation depicting nucleic acid and amino acid sequences of the VH region of the antibody of the present invention in one embodiment. Conserved CDRs are underlined.

FIG. 7 is a pictorial representation depicting nucleic acid and amino acid sequences of the VH region of the antibody of the present invention in one embodiment. Conserved CDRs are underlined.

FIG. 8 is a pictorial representation depicting nucleic acid and amino acid sequences of the VH region of the antibody of the present invention in one embodiment. Conserved CDRs are underlined.

FIG. 9 is a pictorial representation depicting nucleic acid and amino acid sequences of the VH region of the antibody of the present invention in one embodiment. Conserved CDRs are underlined.

FIG. 10 is a pictorial representation depicting nucleic acid and amino acid sequences of the VL region of the antibody of the present invention in one embodiment. Conserved CDRs are underlined.

FIG. 11 is a pictorial representation depicting nucleic acid and amino acid sequences of the VL region of the antibody of the present invention in one embodiment. Conserved CDRs are underlined.

FIG. 12 is a pictorial representation depicting nucleic acid and amino acid sequences of the VL region of the antibody of the present invention in one embodiment. Conserved CDRs are underlined.

FIG. 13 is a pictorial representation depicting nucleic acid and amino acid sequences of the VL region of the antibody of the present invention in one embodiment. Conserved CDRs are underlined.

FIG. 16 is a pictorial representation depicting sequence analysis and alignment of humanized J regions (VH) of the invention corresponding to alignments shown in FIG. 15. Sequences are as follows: J1 is SEQ ID NO:101; J2 is SEQ ID NO:102; J3 is SEQ ID NO:103; J4 is SEQ ID NO:104; J5 is SEQ ID NO:105; and J6 is SEQ ID NO:106.

FIG. 17 is a pictorial representation depicting sequence analysis and alignment of humanized VL chains of the invention with comparison to VL of antibody OS2966 (SEQ ID NO:4). Sequences are as follows: OS2966 is SEQ ID NO:4; Variant 1 is SEQ ID NO:16; Variant 2 is SEQ ID NO:18; Variant 3 is SEQ ID NO:20; Variant 4 is SEQ ID NO:22; Variant 5 is SEQ ID NO:44; Variant 6 is SEQ ID NO:45; Variant 7 is SEQ ID NO:46; Variant 8 is SEQ ID NO:47; Variant 9 is SEQ ID NO:48; Variant 10 is SEQ ID NO:49; Variant 11 is SEQ ID NO:50; Variant 12 is SEQ ID NO:51; Variant 13 is SEQ ID NO:52; VkI is SEQ ID NO:107; Variant 14 is SEQ ID NO:108; VkII is SEQ ID NO:109; Variant 15 is SEQ ID NO:110; VkIII is SEQ ID NO:111; Variant 16 is SEQ ID NO:112; VkIV is SEQ ID NO:113; Variant 17 is SEQ ID NO:114; VkVI is SEQ ID NO:115; and Variant 18 is SEQ ID NO:116.

FIG. 18 is a pictorial representation depicting sequence analysis and alignment of humanized J regions (kappa light chains) of the invention corresponding to alignments shown in FIG. 17. Sequences are as follows: J1 is SEQ ID NO:117; J2 is SEQ ID NO:118; J3 is SEQ ID NO:119; J4 is SEQ ID NO:120; and J5 is SEQ ID NO:121.

FIG. 19 is a pictorial representation depicting codon usage of the VH and VL chains of the present invention.

FIG. 25A utilizes PANC-1 human pancreatic cancer. FIG. 25B utilizes PANC-1 human pancreatic cancer. FIG. 25B utilizes PANC-1 human pancreatic cancer. FIG. 25C utilized MDA-MB-231 human triple negative breast cancer. FIG. 25D utilizes AsPC-1 human pancreatic cancer.

FIG. 26A is a series of images at 10× magnification of plates demonstrating attenuation of migration into the wound in OS2966 and composite human variants (H1, H2, H3) treated wells. FIG. 26B is a graph of quantitation of cell free area for each condition (performed in triplicate and repeated).

FIG. 27A is a series of images at 10× magnification of plates demonstrating attenuation of vascular tube formation in OS2966 and composite human variant (H1, H2, H3) treated wells. FIG. 27B is a series of graphs of quantitation of closed unit formation for each condition (performed in at least triplicate and repeated with endothelial progenitor cells).

FIG. 28A is a graph showing group tumor mean volume per time. FIG. 28B is an image of a western blot.

FIG. 30A is a graph showing group tumor mean volume per time. FIG. 30B is a graph showing group tumor mean volume per time. FIG. 30C is an image of a western blot.

FIG. 31A is a graph showing group tumor mean volume per time. FIG. 3B is an image of a blot.

FIG. 32A is a histogram. FIG. 32B is a summary of healthy donor T cell proliferation responses to the donor cohort.

DETAILED DESCRIPTION OF THE INVENTION

Figure 14:
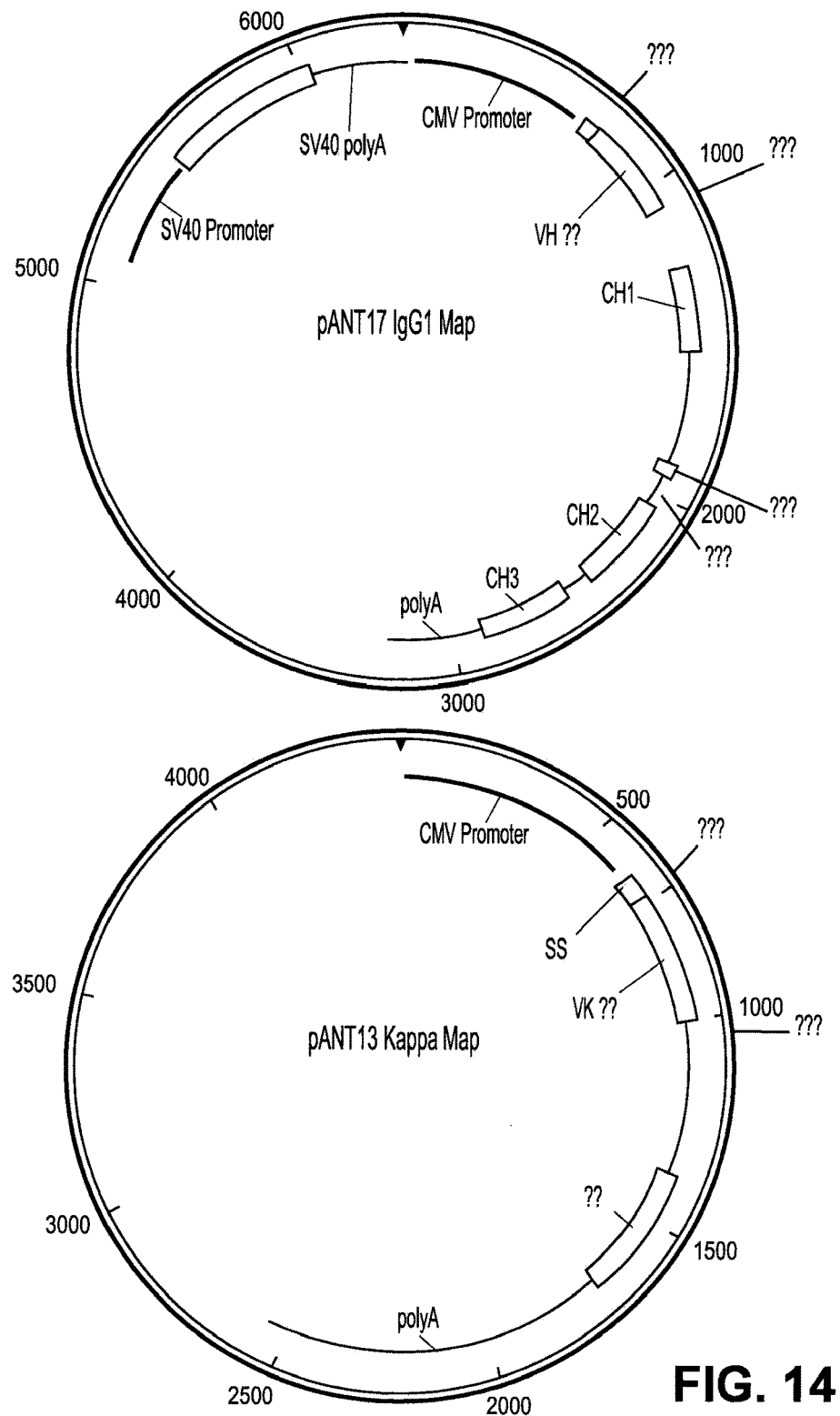
FIG. 14 is a schematic diagram of vectors.

The present invention provides human VH and VL framework sequences and nucleic acid sequences that encode them. Such sequences are used, for example, to provide frameworks for grafting CDRs from a donor antibody, e.g., a rodent antibody. Thus, an antibody comprising a VH and/or VL framework of the invention with the binding specificity of a donor antibody can be created.

The invention also provides humanized antibodies having the specificity of an antibody termed OS2966, e.g., specific binding to integrin β1, via CDRs of murine OS2966 provided in the human VH and VL framework regions set forth in SEQ ID NOs: 6, 8, 10, 12, 14, 16, 18, 20, 22, 29-57, 91-100 and 107-116.

The humanized antibodies of the invention are used for a variety of therapeutic and diagnostic purposes as described herein. Uses include diagnosing and treating diseases such as cancer.

Before the present compositions and methods are described, it is to be understood that this invention is not limited to the particular device, methods, and experimental conditions described, as such devices, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the composition" or "the method" includes one or more compositions and methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "integrin β1" is synonymous with CD29 and includes reference to a protein encoded by the ITGB1 gene. Integrin β1 is associated with late antigen receptors and is known to conjoin with a number of alpha subunits including alpha-1 though alpha-9, for example, complexing to alpha-3 subunit creates α3β1 complex that reacts to such molecules as netrin-1 and reelin.

As used herein, the term "anti-integrin β1" in reference to an antibody, refers to an antibody that specifically binds integrin β1.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., Fundamental Immunology (Paul ed., 3d ed. 1993). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries. The term antibody also includes bivalent or bispecific molecules, diabodies, triabodies, and tetrabodies. Bivalent and bispecific molecules are known in the art.

References to "VH" or a "VH" refer to the variable region of an immunoglobulin heavy chain, including an Fv, scFv, a disulfilde-stabilized Fv (dsFv) or Fab. References to "VL" or a "VL" refer to the variable region of an immunoglobulin light chain, including of an Fv, scFv, dsFv or Fab.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. The numbering of the light and heavy chain variable regions described herein is in accordance with Kabat (see, e.g., Johnson et al., (2001) "Kabat Database and its applications: future directions" Nucleic Acids Research, 29: 205-206; and the Kabat Database of Sequences of Proteins of Immunological Interest, Feb. 22, 2002 Dataset) unless otherwise indicated.

The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol. 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl. Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

Exemplary framework and CDR sequences for human VH and VL regions disclosed herein are shown in FIG. 4.

"OS2966" refers to a murine IgG1 antibody that specifically binds to human integrin β1. OS2966 is commercially available (under a different designation) from several sources, such as the Developmental Studies Hybridoma Bank of the University of Iowa. The heavy and light chains of OS2966 have been cloned. The nucleotide and amino acid sequences of the OS2966 VH region are set forth in SEQ ID NO:1 and SEQ ID NO:2, respectively. The nucleotide and amino acid sequences of the OS2966 VL region are set forth in SEQ ID NO:3 and SEQ ID NO:4, respectively. The OS2966 CDRs as designated for the exemplary humanized antibodies described herein are set forth in SEQ ID NOs: 23-28 and shown in FIG. 4.

A "humanized antibody" refers to an antibody that comprises a donor antibody binding specificity, i.e., the CDR regions of a donor antibody, typically a mouse monoclonal antibody, grafted onto human framework sequences. A "humanized antibody" as used herein binds to the same epitope as the donor antibody and typically has at least 25% of the binding affinity. An exemplary assay for binding affinity is described in Example 5. Methods to determine whether the antibody binds to the same epitope are well known in the art, see, e.g., Harlow & Lane, Using Antibodies, A Laboratory Manual, Cold Spring Harbor Laboratory Press, 1999, which discloses techniques to epitope mapping or alternatively, competition experiments, to determine whether an antibody binds to the same epitope as the donor antibody. A humanized antibody that comprises a novel framework region provided in the invention.

A "VH" or "VL" "region" or "framework" of the invention refers to the a VH or VL amino acid sequence that has at least 70% identity, often, at least 75%, 80%, 85%, 90%, 95%, 96%, 97%, 98%, or 99% identity, to an amino acid sequence set forth in SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NOs:29-57, SEQ ID NOs:91-100, or SEQ ID NOs:107-116. A "framework" of a VH or VL chain refers to the framework regions of the chain not including the CDRs. The term as applied to each chain encompasses all of the framework regions.

A "humanized anti-integrin β1 antibody" refers to a humanized antibody comprising a human framework sequence that has the binding specificity of the murine OS2966 grafted to that framework. A CDR of a humanized anti-integrin β1 antibody of the invention has at least 85%, more typically at least 90%, 95%, 96%, 97%, 98%, or 99% identity to a CDR of the heavy and light chain sequences set forth in SEQ ID NO:2 and SEQ ID NO:4, respectively. CDRs of the VH region are set forth in SEQ ID NO:23, SEQ ID NO:24, and SEQ ID NO:25. CDRs of the VH region are set forth in SEQ ID NO:26, SEQ ID NO:27, and SEQ ID NO:28.

In one aspect, the invention provides composite humanized antibodies. Composite human antibody technology generates humanized non-immunogenic antibodies by avoiding T cell epitopes (deimmunisation) in variable region (V region) sequences (EP2,388,871). Unlike other humanization technologies that use single human V region frameworks as 'acceptors' for complimentarity-determining regions (CDRs) from the starting antibody (typically murine), Composite Human Antibodies™ comprise multiple sequence segments (composites') derived from V regions of unrelated human antibodies. The key properties of Composite Human Antibodies are as follows:

Sequence segments derived from databases of unrelated human V regions are selected after determining amino acids which are considered critical for antigen binding of the starting antibody. All selected sequence segments derived from human V region databases are filtered for the presence of potential T cell epitopes using Antitope's in silico tools. Composite Human Antibodies™ retain affinity and specificity better than standard humanized antibodies due to the close fit of human sequence segments with all sections of the starting antibody V regions. Composite Human Antibodies™ are depleted of T cell epitopes and therefore considered both humanized and deimmunised.

In one embodiment, the invention antibodies are prepared by identifying candidate residues in the framework region to be mutated at specific sites within T cell epitopes. Invention antibodies may exhibit altered binding affinity and/or altered immunogenicity as compared to donor antibodies.

Methods known in the art can be used to map T cell epitopes within a protein sequence. For example, EpiScreen™ (EP1989544, Antitope, UK) is used to map T cell epitopes within a protein sequence to determine potential for immunogenicity, which is based on the number and potency of T cell epitopes within a sequence. EpiScreen™ T cell epitope mapping typically uses CD8+ T cell depleted PBMCs from a minimum of 50 HLA-typed donors (selected to represent the human population of interest). Typically, 15mer peptides with 12 amino acid overlaps spanning a protein sequence are analyzed in a large number of replicate cultures for in vitro CD4+ T cell stimulation by 3H TdR incorporation. CD4+ T cell stimulation is often detected in two or three adjacent and overlapping peptides since the core 9mer that binds the MHC class II binding groove will be present in more than one peptide sequence. After the accurate identification of peptides that stimulate CD4+ T cells in vitro, in silico technologies can be used to design epitope-depleted (deimmunized) variants by determining the precise location of core 9mer sequences and the location of key MHC class II anchor residues.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for the stabilization of the variable domains without interfering with the proper folding and creation of an active binding site. A single chain humanized antibody of the invention, e.g., humanized anti-integrin β1 antibody, may bind as a monomer. Other exemplary single chain antibodies may form diabodies, triabodies, and tetrabodies. (See, e.g., Hollinger et al., 1993, supra). Further the humanized antibodies of the invention, e.g., humanized anti-integrin β1 antibody may also form one component of a "reconstituted" antibody or antibody fragment, e.g., a Fab, a Fab' monomer, a F(ab')'2 dimer, or an whole immunoglobulin molecule. Thus, a humanized antibody of the present invention may further comprise a human Fc region.

"Join" or "link" or "conjugate" refers to any method known in the art for functionally connecting protein domains, including without limitation recombinant fusion with or without intervening domains, intein-mediated fusion, non-covalent association, and covalent bonding, e.g., disulfide bonding, peptide bonding; hydrogen bonding; electrostatic bonding; and conformational bonding, e.g., antibody-antigen, and biotin-avidin associations. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

The term "effector moiety" means the portion of an immunoconjugate intended to have an effect on a cell targeted by the targeting moiety or to identify the presence of the immunoconjugate. Thus, the effector moiety can be, for example, a therapeutic moiety, such as a cytotoxic agent or drug, or a detectable moiety, such as a fluorescent label.

A "therapeutic moiety" is the portion of an immunoconjugate intended to act as a therapeutic agent.

The term "therapeutic agent" includes any number of compounds currently known or later developed to act as chemotherapeutic agents, anti-neoplastic compounds, anti-inflammatory compounds, anti-infective compounds, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

The terms "effective amount" or "amount effective to" or "therapeutically effective amount" refers to an amount sufficient to induce a detectable therapeutic response in the subject. Preferably, the therapeutic response is effective in reducing the proliferation of cancer cells or in inhibiting the growth of cancer cells present in a subject. Assays for determining therapeutic responses are well known in the art.

The term "immunoconjugate" refers to a composition comprising an antibody linked to a second molecule such as a detectable label or effector molecule. Often, the antibody is linked to the second molecule by covalent linkage.

In the context of an immunoconjugate, a "detectable label" or "detectable moiety" refers to, a portion of the immunoconjugate which has a property rendering its presence detectable. For example, the immunoconjugate may be labeled with a radioactive isotope which permits cells in which the immunoconjugate is present to be detected in immunohistochemical assays. A "detectable label" or a "detectable moiety" is a composition detectable by spectroscopic, photochemical, biochemical, immunochemical, chemical, or other physical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins which can be made detectable, e.g., by incorporating a radiolabel into the peptide or used to detect antibodies specifically reactive with the peptide.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0.degree. C. and below 50.degree. C. Osmolarity is within the range that is supportive of cell viability and proliferation.

The term "specifically binds," "binding specificity," "specifically binds to an antibody" or "specifically immunoreactive with," when referring to an epitope, refers to a binding reaction which is determinative of the presence of the epitope in a heterogeneous population of proteins and other biologics. Thus, under designated immunoassay conditions, the specified antibodies bind to a particular epitope at least two times the background and more typically more than 10 to 100 times background. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, ANTIBODIES, A LABORATORY MANUAL, Cold Spring Harbor Press, New York (1988) and Harlow & Lane, USING ANTIBODIES, A LABORATORY MANUAL, Cold Spring Harbor Press, New York (1999), for a description of immunoassay formats and conditions that can be used to determine specific immunoreactivity. As used herein, "specifically binds" means that an antibody binds to a protein with a Kd of at least about 0.1 mM, at least about 1 µM, at least about 0.1 µM or better, or 0.01 µM or better.

"Nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). As appreciate by one of skill in the art, the complement of a nucleic acid sequence can readily be determined from the sequence of the other strand. Thus, any particular nucleic acid sequence set forth herein also discloses the complementary strand.

"Polypeptide," "peptide" and "protein" are used interchangeably herein to refer to a polymer of amino acid residues. The terms apply to naturally occurring amino acid polymers, as well as, amino acid polymers in which one or more amino acid residue is an artificial chemical mimetic of a corresponding naturally occurring amino acid.

Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Conservatively modified variants" applies to both nucleic acid and amino acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. "Tertiary structure" refers to the complete three dimensional structure of a polypeptide monomer. Domains are portions of a polypeptide that form a compact unit of the polypeptide and are typically 50 to 350 amino acids long. Typical domains are made up of sections of lesser organization such as stretches of β-sheet and α-helices. Quaternary structure" refers to the three dimensional structure formed by the noncovalent association of independent tertiary units.

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local alignment algorithm of Smith & Waterman, Adv. Appl. Math. 2:482 (1981), by the global alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)). The Smith & Waterman alignment with the default parameters are often used when comparing sequences as described herein.

Another example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403410 (1990), respectively. BLAST and BLAST 2.0 are used, typically with the default parameters, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff& Henikoff (1989) Proc. Natl. Acad. Sci. USA 89:10915)). For the purposes of this invention, the BLAST2.0 algorithm is used with the default parameters.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is cloned in frame, the protein it encodes will be expressed as part of the coat protein. Thus, libraries of nucleic acid sequences, such as that of an antibody repertoires made from the gene segments encoding the entire B cell repertoire of one or more individuals, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn (1996) Curr. Opin. Biotechnol. 7:547-553). See, e.g., description of phage display libraries, below.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, and the like) with the desired specificity, affinity, and capability while the constant regions are homologous to the sequences in antibodies derived from another (usually human) to avoid eliciting an immune response in that species.

The term "epitope" or "antigenic determinant" or "antigen determination region" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1-125 label (see Morel et al., Molec. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Antibodies of the present invention, e.g, VH polypeptides, VL polypeptides, or single chain antibodies, may be generated using routine techniques in the field of recombinant genetics. Basic texts disclosing the general methods used in this invention include Sambrook & Russell, Molecular Cloning, A Laboratory Manual (3d ed. 2001) and Current Protocols in Molecular Biology (Ausubel et al., eds., 1999).

Humanized antibodies of the invention may be generated by grafting the specificity, i.e., the antigen binding loops, of a donor antibody, typically a murine antibody, to a human framework. The framework regions of the human light chain and heavy chains provided herein can readily be determined by the practitioner. The position numbers of the heavy and light chains are designated in accordance with common numbering schemes, e.g., the Kabat and Chothia numbering scheme. The Chothia number scheme is identical to the Kabat scheme, but places the insertions in CDR-L1 and CDR-H1 at structurally different positions. Unless otherwise indicated, the Kabat numbering scheme is used herein in reference to the sequence positions. The position of an amino acid residue in a particular VH or VL sequence does not refer to the number of amino acids in a particular sequence, but rather refers to the position as designated with reference to a numbering scheme.

The positions of the CDRs and hence the positions of the framework regions of the human heavy chain and light chains are determined using definitions that are standard in the field. For example, the following four definitions are commonly used. The Kabat definition is based on sequence variability and is the most commonly used. The Chothia definition is based on the location of the structural loop regions. The AbM definition is a compromise between the two used by Oxford Molecular's AbM antibody modelling software. The contact definition has been recently introduced and is based on an analysis of the available complex crystal structures. The following are the loop positions, i.e., CDRs, using the four different definitions.

A VH or VL sequence of the invention comprises a heavy or light chain that typically has at least 70% identity, more typically 75%, 80%, 85%, 90%, 95%, 96%, 97%, 98%, or 99% identity to a sequence comprised by SEQ ID NOs:5-22, 29-57, 91-100 or 107-116.

Furthermore, a number of important residues have been identified outside of the CDRs of OS2966 which are preferably utilized in the humanized VH and VL chains. For example, in one embodiment, one or more amino acid residues in the VH chain are identical to that of OS2966 (SEQ ID NO:2), including residues 48, 67, 69, 73, 76, 80, 89, 91 and 93. In one embodiment, one or more amino acid residues in the VL chain are identical to that of OS2966 (SEQ ID NO:4), including residues 36 and 71.

A humanized antibody of the invention binds to the same epitope as the donor antibody, e.g., binds to the same integrin β1 epitope, or competes for binding to the same integrin β1 epitope, that OS2966 binds to, for example. Methods to determine whether the antibody binds to the same epitope are well known in the art, see, e.g., Harlow & Lane, Using Antibodies, A Laboratory Manual, Cold Spring Harbor Laboratory Press, 1999, which discloses techniques to epitope mapping or alternatively, competition experiments, to determine whether an antibody binds to the same epitope as the donor antibody.

A stable humanized antibody of the invention may exhibit altered affinity when compared to the donor antibody. For example, in some embodiments, the affinity of a single chain humanized anti-integrin β1, may, for example, be decreased compared to a single chain antibody comprising the OS2966 VH and VL regions. Such a decrease may be by as much as 10-fold in comparison, but typically a humanized antibody of the invention has an affinity that is at least 25%, more often at least 50% of that of the comparable wildtype antibody. (A "comparable wildtype antibody" refers to an antibody of the same embodiment, e.g., scFv, that comprises the donor antibody VH and VL regions). In some embodiments, the affinity for the epitope is increased, such that a humanized antibody of the invention has an affinity that is 2 times and sometime 5, 10, 50, or 100 times the affinity of the comparable wildtype antibody.

The heavy and light chain regions of the invention are typically obtained using recombinant DNA technology. The recombinant DNA methodologies that are commonly employed to perform this are well known to those of skill in the art. Typically, nucleic acid sequences encoding the frameworks and CDRs of the donor antibodies are generated by PCR, for example by overlap extension. In this technique, the antigen binding sequences of the donor antibody are typically joined to the human framework regions by incorporating the desired sequences into oligonucleotides and creating a series of products using PCR that comprise the desired donor and human sequences. The products may then be joined, typically using additional PCR reactions, in the proper orientation to create the VH and VL chains that comprise human framework regions with donor antibody CDRs. The VL and VH DNA sequences may be ligated together, either directly or through a DNA sequence encoding a peptide linker, using techniques well known to those of skill in the art. These techniques include PCR as well as techniques such as in vitro ligation. The VL and VH sequences may be linked in either orientation.

Examples of techniques sufficient to direct persons of skill through in vitro amplification methods are well known in the art.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., by sequencing.

PCR products are subcloned into suitable cloning vectors that are well known to those of skill in the art and commercially available. The nucleotide sequence of the heavy or light chain coding regions is then determined.

One of skill will appreciate that, utilizing the sequence information provided for the variable regions, nucleic acids encoding these sequences are obtained using any number of additional methods well known to those of skill in the art. Thus, DNA encoding the Fv regions is prepared by any suitable method, including, for example, other amplification techniques such as ligase chain reaction (LCR), transcription amplification, and self-sustained sequence replication, or cloning and restriction of appropriate sequences.

The nucleic acids encoding the antibodies and antibody fragments of the invention can also be generated by direct chemical synthesis using methods such as the phosphotriester method; the phosphodiester method; the diethylphosphoramidite method; and the solid support method of U.S. Pat. No. 4,458,066. If the DNA sequence is synthesized chemically, a single stranded oligonucleotide will result. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are typically later spliced together, for example using overlap extension PCR.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

The VH and VL domains of an antibody of the invention may be directly linked or may be separated by a linker, e.g. to stabilize the variable antibody domains of the light chain and heavy chain, respectively. Suitable linkers are well known to those of skill in the art and include the well known GlyGlyGlyGlySer (SEQ ID NO:122) linker or a variant thereof. For example, a typical linker is (Gly4Ser)$_3$ (SEQ ID NO:123). Other linkers, including hinge regions, that can be used in the invention include those described, for example in Alfthan et al, Protein Eng. 8(7), 725-31; Choi et al, Eur. J. Immunol. 31(1), 94-106; Hu et al, Cancer Res. 56(13), 3055-61; Kipriyanov, et al, Protein Eng. 10(4), 445-53; Pack, et al, Biotechnology (N Y) 11(11), 1271-7; and Roovers, et al, Cancer Immunol. Immunother. 50(1):51-9.

To obtain high level expression of a cloned gene or nucleic acid, such as those cDNAs encoding the humanized antibodies, e.g., a humanized antibody of the invention, or an immunoconjugate or chimeric antibody comprising a humanized antibody of the invention, one typically subclones a nucleic acid encoding the antibody or immunoconjugate into an expression vector that contains an appropriate promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing protein are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Often, in order to express a protein at high levels in a cell, codon preference for the expression system is considered in constructing the nucleic acid sequence to be expressed. Thus, a nucleic acid from one organism, e.g., a human or mouse, may be engineered to accommodate the codon preference of the expression system.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein to be expressed and signals required for efficient polyadenylation of the transcript, ribosome binding sites, and translation termination. The nucleic acid sequence encoding a protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived P.sub.L promoter and N-gene ribosome binding site (Shimatake et al., Nature (1981) 292: 128). The particular promoter system is not critical to the invention, any available promoter that functions in prokaryotes can be used.

Standard bacterial expression vectors include plasmids such as pBR322-based plasmids, e.g., pBLUESCRIPT™, pSKF, pET23D, .lamda.-phage derived vectors, and fusion expression systems such as GST and LacZ. Epitope tags can also be added to recombinant proteins to provide convenient methods of isolation, e.g., c-myc, HA-tag, 6-His tag (SEQ ID NO:124), maltose binding protein, VSV-G tag, anti-DYKDDDDK tag (SEQ ID NO:125), or any such tag, a large number of which are well known to those of skill in the art.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell, supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of the protein, which is recovered from the culture using standard techniques identified below.

One of skill would recognize that modifications can be made to a nucleic acid encoding a polypeptide of the present invention (i.e., an antibody, a label or effector, or an immunoconjugate formed using the antibody) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

Once expressed, the recombinant antibodies, immunoconjugates, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as E. coli have been described and are well-known and are applicable to the antibodies of this invention. See, Buchner, et al., Anal Biochem. 205:263-270 (1992); Pluckthun, Biotechnology 9:545 (1991); Huse, et al., Science 246:1275 (1989) and Ward, et al., Nature 341:544 (1989), all incorporated by reference herein.

Often, functional heterologous proteins from E. coli or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., Biochemistry 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the antibodies and immunoconjugates of the invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

Conservatively modified variants of antibodies of the present invention have at least 80% sequence similarity, often at least 85% sequence similarity, 90% sequence similarity, or at least 95%, 96%, 97%, 98%, or 99% sequence similarity at the amino acid level, with the protein of interest, such as a humanized antibody of the invention.

As noted, the term "conservatively modified variants" can be applied to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

One embodiment of the present invention provides an immunoconjugate comprising a humanized antibody of the invention, linked to an effector molecule or detectable label. Preferably the effector molecule is a therapeutic molecule such as, for example, a toxin, a chemotherapeutic agent, a small molecule, a cytokine or a chemokine, an enzyme, or a radiolabel. Exemplary toxins include, but are not limited to, *Pseudomonas* exotoxin or diphtheria toxin. Suitable toxins are described in e.g., Chaudhary, et al. (1987) Proc Natl Acad Sci USA 84:4538, Chaudhary, et al. (1989) Nature 339:394, Batra, et al. (1991) Mol Cell Biol 11:2200. Brinkmann, et al. (1991) Proc Natl Acad Sci USA 88:8616, Siegall, (1995) Semin Cancer Biol 6:289. Examples of small molecules include, but are not limited to, chemotherapeutic compounds such as taxol, doxorubicin, etoposide, and bleiomycin. Exemplary cytokines include, but are not limited to, IL-1, IL-2, IL-4, IL-5, IL-6, and IL-12. Suitable cytokines and chemokines are described in, e.g., Rosenblum et al. (2000) Int J Cancer 88:267 and Xu et al. (2000) Cancer Res 60:4475 and Biragyn et al. (1999) Nat Biotechnol 17:253. Exemplary enzymes include, but are not limited to, RNAses, DNAses, proteases, kinases, and caspases. Suitable proteases are described in, e.g., Bosslet et al. (1992) Br J Cancer 65:234, Goshom et al. (1993) Cancer Res 53:2123, Rodrigues et al. (1995) Cancer Res 55:63, Michael et al. (1996) Immunotechnology 2:47, Haisma et al. (1998) Blood 92:184. Exemplary radioisotopes include, but are not limited to, $^{32}$P and $^{125}$I. Suitable radionuclides are also described in, e.g., Colcher et al. (1999) Ann N Y Acad Sci 880:263. Additional exemplary effector moieties are, for example, Fc fragments from homologous or heterologous antibodies.

It will be appreciated by those of skill in the art that the sequence of any protein effector molecule may be altered in a manner that does not substantially affect the functional advantages of the effector protein. For example, glycine and alanine are typically considered to be interchangeable as are aspartic acid and glutamic acid and asparagine and glutamine. One of skill in the art will recognize that many different variations of effector sequences will encode effectors with roughly the same activity as the native effector.

The effector molecule and the antibody may be conjugated by chemical or by recombinant means as described above. Chemical modifications include, for example, derivitization for the purpose of linking the effector molecule and the antibody to each other, either directly or through a linking compound, by methods that are well known in the art of protein chemistry. Both covalent and noncovalent attachment means may be used with the humanized antibodies of the present invention.

The procedure for attaching an effector molecule to an antibody will vary according to the chemical structure of the moiety to be attached to the antibody. Polypeptides typically contain a variety of functional groups; e.g., carboxylic acid (COOH), free amine (—NH.sub.2) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In the presently preferred chemical conjugation embodiment, the means of linking the effector molecule and the antibody comprises a heterobifunctional coupling reagent which ultimately contributes to formation of an intermolecular disulfide bond between the effector molecule and the antibody. Other types of coupling reagents that are useful in this capacity for the present invention are described, for example, in U.S. Pat. No. 4,545,985. Alternatively, an intermolecular disulfide may conveniently be formed between cysteines in the effector molecule and the antibody which occur naturally or are inserted by genetic engineering. The means of linking the effector molecule and the antibody may also use thioether linkages between heterobifunctional crosslinking reagents or specific low pH cleavable crosslinkers or specific protease cleavable linkers or other cleavable or noncleavable chemical linkages. The means of linking the effector molecule and the antibody may also comprise a peptidyl bond formed between the effector molecule and the antibody which are separately synthesized by standard peptide synthesis chemistry or recombinant means.

Exemplary chemical modifications of the effector molecule and the antibody of the present invention also include derivitization with polyethylene glycol (PEG) to extend time of residence in the circulatory system and reduce immunogenicity, according to well known methods (See for example, Lisi, et al., Applied Biochem. 4:19 (1982); Beauchamp, et al., Anal Biochem. 131:25 (1982); and Goodson, et al., Bio/Technology 8:343 (1990)).

Antibodies of the present invention may optionally be covalently or non-covalently linked to a detectable label.

Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibody and/or immunoconjugate compositions of this invention are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, leukemia, benign or malignant tumors. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, brain, hepatic carcinoma and various types of head and neck cancer, neurofibromatosis type I or II. Other examples of such cancers include those that are therapy resistant, refractory or metastatic.

Other diseases or disorders which may be treated in include "inflammatory diseases or disorders." "Inflammatory disease or disorder" as used herein include, and are not limited to, pruritis, skin inflammation, psoriasis, multiple sclerosis, rheumatoid arthritis, osteoarthritis, systemic lupus erythematosus, Hashimoto's thyroidis, myasthenia gravis, diabetes type I or II, asthma, inflammatory lung injury, inflammatory liver injury, inflammatory glomerular injury, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, ulcerative colitis, an inflammatory disease of the joints, skin, or muscle, acute or chronic idiopathic inflammatory arthritis, myositis, a demyelinating disease, chronic obstructive pulmonary disease, interstitial lung disease, interstitial nephritis and chronic active hepatitis.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

As used herein, the terms "cell cancer marker(s)", "cancer cell marker(s)", "tumor cell marker(s)", or "solid tumor cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells, such as integrin $\beta 1$. The correlation can relate to either an increased or decreased expression of the gene (e.g. increased or decreased levels of mRNA or the peptide encoded by the gene).

As used herein, the term "detecting a decreased or increased expression relative to non-cancerous control" refers to measuring the level of expression of a gene (e.g., the level of mRNA or protein) relative to the level in a non-cancerous control sample. Gene expression can be measured using any suitable method, including but not limited to, those described herein.

As used herein, the term "detecting a change in gene expression in a cell sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "instructions for using said kit for detecting cancer in said subject" includes instructions for using the reagents contained in the kit for the detection and characterization of cancer in a sample from a subject.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer cells or for determining gene expression profile of that cancerous tissue. In some embodiment, biopsy tissue or fluid is obtained because a subject is suspected of having cancer. The biopsy tissue or fluid is then examined for the presence or absence of cancer, cancer cells, and/or cancer cell gene signature expression.

In certain embodiments of the present invention, cancer cell expression, such as pancreatic, colon, breast, liver, kidney, brain, GBM and the like, comprises elevated levels of integrin β1 compared to non-tumorigenic colon tumor cells. Integrins are heterodimeric extracellular matrix (ECM) cell-surface proteins that consist of both an alpha and a beta chain with chains associating with multiple partners to form different integrins. Integrins function in cellular adhesion and migration to reversibly connect cells to the extracellular matrix or to receptors on other cells and thus can play a critical role in cancer invasion and metastasis. Integrin-mediated adhesion also affects intracellular signaling and can thus regulate cell survival, proliferation, and differentiation.

Integrin beta 1 can form functional receptors with the largest diversity of known alpha integrins, resulting in the ability to interact with a diverse range of ECM environments, and has been implicated in cancer. For example, increased beta 1 integrin signaling is associated with malignant progression of breast cancer both clinically and in breast cancer cell lines.

The integrin β1 has been identified as directly effecting tumor growth. Specifically, treatment of tumor cells with anti-integrin β1 antibodies reduces tumor size and inhibits metastasis.

In some embodiments, the present invention provides methods for detection of expression of integrin β1 as a marker for cancer. In some embodiments, expression is measured directly (e.g., at the protein level), in some embodiments, expression is detected in tissue samples (e.g., biopsy tissue). In other embodiments, expression is detected in bodily fluids (e.g., including but not limited to, plasma, serum, whole blood, mucus, and urine). The present invention further provides kits for the detection of markers, in some embodiments, the presence of a cell cancer marker is used to provide a prognosis to a subject. The information provided is also used to direct the course of treatment. For example, if a subject is found to have a marker indicative of a solid tumor cell, additional therapies (e.g., hormonal or radiation therapies) can be started at an earlier point when they are more likely to be effective (e.g., before metastasis). In addition, if a subject is found to have a tumor that is not responsive to hormonal therapy, the expense and inconvenience of such therapies can be avoided.

In embodiments, gene expression of integrin β1 is detected by measuring the level of the protein. Protein expression can be detected by any suitable method. In some embodiments, proteins are detected by immunohistochemistry utilizing the antibodies described herein.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480, each of which is herein incorporated by reference, can be used.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data, the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research purposes. For example, the data can be used to further optimize the inclusion or elimination of markers as useful indicators of a particular condition or stage of disease.

In yet other embodiments, the present invention provides kits for the detection and characterization of cancer. In some embodiments, the kits contain antibodies specific for a cancer marker, such as the antibodies of the present invention, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of proteins such as integrin β1, e.g. in a tissue sample or in a body fluid. The kit can comprise, for example, an antibody for detection of a polypeptide. In addition, the kit can comprise a reference or control sample; instructions for processing samples, performing the test and interpreting the results; and buffers and other reagents necessary for performing the test.

In some embodiments, in vivo imaging techniques are used to visualize the expression of cancer markers in an animal (e.g., a human or non-human mammal). For example, in some embodiments, integrin β1 is labeled using a labeled antibody of the present invention. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection.

The in vivo imaging methods of the present invention are useful in the diagnosis of cancers that express the solid tumor cell cancer markers of the present invention (e.g., in breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer cells can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art.

In some embodiments, the present invention provides therapies for diseases and disorders including immunological/inflammatory diseases and disorders given the role of integrin β1 in broader functional activities as discussed above. Further, diseases and disorders which may be targeted by the compositions of the present invention include multiple sclerosis, Crohn's disease, rheumatoid arthritis, inflammatory bowel disease and the like. Similarly, it is to be expected that certain eye related diseases may be targeted including wet age-related macular degeneration (AMD).

In some embodiments, the present invention provides therapies for diseases such as cancer, e.g., breast, brain, prostate and colon cancer. In some embodiments, therapies target cancer markers, such as integrin β1.

In some embodiments, the present invention provides antibodies that target tumors that express a cell cancer marker, e.g., integrin β1.

In some embodiments, the therapeutic antibodies comprise an antibody of the present invention conjugated to a cytotoxic agent as discussed above.

The following example is provided to further illustrate the advantages and features of the present invention, but are not intended to limit the scope of the invention. While they are typical of those that might be used, other procedures, methodologies, or techniques known to those skilled in the art may alternatively be used.

Example 1

Variable Region Gene Sequencing

Genes encoding the OS2966 anti-human integrin β1 monoclonal antibody were subjected to variable (V)-region sequence analysis. Total RNA was extracted from 3 to $10 \times 10^6$ hybridoma cells using the RNAqueous-4PCR Kit™ (Ambion, Warrington, UK) and used to synthesize cDNA. Murine immunoglobulin heavy and kappa light chain V-region fragments were amplified by PCR using degenerate mouse leader sequence primers (Sigma) and unique constant domain primers (Sigma) as shown in Table 1. The resulting PCR fragments were subcloned into the pGEM-T Easy I™ vector system (Promega, Southampton, UK) and inserts were sequenced using the vector-specific primer, M13Forward (Sigma) All DNA sequencing was performed by Geneservice Ltd, Cambridge, UK). Unique V-region nucleotide sequences were obtained for OS2966 (SEQ ID NOs: 1 (VH) and 3 (VL)).

TABLE 1

| Sequence | Name-Pool | SEQ ID NO |
|---|---|---|
| ATGRASTTSKGGYTMARCTKGRTTT | MuIgV$_H$5'-A | 58 |
| ATGRAATGSASCTGGGTYWTYCTCTT | MuIgV$_H$5'-B | 59 |
| ATGGACTCCAGGCTCAATTTAGTTTTCCT | MuIgV$_H$5'-C | 60 |
| ATGGCTGTCYTRGBGCTGYTCYTCTG | MuIgV$_H$5'-C | 61 |
| ATGGVTTGGSTGTGGAMCTTGCYATTCCT | MuIgV$_H$5'-C | 62 |
| ATGAAATGCAGCTGGRTYATSTTCTT | MuIgV$_H$5'-D | 63 |

TABLE 1-continued

| Sequence | Name-Pool | SEQ ID NO |
|---|---|---|
| ATGGRCAGRCTTACWTYYTCATTCCT | MuIgV$_H$5'-D | 64 |
| ATGATGGTGTTAAGTCTTCTGTACCT | MuIgV$_H$5'-D | 65 |
| ATGGGATGGAGCTRTATCATSYTCTT | MuIgV$_H$5'-E | 66 |
| ATGAAGWTGTGGBTRAACTGGRT | MuIgV$_H$5'-E | 67 |
| ATGGRATGGASCKKIRTCTTTMTCT | MuIgV$_H$5'-E | 68 |
| ATGAACTTYGGGYTSAGMTTGRTTT | MuIgV$_H$5'-F | 69 |
| ATGTACTTGGGACTGAGCTGTGTAT | MuIgV$_H$5'-F | 70 |
| ATGAGAGTGCTGATTCTTTTGTG | MuIgV$_H$5'-F | 71 |
| ATGGATTTTGGGCTGATTTTTTTATTG | MuIgV$_H$5'-F | 72 |
| CCAGGGRCCARKGGATARACIGRTGG | MuIgGV$_H$3'-2 | 73 |
| ATGRAGWCACAKWCYCAGGTCTTT | MuIgkV$_L$5'-A | 74 |
| ATGGAGACAGACACACTCCTGCTAT | MuIgkV$_L$5'-B | 75 |
| ATGGAGWCAGACACACTSCTGYTATGGGT | MuIgkV$_L$5'-C | 76 |
| ATGAGGRCCCCTGCTCAGWTTYTTGGIWTCTT | MuIgkV$_L$5'-D | 77 |
| TGGGCWTCAAGATGRAGTCACAKWYYCWGG | MuIgkV$_L$5'-D | 78 |
| ATGAGTGTGCYCACTCAGGTCCTGGSGTT | MuIgkV$_L$5'-E | 79 |
| ATGTGGGGAYCGKTTTYAMMCTTTTCAATTG | MuIgkV$_L$5'-E | 80 |
| ATGGAAGCCCCAGCTCAGCTTCTCTTCC | MuIgkV$_L$5'-E | 81 |
| ATGAGIMMKTCIMTTCAITTCYTGGG | MuIgkV$_L$5'-F | 82 |
| ATGAKGTHCYCIGCTCAGYTYCTIRG | MuIgkV$_L$5'-F | 83 |
| ATGGTRTCCWCASCTCAGTTCCTTG | MuIgkV$_L$5'-F | 84 |
| ATGTATATATGTTTGTTGTCTATTTCT | MuIgkV$_L$5'-F | 85 |
| ATGAAGTTGCCTGTTAGGCTGTTGGTGCT | MuIgkV$_L$5'-G | 86 |
| ATGGATTTWCARGTGCAGATTWTCAGCTT | MuIgkV$_L$5'-G | 87 |
| ATGGTYCTYATVTCCTTGCTGTTCTGG | MuIgkV$_L$5'-G | 88 |
| ATGGTYCTYATVTTRCTGCTGCTATGG | MuIgkV$_L$5'-G | 89 |
| ACTGGATGGTGGGAAGATGGA | MuIgkV$_L$3'-1 | 90 |

Example 2

Generation of Chimeric Antibodies

The heavy and light chain variable domain sequences of the OS2966 monoclonal antibody were PCR amplified and subcloned into pANT antibody expression vectors (FIG. 14) with heavy and light chain V-regions cloned into pANT17 and pANT13 respectively. Heavy chain V-region genes were cloned into pANT17 via MluI and HindIII sites in frame with either the human χ1 heavy chain gene (G1m3 (G1m(f)) allotype) or the human χ4 heavy chain gene, and light chain V-region genes were cloned into pANT13 via BssHII and BamHI sites in frame with the human kappa light chain constant region gene (Km3 allotype). Transcription of both heavy and light chain genes was under the control of the CMV I/E promoter (U.S. Pat. No. 5,168,062 and U.S. Pat. No. 5,385,839, University of Iowa) and the pANT17 plasmid contained a mutant dhfr minigene (Simonsen & Levinson 1983, PNAS 80:2495-2499) under the control of a SV40 promoter and polyA sequence for selection in eukaryotic cells. Both pANT17 and pANT13 contained a β-lactamase (Ap$^R$) gene for prokaryotic selection and a pMB1 origin of replication for propagation in prokaryotic cells. All plasmids were propagated in E. coli XL1-blue (Stratagene Cat. No. 200130).

The heavy and light chain expression constructs were then co-transfected either transiently into HEK293 cells by calcium phosphate-based transfection or stably transfected into NS0 cells by electroporation. Secreted antibody was purified from the cell culture supernatants by Protein A chromatography.

Example 3

Generation of Humanized Antibodies

Humanized antibodies were generated using methods described in EP1844074 (Antitope Ltd). Structural models of the mouse V-regions were produced using Swiss PDB and analyzed in order to identify important amino acids from the OS2966 V-regions that were likely to be important for the integrin β1 binding properties of the antibody (constraining residues'). A database of human V-region sequences was used to identify segments of human V-region sequences containing each of the constraining residues to be used in design of the humanized antibodies. Typically two or more alternative V-region sequence segments were used to provide each constraining residue resulting in a large range of possible sequences of humanized anti-integrin B1 V-region sequences. These sequences were then analysed for the prediction of non-germline MHC class II peptide binding by in silico analysis as described in Fothergill et al. (WO9859244, assignee Eclagen Ltd) and also for known CD4+ T-cell epitopes using databases including "The Immune Epitope Database and Analysis Resource", available on the world wide web at URL: immuneepitope.org/. V-region sequences with predicted non-germline MHC class II binding peptides, or with significant hits against T cell epitope databases were discarded. This resulted in a reduced set of V-region sequences. Selected combinations of V-region sequence segments were then combined to produce humanized heavy and light chain variable region amino acid sequences. Five heavy chains and four light chain sequences (designated VH1 to VH5, and Vκ1 to Vκ4 respectively) were selected (SEQ ID NOs: 6, 8, 10, 12, 14, 16, 18, 20, 22) for gene synthesis. In addition, a further set of heavy and light chain V-region sequences (designated VH6 to VH15, and Vκ5 to Vκ13 respectively) were designed (SEQ ID NOs: 29 to 38 and 44 to 52 respectively).

In addition to the above, humanized antibodies were designed using the general methods of Winter (U.S. Pat. No. 6,548,640B2) as modified in Winter, Carr, Harris (EP0629240B1) whereby sequences were designed using the CDR sequences of OS2966 (SEQ ID NOs: 23 to 28) to replace CDRs in a set of human germline V-region sequences with addition of human J region sequences. In addition, constraining residues as used in the humanized antibodies of the above paragraph were introduced into the germline V-region framework sequences. The resultant sequences for the heavy and light chain V-regions were designated VH16 to VH20, and Vκ14 to Vκ18 respectively, and are listed as SEQ ID NOs: 39-43 and 53-57.

In addition to the above, deimmunised antibodies were designed using the general methods of Carr et al. (U57465572 B2) whereby CD4+ T cell epitopes within the V-region sequences of OS2966 (SEQ ID NOs: 2 and 4) were identified and mutations introduced in order to potentially remove one or more of these epitopes.

DNA encoding humanized OS2966 variant V-regions were synthesized and subcloned into the expression vectors pANT17 and pANT13 as described in Example 2. All combinations of humanized VH and Vκ chains (i.e. combinations of VH1 to VH5, and Vκ1 to Vκ4, (i.e. a total of 20 pairings) were transiently transfected into HEK293 and also transfected into NS0 cells, and antibody was purified by protein A chromatography from the culture supernatants as described in Example 2.

Example 4

Analysis of Humanized Antibodies

The binding of HEK-derived and NS0-derived OS2966 humanized variants to human integrin β1 was assessed in a competition ELISA against the chimeric antibody from Example 2. The OS2966 chimeric antibody was biotinylated using Biotin Tag™ Micro Biotinylation kit (Sigma-Aldrich). 96 well MaxiSorp plates (Nunc) were coated with 0.5 µg/ml human integrin β1 (100 µl final volume) at 4° C. overnight. The plates were washed with wash buffer (0.05% Tween20 in Dulbecco's-PBS) and blocked with Dulbecco's PBS-2% BSA for 1 hour at room temperature. Plates were then washed 3 times with wash buffer. Test humanized antibodies at various concentrations were premixed with biotinylated chimeric antibody (0.02 µg/ml final concentration) and then added to the human integrin (31-coated plate (100 µl final volume). Plates were incubated for 1 h at room temperature and washed 3 times with wash buffer. 100 µl of a 1 in 500 dilution of Streptavidin HRP (Sigma-Aldrich) was added and incubated for 1 hour at room temperature. Plates were washed 3 times with wash buffer and 100 µl of SigmaFast OPD substrate (Sigma-Aldrich, Cat# P9187) was added and incubated at room temperature in the dark for 4 minutes. The reaction was stopped by adding 50 µl of 3M HCl. Plates were read at 490 nm using Dynex plate reader.

Example 5

Generation of scFv's and Fab's

Humanized OS2966 anti-human integrin variants from Example 3 were converted into scFv's and cloned into M13 phage display vectors as described in Benhar I. and Reiter Y., Current Protocols in Immunology, Unit 10.19B, Wiley Online Library, May 2002 (available on the world wide web at URL: currentprotocols.com/protocol/im1019b) using the pCANTAB5E vector RPAS Expression Module (Amersham Pharmacia Biotech, Little Chalfont, UK). Humanized VH and VK genes were amplified using primers which provided terminal SfiI and NotI restriction sites, an internal Gly4Ser linker and a C terminal his6 tag. The scFv constructs were inserted into the pCANTAB5E vector as SfiI-NotI fragments and transformed into *E. coli* HB2151 resulting in scFv exported to the periplasm and partially to the growth medium. scFv's were purified from growth medium by nickel-chelate affinity chromatography using HIS-Select HF Cartridges (Sigma-Aldrich). Purified scFv's were tested in the competition assay as detailed in Example 4. Humanized OS2966 variants from Example 3 were also converted into Fab's using the method used for scFv's except that amplified humanized VH and VK genes were further amplified with CH1 and Cκ constant region genes to form VH-CH1 and VK-Cκ fragments which were further amplified with primers to join these fragments with a 22 amino acid pelB leader sequence (Lei S. P., Lin H. C., Wang S. S., Callaway J., and Wilcox G., J. Bacteriol. 169 (1987) p 4379-4383) between the upstream VH-CH1 and downstream VK-Cκ gene fragments resulting in a dicistronic Fab gene. Fab's from humanized antibody variants were generated and purified as above for scFv's and tested in the human integrin β1 competition assay as detailed in Example 4.

Example 6

Analysis of CD4+ T Cell Responses

The immunogenicity potential of the humanized antibodies from Examples 3 and 5 was performed in comparison to the humanized anti-human integrin β1 K20 (Poul et al., Molecular Immunology 32 (1995) p 102-116). PBMCs (peripheral blood mononuclear cells) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMCs were isolated from buffy coats by Lymphoprep (Axis-shield, Dundee, UK) density centrifugation and CD8+ T cells were depleted using CD8+ RosetteSep™ (StemCell Technologies Inc, London, UK). Donors were characterized by identifying HLA-DR haplotypes using an HLA SSP-PCR based tissue-typing kit (Biotest, Solihull, UK). T cell responses to control antigens including the recall antigen tetanus toxin were also determined (KLH Pierce, Cramlingtom, UK and peptides derived from Influenza A and Epstein Barr viruses). PBMC were then frozen and stored in liquid nitrogen until required.

To prepare monocyte derived dendritic cells (DC), 50 different donor PBMCs were selected to provide a distribution with frequencies of HLA-DR and HLA-DQ allotypes similar to the frequencies in the overall world population. PBMCs were revived in AIM-V® culture medium and CD14+ cells isolated using Miltenyi CD14 Microbeads and LS columns (Miltenyi Biotech, Oxford, UK). Monocytes were resuspended in AIM-V® supplemented with 1000 U/ml IL-4 and 1000 U/ml GM-CSF ("DC culture media") to 4-6×10$^6$ PBMC/ml and then distributed in 24 well plates (2 ml final culture volume). Cells were fed on day 2 by half volume DC culture media change. By day 3, monocytes had differentiated to semi-mature DC which were pre-incubated with either 40 ug/ml of test humanized or chimeric antibody, 100 µg/ml KLH or media only. Semi-mature DC were incubated with antigen for 24 hours after which excess test antibody was removed by washing the cells twice and resuspending in DC culture media supplemented with 50 ng/ml TNF-α (Peprotech, London, UK). DCs were fed on day 7 by a half volume DC culture media (supplemented with 50 ng/ml TNFα) change before harvesting mature DC on day 8. The harvested mature DC were counted and viability assessed using trypan blue dye exclusion. The DC were then γ-irradiated (4000 rads) and resuspended at 2×10$^5$ cells per ml in AIM-V media before use in the ELISpot and proliferation assays. Additionally, on day 8, fresh CD4+ T cells were also prepared. To purify CD4+ T cells, PBMCs were revived in AIM-V® culture medium and CD4+ cells isolated using Miltenyi CD4 Microbeads and LS columns (Miltenyi Biotech, Oxford, UK) and resuspended in AIM-V® media at $2 \times 10^6$ cells/ml.

On day 8, T cell proliferation assays were established whereby $1 \times 10^5$ autologous CD4+ T cells were added to $1 \times 10^4$ humanized or chimeric antibody loaded DC (ratio of 10:1) in 96 well U-bottomed plates, with AIM-V® media added to a final volume 200 ul/well). On day 14, assay plates were pulsed with 1 uCi [3H] (Perkin Elmer, Beaconsfield, UK) per well in 25 ul AIMV for 6 hours before harvesting onto filter mats (Perkin Elmer) using a TomTec Mach III (Hamden Conn., USA) cell harvester. All antibody preparations were tested in sextuplet cultures. Counts per minute (cpm) for each well were determined by Meltilex™ (Perkin Elmer) scintillation counting on a 1450 Microbeta Wallac Trilux Liquid Scintillation Counter (Perkin Elmer) in paralux, low background counting. Counts per minute for each antibody sample were normalized to the media only control.

For ELISpot assays, ELISpot plates (Millipore, Watford, UK) were coated with 100 ul/well IL-2 capture antibody (R&D Systems, Abingdon, UK) in PBS. Plates were then washed twice in PBS, incubated overnight in block buffer (1% BSA (Sigma) in PBS) and washed in AIM V® medium. On day 8, $1 \times 10^5$ autologous CD4+ T cells were added to $1 \times 10^4$ antigen loaded DC (ratio of 10:1) in 96 well ELISpot plates. All antibody preparations were tested in sextuplet cultures. For each donor PBMC, a negative control (AIM V® medium alone), no cells control and a PHA (10 ug/ml) positive control were also included.

After a further 7 day incubation period, ELISpot plates were developed by three sequential washes in dH$_2$O and PBS prior to the addition of 100 ulfiltered biotinylated detection antibody (R&D Systems, Abingdon, UK) in PBS/1% BSA. Following incubation at 37° C. for 1.5 hour, plates were further washed three times in PBS and 100 ul filtered streptavidin-AP (R&D Systems) in PBS/1% BSA was added for 1 hour (incubation at room temperature). Streptavidin-AP was discarded and plates were washed four times in PBS. BCIP/NBT (R&D Systems) was added to each well and incubated for 30 minutes at room temperature. Spot development was stopped by washing the wells and the backs of the wells three times with dH$_2$O. Dried plates were scanned on an Immunoscan™ Analyser and spots per well (spw) were determined using Immunoscan™ Version 4 software.

For both proliferation and IL-2 ELISpot assays, results were expressed as a Stimulation Index (SI) defined as the ratio of cpm (proliferation assay) or spots (ELISpot assay) for the test antibody against a medium-only control using a threshold of SI equal to or greater than 2 (SI≥2.0) for positive T cell responses.

Example 7

Tumor Animal Model

A tumor animal model can be used for the in vivo analysis of humanized anti-integrin 131 antibodies in inhibiting tumor growth. For example, an orthotic breast cancer model using MDA-MB-231 cells may be used as a model of primary tumor growth and spontaneous metastasis in human integrin β1 knock-in mice or immune deficient mice (e.g., nu/nu, severe combined immune deficiency [SCID]).

Integrin β1 knock-in mice (7-10 weeks old, males and females distributed equally across groups) may be injected subcutaneously into the mammary fat pad with MDA-MB-231 cells in 0.1 ml volume. Anti-integrin β1 antibody of the present invention, OS2966 or an isotype matched control antibody may be injected at 1 mg/kg-20 mg/kg, such as 5 mg/kg or 10 mg/kg doses (dosing volume 10 ml/kg) weekly starting the day following tumor cell administration ("Day 2") or when the tumor is palpable and mean tumor volume is approximately 100 mm$^3$. Tumor measurements may be taken biweekly during the course of the experiment by caliper measurement. Animals may be followed to determine results.

Example 8

Sequence Analysis

Figures 2, 15:
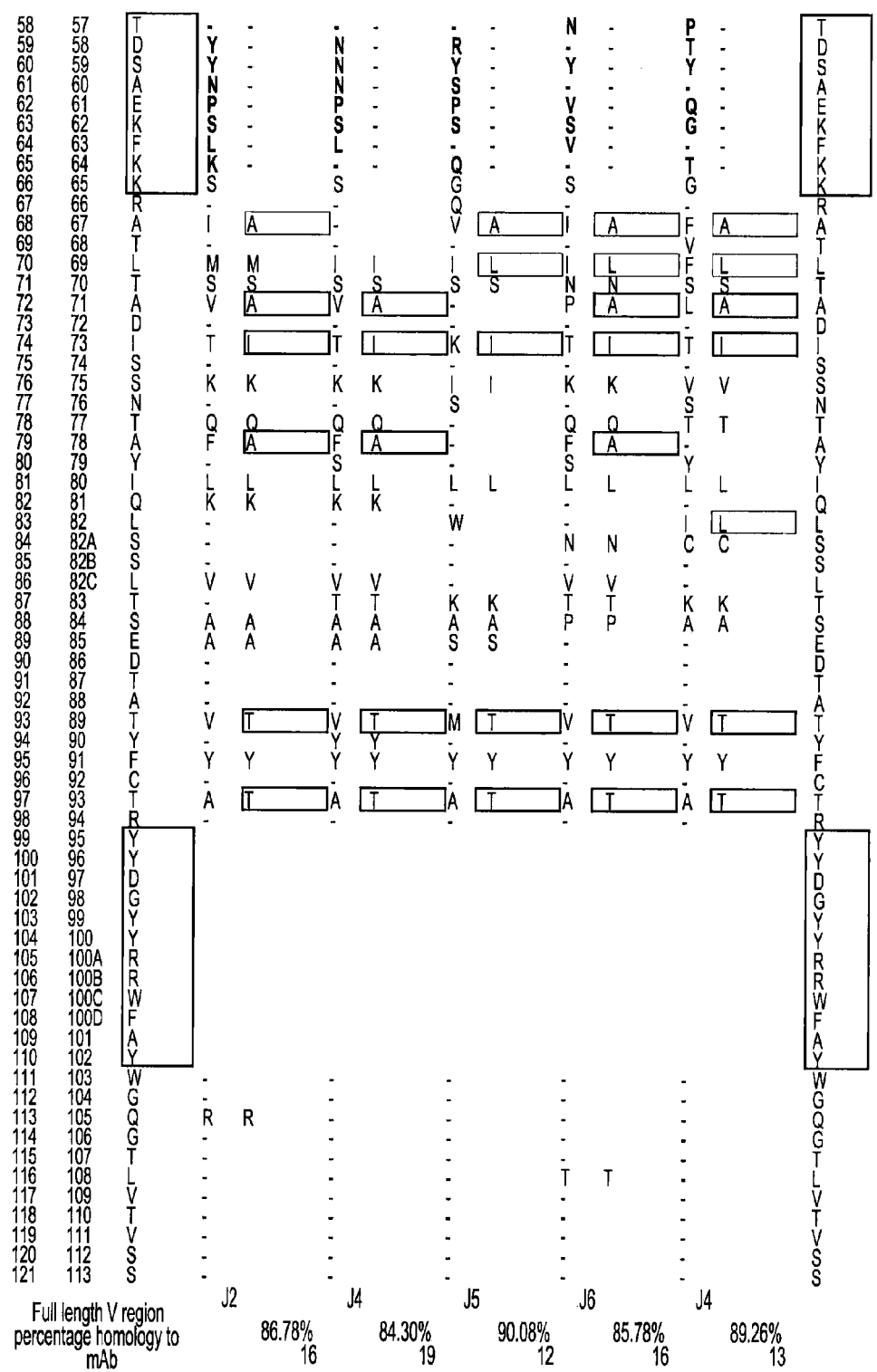
FIG. 2 is a pictorial representation depicting nucleic acid and amino acid sequences of the VL region of antibody OS2966 produced by hybridoma OS2966.
FIG. 15 is a pictorial representation depicting sequence analysis and alignment of humanized VH chains of the invention with comparison to VH of antibody OS2966 (SEQ ID NO:2). Sequences of FIG. 15 are as follows: OS2966 is SEQ ID NO:2; Variant 1 is SEQ ID NO:6; Variant 2 is SEQ ID NO:8; Variant 3 is SEQ ID NO:10; Variant 4 is SEQ ID NO:12; Variant 5 is SEQ ID NO:14; Variant 6 is SEQ ID NO:29; Variant 7 is SEQ ID NO:30; Variant 8 is SEQ ID NO:31; Variant 9 is SEQ ID NO:32; Variant 10 is SEQ ID NO:33; Variant 11 is SEQ ID NO:34; Variant 12 is SEQ ID NO:35; Variant 13 is SEQ ID NO:36; Variant 14 is SEQ ID NO:37; Variant 15 is SEQ ID NO:38; VH2 is SEQ ID NO:91; Variant 16 is SEQ ID NO:92; VH4 is SEQ ID NO:93; Variant 17 is SEQ ID NO:94; VH5 is SEQ ID NO:95; Variant 18 is SEQ ID NO:96; VH6 is SEQ ID NO:97; Variant 19 is SEQ ID NO:98; VH7 is SEQ ID NO:99; and Variant 20 is SEQ ID NO:100.
Figure 20:
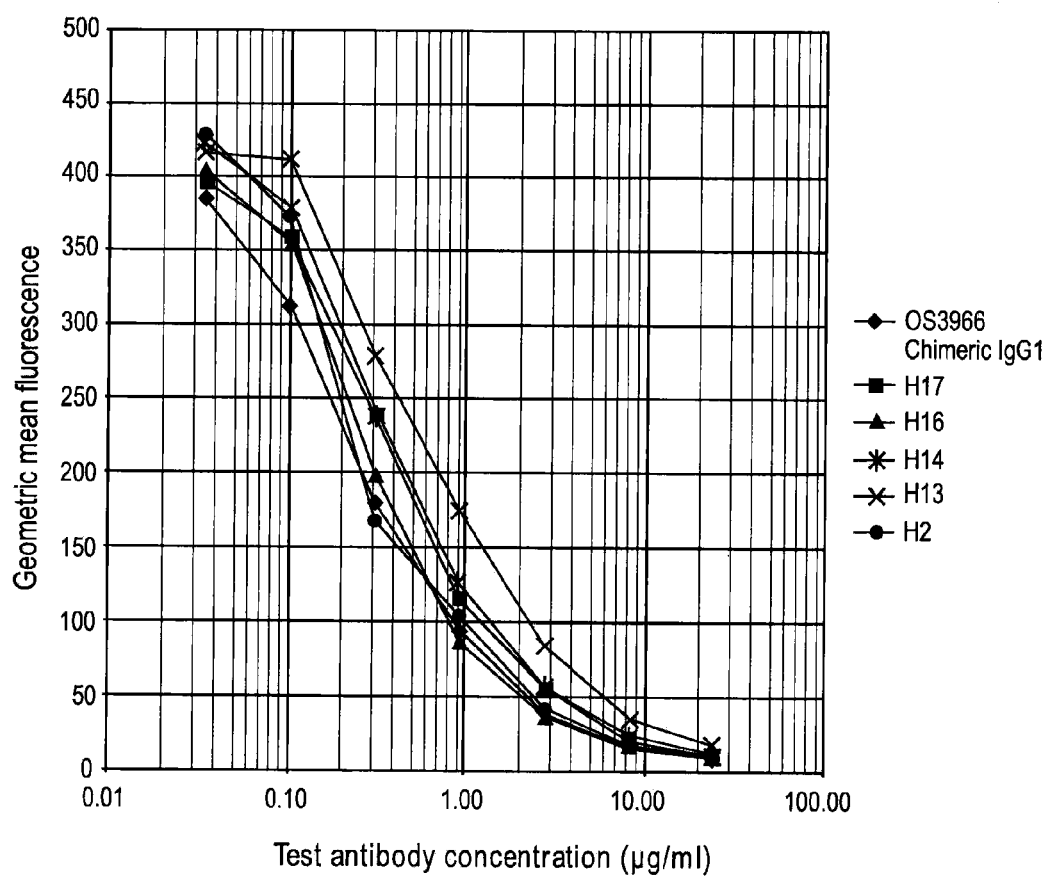
FIG. 20 is a graphical representation depicting relative affinity of composite human antibody variants of the present invention (those shown in Table 2).
Figure 21:
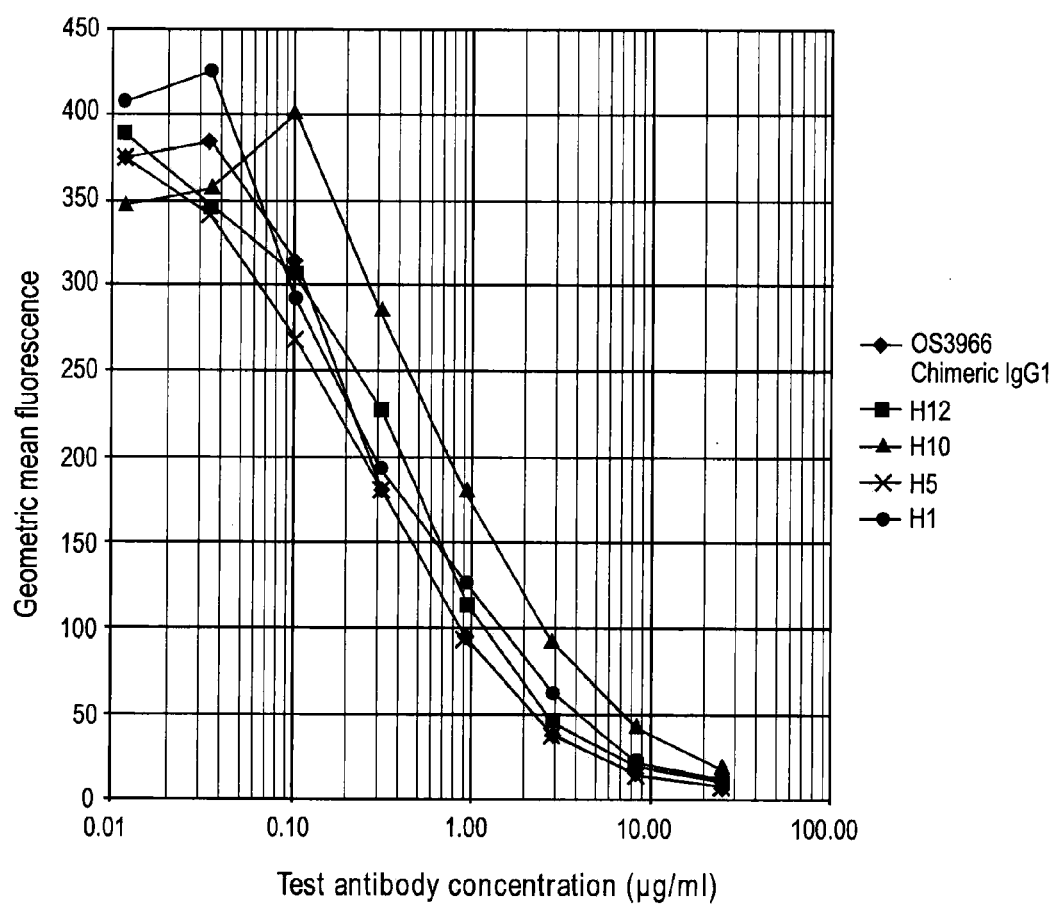
FIG. 21 is a graphical representation depicting relative affinity of composite human antibody variants of the present invention (those shown in Table 2).
Figure 22:
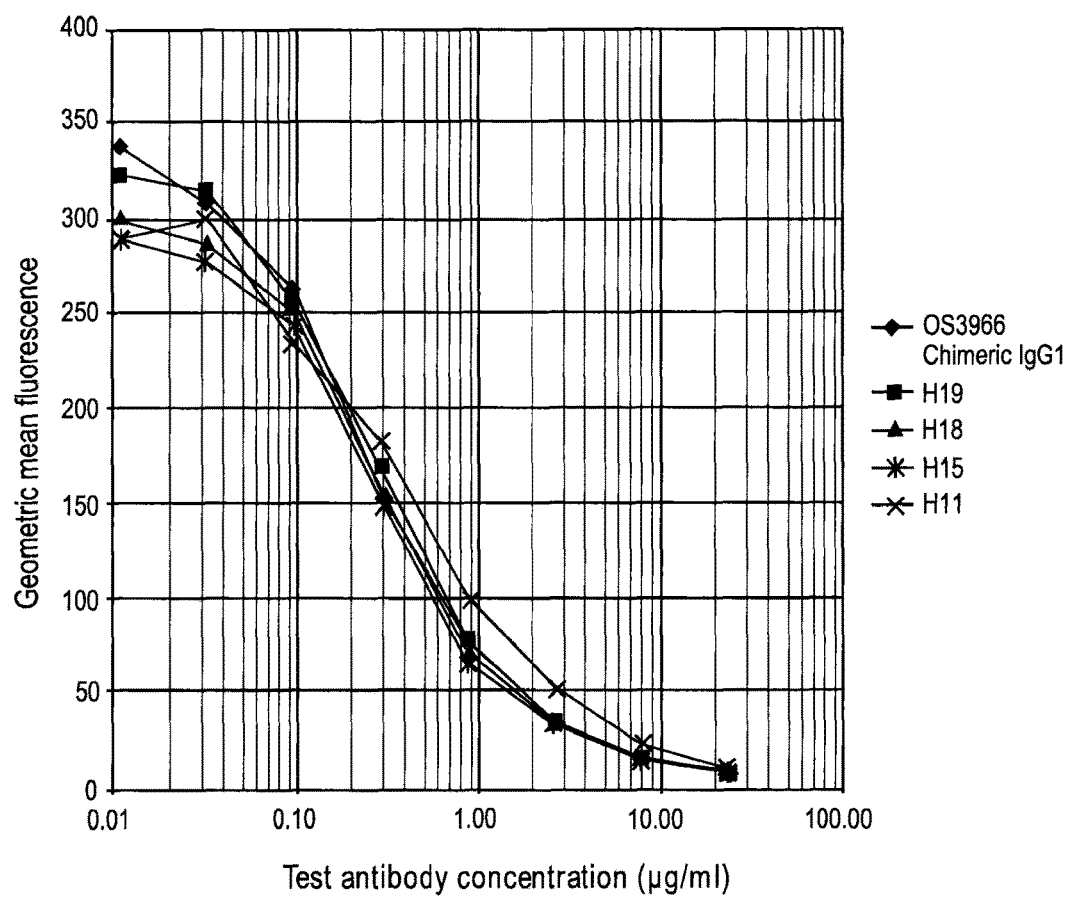
FIG. 22 is a graphical representation depicting relative affinity of composite human antibody variants of the present invention (those shown in Table 2).
Figure 23:
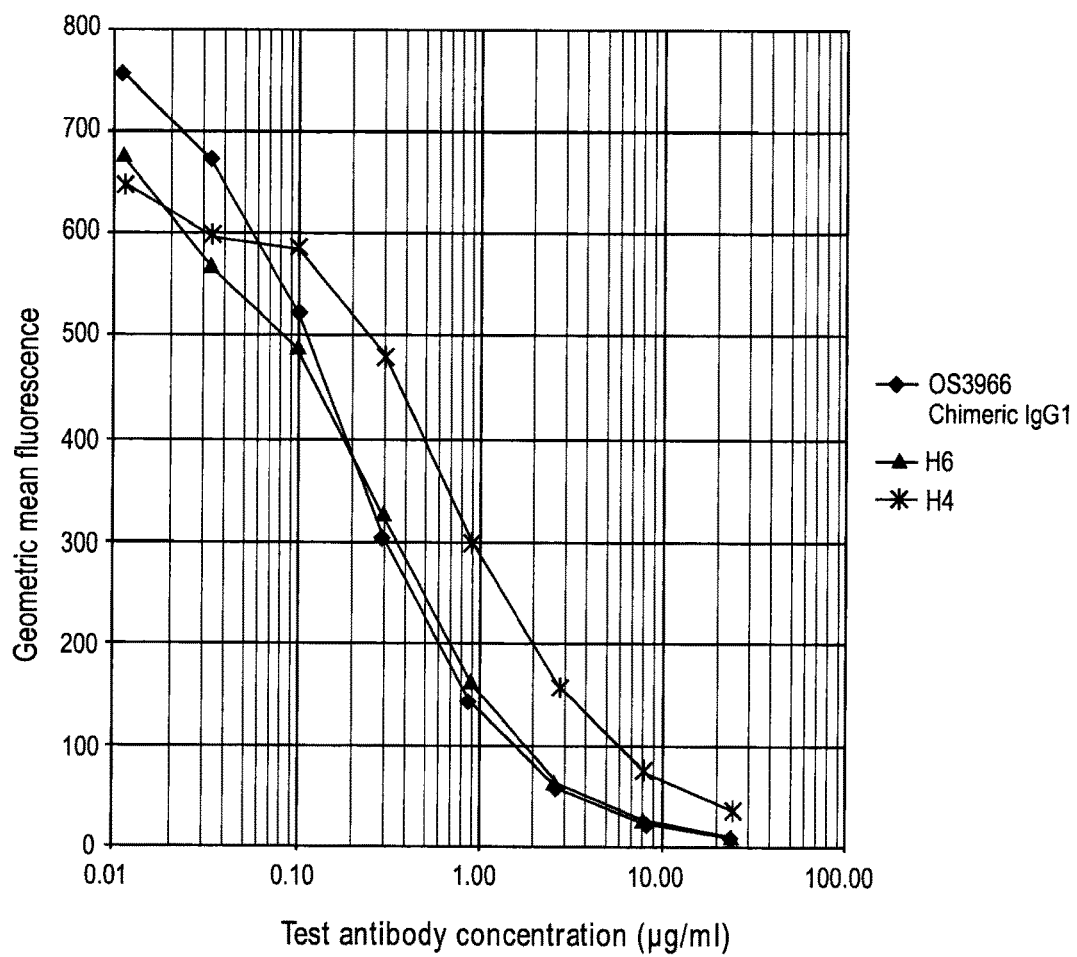
FIG. 23 is a graphical representation depicting relative affinity of composite human antibody variants of the present invention (those shown in Table 2).
Figure 24:
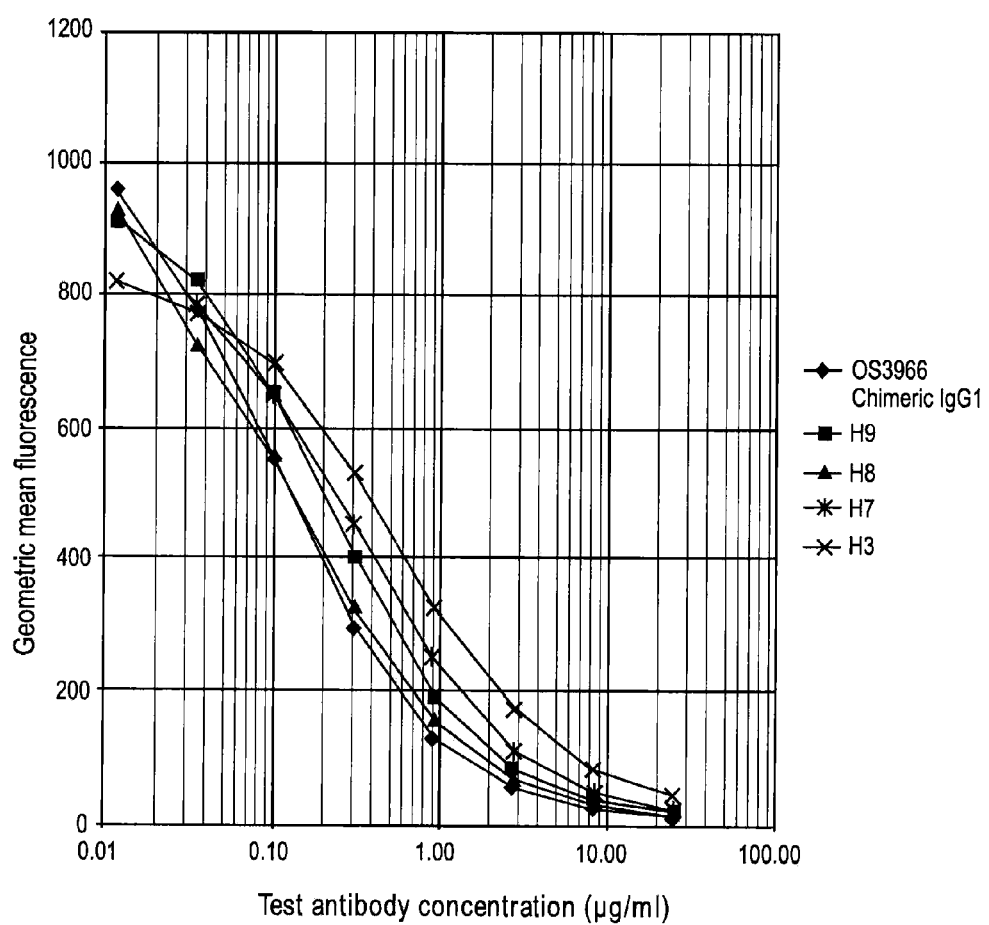
FIG. 24 is a graphical representation depicting relative affinity of composite human antibody variants of the present invention (those shown in Table 2).

Sequence analysis was performed on the heavy and light chains generated in the Examples to determine important VH and VL amino acid residues outside of CDRs from the OS2966 sequence which are preferably included in the humanized sequences. Such residues are identical to those of OS2966 in addition to those of CDRs. Such residues are identified as "c" residues in FIGS. 15 and 16. As shown, for the VH chain residues 48, 67, 69, 73, 76, 80, 89, 91 and 93 are preferably identical to corresponding residues of OS2966 (SEQ ID NO:2). Also, for the VL chain, residues 36 and 71 are preferably identical to corresponding residues of OS2966 (SEQ ID NO:4).

Codon usage corresponding to the VH and VL sequences is provided in FIG. 17 while FIG. 18 provides a summary of the amino acid sequences of the VH and VL chains.

Example 9

Method of Increasing Radiation Sensitivity by Inhibition of Integrin β1

Humanized antibodies of the present invention may be utilized to increase radiation sensitivity by inhibition of integrin β1 as disclosed in U.S. Patent Appl. Pub. No. 20070237711, Park et al., Cancer Res 2008; 68:(11)4398, and Yao et al., Cancer Res 2007; 67:(2)659, all of which are incorporated herein in their entireties. The antibodies of the present invention may be utilized in a method of co-administration of the antibody or antibody containing compositions described herein, in combination with ionizing radiation that causes increased apoptosis in tumor cells, notably in breast cancer tumor cells.

Example 10

Validation and Analysis of Composite Human Antibody Variants

Composite humanized antibodies were generated as discussed in Example 3. Table 2 provides a list of the various antibodies generated showing which VH and Vk sequences were utilized.

TABLE 2

Variant designations according to V region ID.

| HUMANIZED VARIANT REF. NO. | V REGION ID | CORRESPONDING VH AND VK SEQ ID NOS. |
|---|---|---|
| H1 | VH5VK3 | 14, 20 |
| H2 | VH3VK1 | 10, 16 |
| H3 | VH4VK4 | 12, 22 |
| H4 | VH5VK4 | 14, 22 |

TABLE 2-continued

Variant designations according to V region ID.

| HUMANIZED VARIANT REF. NO. | V REGION ID | CORRESPONDING VH AND VK SEQ ID NOS. |
|---|---|---|
| H5 | VH5VK2 | 14, 18 |
| H6 | VH5VK1 | 14, 16 |
| H7 | VH4VK3 | 12, 20 |
| H8 | VH4VK2 | 12, 18 |
| H9 | VH4VK1 | 12, 16 |
| H10 | VH3VK4 | 10, 22 |
| H11 | VH3VK3 | 10, 20 |
| H12 | VH3VK2 | 10, 18 |
| H13 | VH2VK4 | 8, 22 |
| H14 | VH2VK3 | 8, 20 |
| H15 | VH2VK2 | 8, 18 |
| H16 | VH2VK1 | 8, 16 |
| H17 | VH1VK3 | 6, 20 |
| H18 | VH1VK2 | 6, 18 |
| H19 | VH1VK1 | 6, 16 |

Binding of composite human antibody variants (from Table 2) was assessed in a competition FACS assay with the OS2966 murine chimeric antibody (murine OS2966 Fab sliced to human Fc). In brief, a dilution series (three-fold) of chimeric or humanized antibodies starting from 25.0 µg/ml was premixed with a constant concentration of murine OS2966 (0.1875 µg/ml) in FACS buffer (1% BSA in 1×PBS pH 7.4) before mixing with $3 \times 10^5$ Jurkat cells. After incubating on ice for 1 hour, cells were washed and the binding of murine OS2966 was detected with PE labelled goat anti-murine Fc (Jackson ImmunoResearch, Cat. No. 115-116-071). After incubating on ice for 45 min, cells were washed, resuspended in 300 µl FACS buffer and analyzed on a Beckton Dickinson FACScalibur™. The geometric mean fluorescence intensity was plotted against antibody concentration (FIGS. 20-24). These data were used to calculate IC50 values for each antibody and these values were normalized to the IC50 of chimeric antibody that was included in each FACS assay (Table 3).

TABLE 3

Human variant relative affinity. The relative IC50 was calculated by dividing the IC50 of the test antibody by that of the chimeric antibody assayed in the same assay.

| VARIANT | RELATIVE AFFINITY (IC50) |
|---|---|
| H1 | 0.88 |
| H2 | 0.97 |
| H3 | 2.70 |
| H4 | 3.26 |
| H5 | 0.85 |
| H6 | 1.24 |
| H7 | 1.76 |
| H8 | 1.18 |
| H9 | 1.34 |
| H10 | 2.76 |
| H11 | 1.58 |
| H12 | 1.15 |
| H13 | 2.00 |
| H14 | 1.17 |
| H15 | 1.32 |
| H16 | 1.08 |
| H17 | 1.35 |
| H18 | 1.20 |
| H19 | 1.13 |

Three variants (H1, H2, H5) demonstrated slightly greater relative affinities and four variants (H3, H4, H10, H13) had significantly lower relative affinities than murine OS2966 antibody.

Figure 25A:
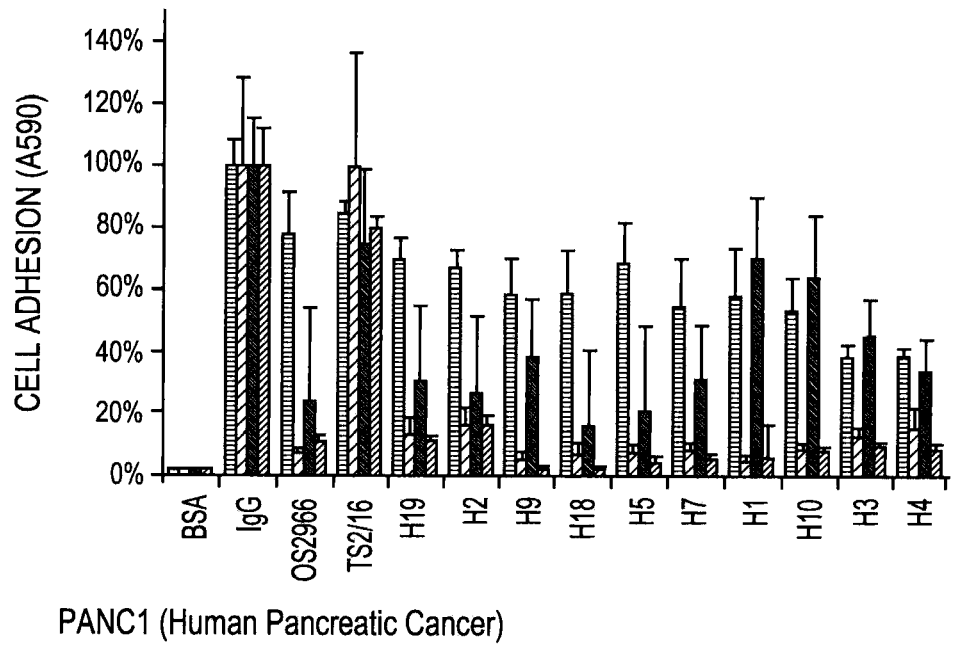
FIGS. 25A-D is a series of graphical representations illustrating functional validation in extracellular matrix (ECM) adhesion assays of composite human antibody variants of the present invention. Functional inhibition of the integrin β1 subunit with composite human antibody variants of the present invention (from Table 2) was assessed in an adhesion microplate assay on multiple ECM and in multiple cancer cell lines.
Figure 25B:
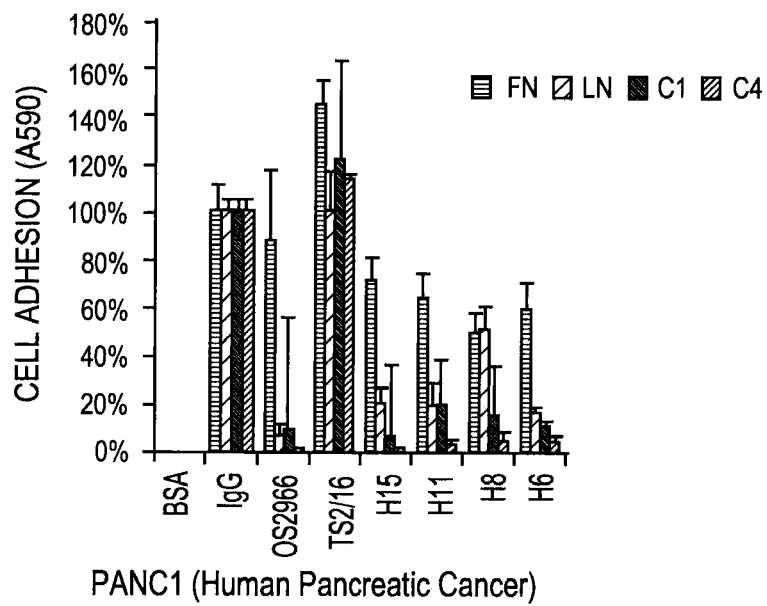
Figure 25C:
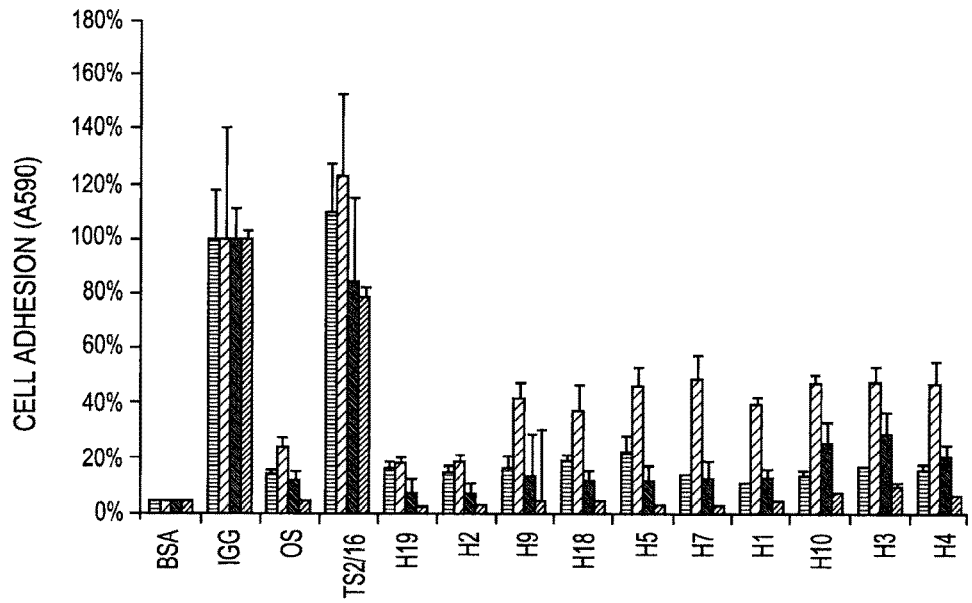
Figure 25D:
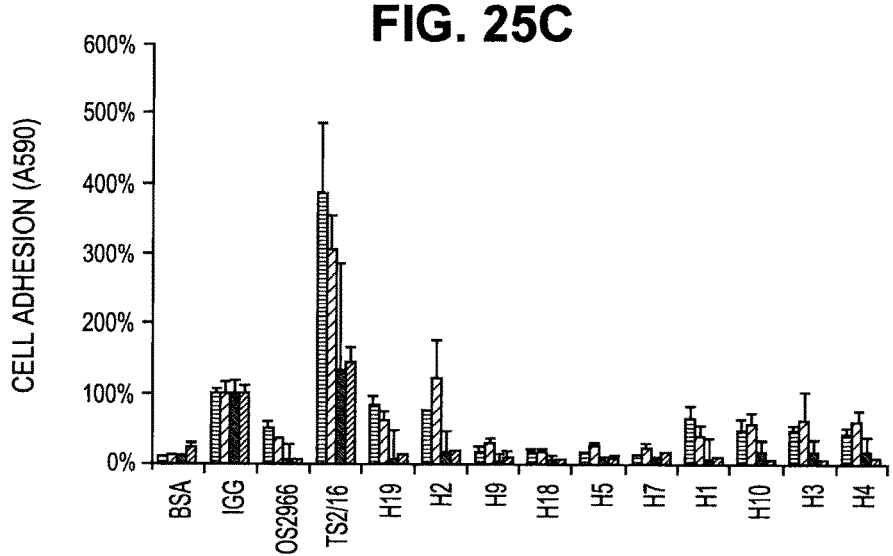

Functional inhibition of the integrin β1 subunit with the human variant antibodies was assessed in an adhesion microplate assay on multiple ECM and in multiple cancer cell lines PANC-1 human pancreatic cancer (FIGS. 25A and 25B), MDA-MB-231 human triple negative breast cancer (FIG. 25C), and AsPC-1 human pancreatic cancer (FIG. 25D). In brief, ECM adhesion assays were performed with 10 ECM components or BSA (control). Cells were pre-incubated with 10 µg/ml antibodies in serum-free DMEM/F12 media for 30 min Adhesion was tested for 30 min to 1 hr. Non-adherent cells were removed from dishes, cells fixed with 1% paraformaldehyde, and plates stained with crystal violet for 30 min. After extensive rinsing, crystal violet was solubilized in Triton X-100 for 1 hr and plates read for absorbance at A590.

All 19 human variants were functionally active in attenuating cell adhesion to all ECM with some significant variation depending on ECM protein and cell line. Relative affinities (Table 3) do not demonstrate obvious correlation to function in this assay regardless of ECM type or cell line. These data were normalized to IgG negative control (BSA, bovine serum albumin as negative control; IgG, isotype control; OS2966, murine OS2966; TS2/16, positive control integrin β1 activating antibody; FN, fibronectin; LN, laminin; C1, collagen type I; C4, collagen type IV).

Figure 26A:
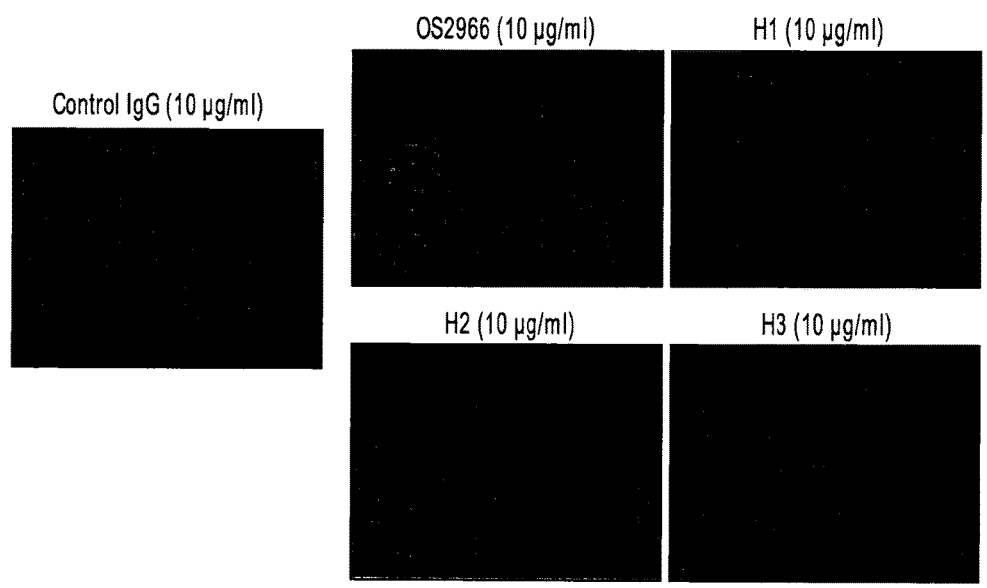
FIGS. 26A-B is a series of pictorial and graphical representations illustrating functional validation in extracellular matrix (ECM) migration assays of composite human antibody variants of the present invention. Functional inhibition of the integrin β1 subunit with composite human antibody variants of the present invention (from Table 2) was assessed in a microplate "scratch wound" migration assay on ECM component fibronectin with human triple negative breast cancer cells (MDA-MB-231).
Figure 26B:
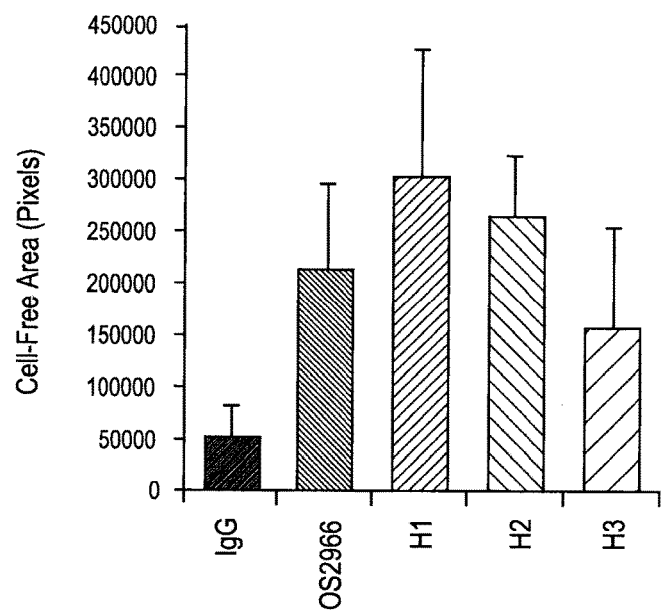

Functional inhibition of the integrin β1 subunit with the human variant antibodies was assessed in a microplate "scratch wound" migration assay on ECM component fibronectin with human triple negative breast cancer cells (MDA-MB-231). Briefly, plates were coated with 10 µg/ml fibronectin and seeded with tumor cells. A yellow pipette tip was used to scratch monolayers of confluent cells and media replaced including 10 µg/ml of stated antibodies. Plates were fixed after 8 hr incubation at 37 C and imaged. 10× magnification images of plates demonstrate attenuation of migration into the wound in OS2966 and composite human variant (H1, H2, H3) treated wells (FIG. 26A). Quantitation of cell free area for each condition (performed in triplicate and repeated) is shown in FIG. 26B.

Migration of triple negative breast cancer cells was significantly attenuated by treatment with OS2966 composite human variants.

Figure 27A:
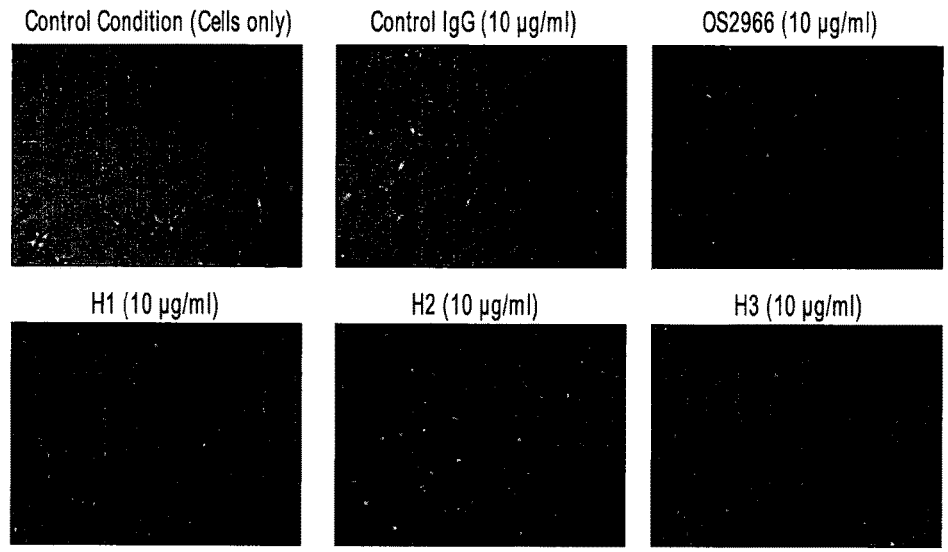
FIGS. 27A-B is a series of pictorial and graphical representations illustrating functional validation in tube forming angiogenesis assays with human umbilical vein endothelial cells (HUVEC) of composite human antibody variants of the present invention. Functional inhibition of the integrin β1 subunit with composite human antibody variants of the present invention (from Table 2) was assessed in an in vitro model of angiogenesis; the tube forming assay with human umbilical vein endothelial cells (HUVEC).
Figure 27B:
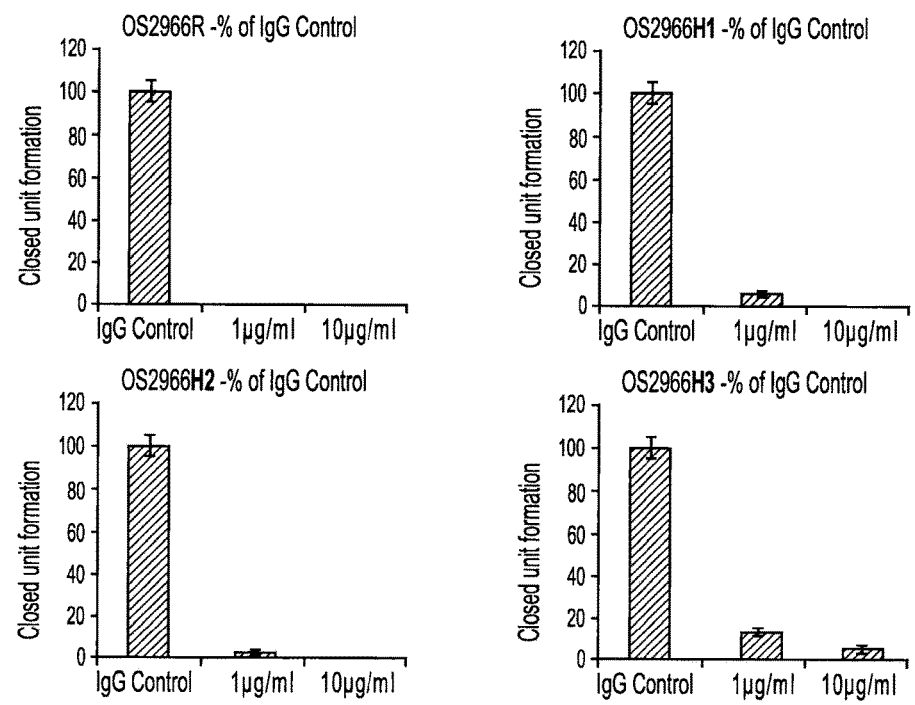

Functional inhibition of the integrin β1 subunit with the human variant antibodies was assessed in an in vitro model of angiogenesis; the tube forming assay with human umbilical vein endothelial cells (HUVEC). Briefly, plates were coated with Matrigel ECM and seeded with HUVEC cells. Plates were imaged after 8 hr incubation at 37 C and quantitated for vascular tube formation (closed unit formation). 10× magnification images of plates demonstrate attenuation of vascular tube formation in OS2966 and composite human variant (H1, H2, H3) treated wells (FIG. 27A). Quantitation of closed unit formation for each condition (performed in at least triplicate and repeated with endothelial progenitor cells) is shown in FIG. 27B.

The composite human variants completely block angiogenesis in the in vitro tube forming assay.

Figure 28A:
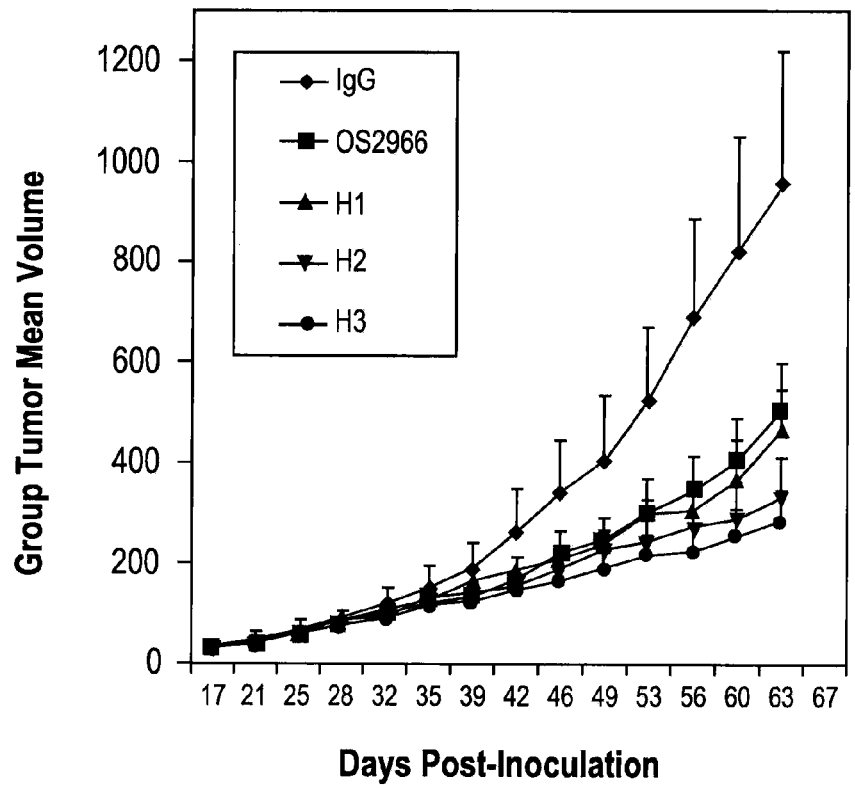
FIGS. 28A-B is a series of pictorial and graphical representations illustrating functional validation in a human orthotopic xenograft model of triple negative breast cancer of composite human antibody variants of the present invention. Functional inhibition of the integrin β1 subunit with composite human antibody variants of the present invention (from Table 2) was assessed in an in vivo model of human triple negative breast cancer with the MDA-MB-231 cell line.
Figure 28B:
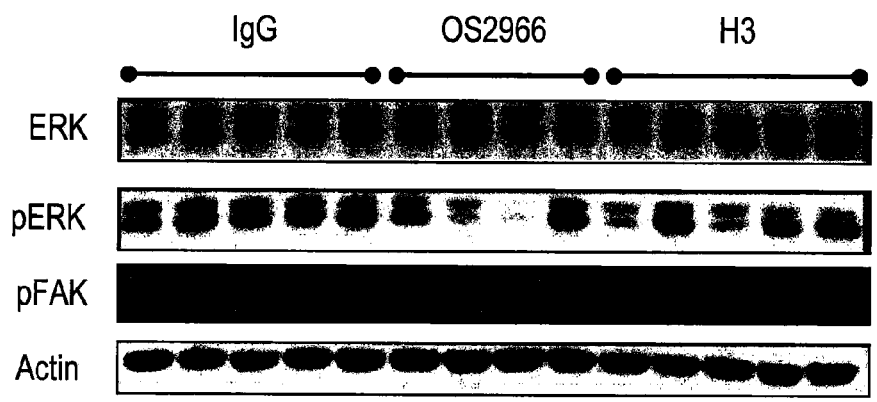

Functional inhibition of the integrin β1 subunit with the human variant antibodies was assessed in an in vivo model of human triple negative breast cancer with the MDA-MB-231 cell line. Briefly, $10^6$ cells were injected into the $4^{th}$ mammary fat pad in 5- to 6-week old female nude athymic nu/nu mice. Mice were randomized into treatment groups after tumors were established (mean subcutaneous volume=80-100 mm$^3$). Control and experimental antibodies were administered at 5 mg/kg intraperitoneally (IP) twice weekly. Human IgG at equivalent doses served as the control (Sigma). Orthotopic tumors were measured with calipers twice weekly. As shown in FIG. 28A, human variants H1-H3 significantly attenuated growth of MDA-MB-231 tumors in vivo compared to IgG control. A trend towards superior efficacy for the composite human variants was apparent compared to murine OS2966, particularly for H3. Pharmacodynamic Western Blot analysis demonstrated a reduction of activities in critical pro-growth signaling pathways (phosphorylated Extracellular-related Kinase, ERK and phosphorylated Focal Adhesion Kinase, FAK) in the treated tumors compared to control which may have contributed to reduced proliferation and elevation of apoptosis (FIG. 28B).

Figure 29:
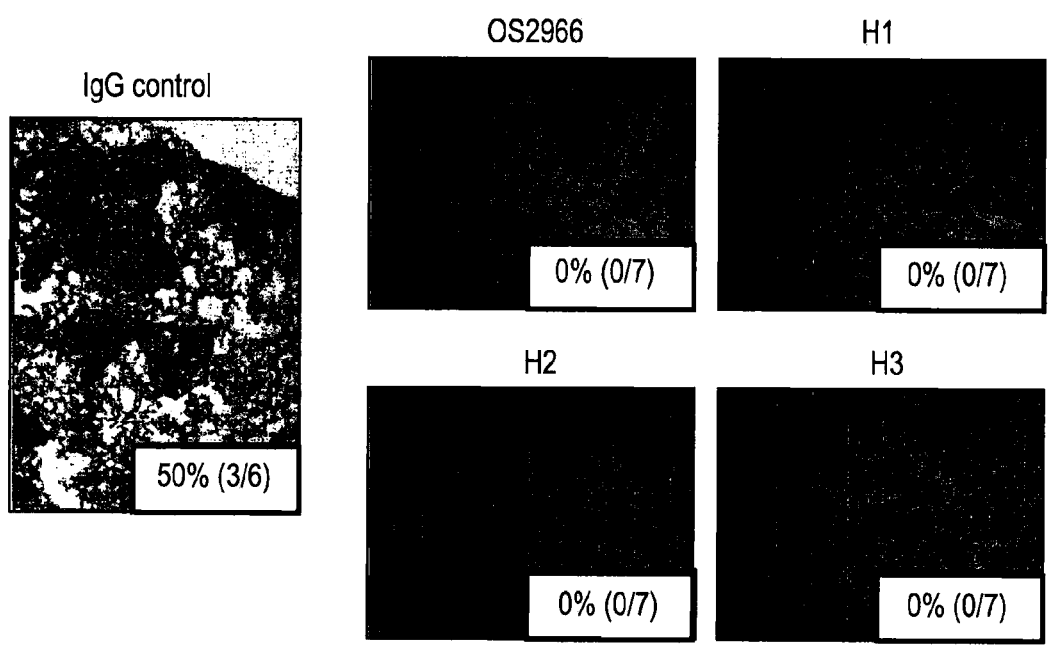
FIG. 29 is a series of pictorial representations illustrating functional validation in a human orthotopic xenograft model of spontaneous lung metastasis from triple negative breast cancer of composite human antibody variants of the present invention.

Functional inhibition of the integrin β1 subunit with the human variant antibodies was assessed in an in vivo model of spontaneous lung metastasis with human triple negative breast cancer with the MDA-MB-231 cell line. Briefly, $10^6$ cells were injected into the $4^{th}$ mammary fat pad in 5- to 6-week old female nude athymic nu/nu mice. Mice were randomized into treatment groups after tumors were established (mean subcutaneous volume=80-100 mm$^3$). Control and experimental antibodies were administered at 5 mg/kg intraperitoneally (IP) twice weekly. Human IgG at equivalent doses served as the control (Sigma). After 7 weeks, mice were perfused, lungs collected, and sectioned coronally for H&E analysis. Spontaneous lung metastasis was observed in 50% (3 of 6) of mice given IgG control antibody. Spontaneous lung metastases were not observed in any mice given OS2966 or composite human variants H1-H3 (0%, 0/28 mice). Results are shown in FIG. 29.

Composite human variants completely prevented spontaneous lung metastasis in an orthotopic model of triple negative breast cancer.

Figure 30A:
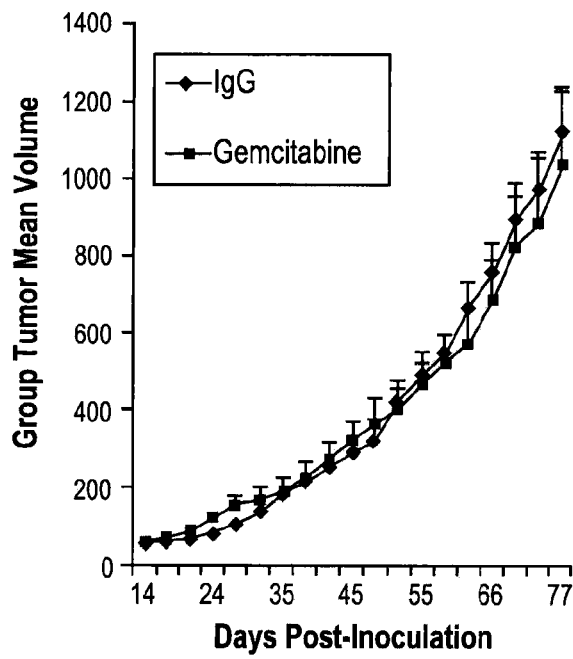
FIGS. 30A-C is a series of pictorial and graphical representations illustrating functional validation in a human xenograft model of pancreatic cancer of composite human antibody variants of the present invention. Functional inhibition of the integrin β1 subunit with composite human antibody variants of the present invention (from Table 2) was assessed in an in vivo model of human gemcitabine resistant pancreatic cancer with the PANC1-GEMR cell line.
Figure 30B:
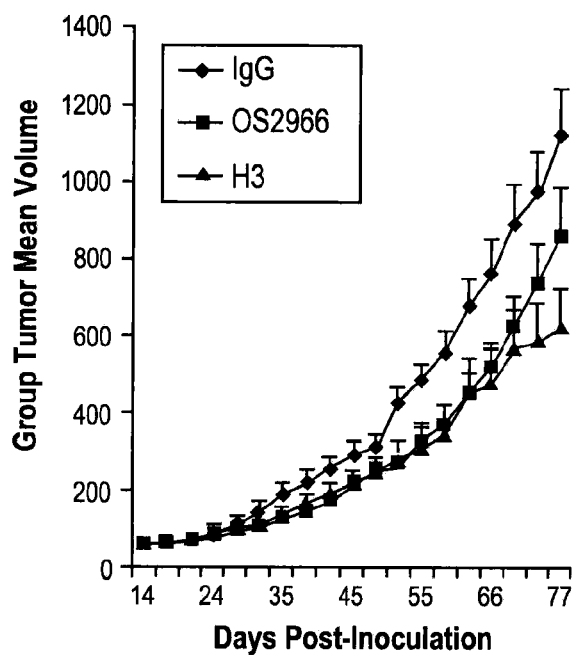
Figure 30C:
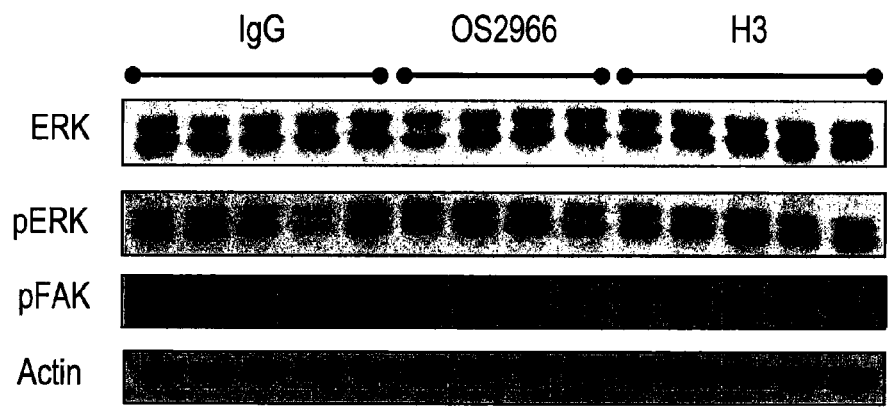

Functional inhibition of the integrin β1 subunit with the human variant antibodies was assessed in an in vivo model of human gemcitabine resistant pancreatic cancer with the PANC1-GEMR cell line. Briefly, $10^6$ cells were injected subcutaneously in 5- to 6-week old male nude athymic nu/nu mice. Mice were randomized into treatment groups after tumors were established (mean subcutaneous volume=80-100 mm$^3$). Control and experimental antibodies were administered at 5 mg/kg intraperitoneally (IP) twice weekly or gemcitabine at 50 mg/kg. Human IgG at equivalent doses served as the control (Sigma). Subcutaneous tumors were measured with calipers twice weekly. FIG. 30A shows in vivo verification of gemcitabine resistance in the PANC1-GEMR line. FIG. 30B shows that composite human variant H3 significantly attenuated growth of PANC1-GEMR tumors in vivo compared to IgG control. FIG. 30C shows Pharmacodynamic Western Blot analysis of critical pro-growth signaling pathways (phosphorylated Extracellular-related Kinase, ERK and phosphorylated Focal Adhesion Kinase, FAK) in the treated tumors compared to control which may have contributed to reduced proliferation and elevation of apoptosis.

Figure 31A:
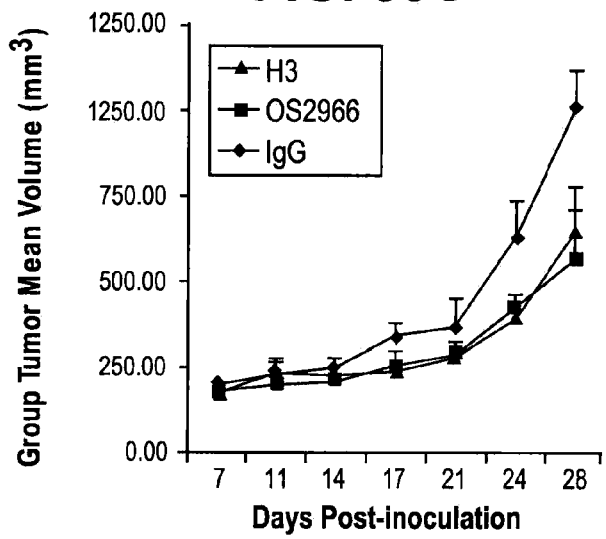
FIGS. 31A-B is a series of pictorial and graphical representations illustrating functional validation in a human xenograft model of established glioblasoma of composite human antibody variants of the present invention. Functional inhibition of the integrin β1 subunit with composite human antibody variants of the present invention (from Table 2) was assessed in an in vivo model of established human glioblastoma with the U87MG cell line.
Figure 31B:
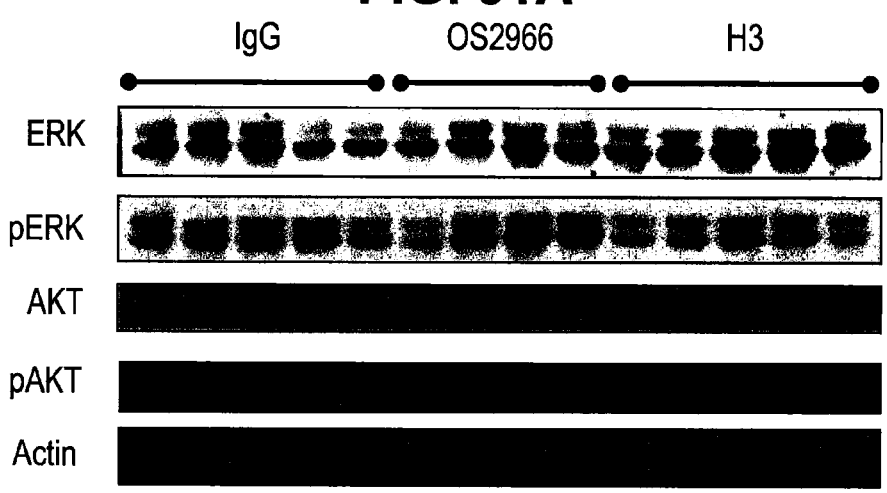

Functional inhibition of the integrin β1 subunit with the human variant antibodies was assessed in an in vivo model of established human glioblastoma with the U87MG cell line. Briefly, $10^7$ cells were injected subcutaneously in 5- to 6-week old male nude athymic nu/nu mice. Mice were randomized into treatment groups after tumors were well established (mean subcutaneous volume=~200-250 mm$^3$). Control and experimental antibodies were administered at 5 mg/kg intraperitoneally (IP) twice weekly. Human IgG at equivalent doses served as the control (Sigma). Subcutaneous tumors were measured with calipers twice weekly. FIG. 31A demonstrates that composite human variant H3 significantly attenuated growth of established glioblastoma tumors in vivo compared to IgG control. Efficacy of H3 was equivalent to murine OS2966. Pharmacodynamic Western Blot analysis demonstrated a reduction of activities in critical pro-growth signaling pathways (phosphorylated Extracellular-related Kinase, ERK and phosphorylated AkT) in the H3 treated tumors compared to control which may have contributed to reduced proliferation and elevation of apoptosis as shown in FIG. 31B.

Figures 32A, 32B:
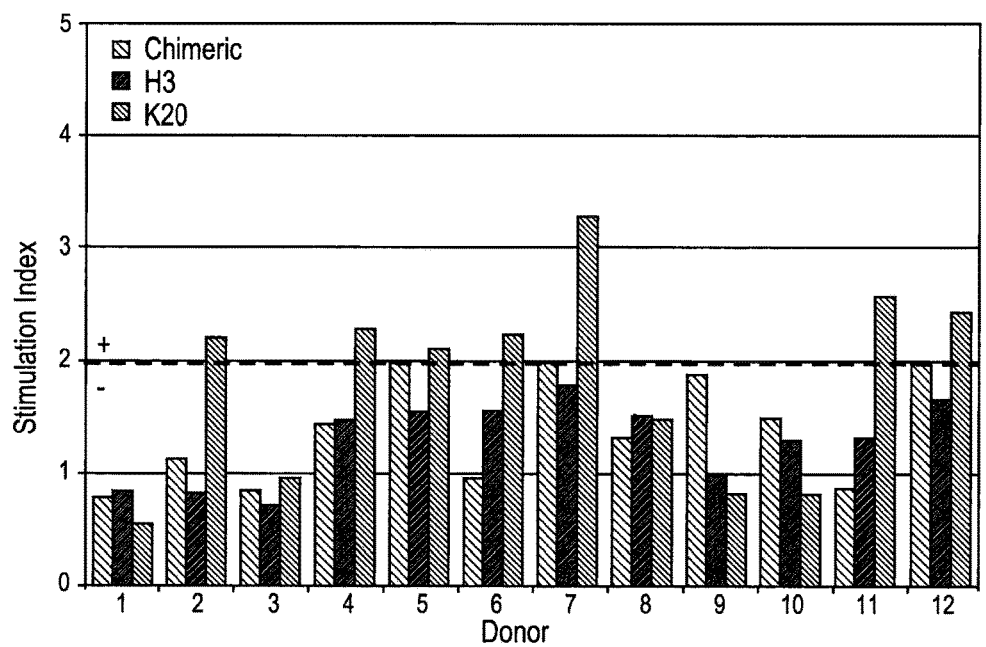
FIGS. 32A-B depicts results of an immunogenicity screening assay (EpiScreen™).

The EpiScreen™ time course T cell proliferation assay was used to determine the potential for clinical immunogenicity of antibody variant H3. The fully humanized and chimeric antibodies were tested for their ability to induce CD4$^+$ T cell responses as measured by proliferation against a panel of 12 HLA-typed donors. Healthy donor T cell proliferation responses to the chimeric (murine/human) OS2966 antibody, humanized H3 antibody and a positive control humanized antibody are shown in FIG. 32A. CD4+ T cells were incubated with autologous mature DC loaded with the samples and assessed for proliferation after 7 days incubation. Proliferation responses with an SI≥2.00 (indicated by red dotted line) that were significant (p<0.05) using an unpaired, two sample student's t test were considered positive. FIG. 32B provides a summary of healthy donor T cell proliferation responses to the donor cohort. Positive (SI≥2.00, significant p<0.05) T cell responses for proliferation ("P") are shown. Borderline responses (significant p<0.05 with SI≥1.90) are shown (*). The frequency of positive responses for the proliferation assay are shown as a percentage at the bottom of the columns. A33 (humanized A33) is the clinical benchmark control mAb that shows high levels of immunogenicity in the clinic and routinely induces 20-30% T cell responses in the EpiScreen assay. For each donor, an immunogenic reproducibility control (cells incubated with 100 µg/ml KLH) was also included.

The composite human variant H3 demonstrated significantly reduced immunogenicity (0% responses) compared to the OS2966 murine/human chimera (25% responses). It is concluded that the human antibody H3 exhibits a clinically acceptable immunogenicity profile from the EpiScreen™ assay providing confirmation of reduced immunogenicity as a result of the Antitope Composite Human Antibody technology.

Although the invention has been described with reference to the above example, it will be understood that modifications and variations are encompassed within the spirit and scope of the invention. Accordingly, the invention is limited only by the following claims.

What is claimed is:

1. A humanized antibody which specifically binds integrin β1 comprising a heavy chain variable (VH) region and a light chain variable (VL) region,
    wherein the VH region and the VL region have amino acid sequences as set forth in SEQ ID NOs:6 and 16, SEQ ID NOs:6 and 18, SEQ ID NOs:6 and 20, SEQ ID NOs:8 and 16, SEQ ID NOs:8 and 18, SEQ ID NOs:8 and 20, SEQ ID NOs:8 and 22, SEQ ID NOs:10 and 16, SEQ ID NOs:10 and 18, SEQ ID NOs:10 and 20, SEQ ID NOs:10 and 22, SEQ ID NOs:12 and 16, SEQ ID NOs:12 and 18, SEQ ID NOs:12 and 20, SEQ ID NOs:12 and 22, SEQ ID NOs:14 and 16, SEQ ID NOs:14 and 18, SEQ ID NOs:14 and 20, and SEQ ID NOs:14 and 22.

2. The antibody of claim 1, wherein CDRs of the VH and VL regions are from a donor antibody.

3. The antibody of claim 1, wherein the antibody comprises an Fc region.

4. The antibody of claim 3, wherein the Fc region is of IgG1, IgG2, IgG3, or IgG4.

5. The antibody of claim 4, wherein the Fc region is a human IgG1 or IgG4.

6. The antibody of claim 1, wherein the antibody comprises a light chain constant region.

7. The antibody of claim 6, wherein the light chain constant region is of isotype kappa.

8. The antibody of claim 1, wherein the antibody is an scFv or Fab.

9. The antibody of claim 1, wherein the antibody is a humanized antibody.

10. The antibody of claim 1, wherein the antibody is a chimeric antibody.

11. The antibody of claim 1, wherein the antibody binds integrin β1 with an equilibrium dissociation constant (Kd) of at least $10^{-2}$M, $10^{-3}$M, $10^{-4}$M, $10^{-5}$M, $10^{-6}$M, $10^{-7}$M, $10^{-8}$M, $10^{-9}$M or $10^{-10}$M.

12. The antibody of claim 1, which when tested in vitro for induction of CD4+ helper T cell responses in blood samples with a distribution of HLA-DR allotypes from the human population, gives rise to less than 10% of T cell responses.

13. The antibody of claim 12, which when tested gives rise to less than 5%, 4%, 3%, 2%, 1%, 0.5% or 0.1% of T cell responses.

14. A multi-specific antibody comprising an antibody of claim 1.

15. A pharmaceutical composition comprising the antibody of claim 1 and a pharmaceutically acceptable carrier.

16. An immunoconjugate comprising the antibody of claim 1 linked to a detectable or therapeutic moiety.

17. The immunoconjugate of claim 16, wherein the therapeutic moiety is a cytotoxic moiety.

18. The immunoconjugate of claim 16, wherein the therapeutic moiety is a chemotherapeutic agent.

19. The immunoconjugate of claim 16, wherein the detectable moiety is a fluorescent moiety.

20. The antibody of claim 1, wherein the VH region and the VL region have amino acid sequences as set forth in SEQ ID NOs:10 and 16, SEQ ID NOs:12 and 22, or SEQ ID NOs:14 and 20.

21. The antibody of claim 1, wherein the VH region and the VL region have amino acid sequences as set forth in SEQ ID NOs:12 and 22.

* * * * *